US009751898B2

(12) United States Patent
Hernandez et al.

(10) Patent No.: US 9,751,898 B2
(45) Date of Patent: *Sep. 5, 2017

(54) BORON-CONTAINING SMALL MOLECULES

(71) Applicant: Anacor Pharmaceuticals, Inc., Palo Alto, CA (US)

(72) Inventors: Vincent S. Hernandez, Watsonville, CA (US); Charles Ding, San Mateo, CA (US); Jacob J. Plattner, Orinda, CA (US); Michael Richard Kevin Alley, Santa Clara, CA (US); Fernando Rock, Los Altos, CA (US); Suoming Zhang, San Mateo, CA (US); Eric Easom, Mountain View, CA (US); Xianfeng Li, Cupertino, CA (US); Ding Zhou, Shanghai (CN)

(73) Assignee: Anacor Pharmaceuticals, Inc., Palo Alto, CA (US)

(*) Notice: Subject to any disclaimer, the term of this patent is extended or adjusted under 35 U.S.C. 154(b) by 173 days.

This patent is subject to a terminal disclaimer.

(21) Appl. No.: 14/221,637

(22) Filed: Mar. 21, 2014

(65) Prior Publication Data
US 2014/0315860 A1 Oct. 23, 2014

Related U.S. Application Data

(63) Continuation of application No. 13/227,444, filed on Sep. 7, 2011, now Pat. No. 8,703,742.

(60) Provisional application No. 61/380,596, filed on Sep. 7, 2010.

(51) Int. Cl.
*C07F 5/02* (2006.01)

(52) U.S. Cl.
CPC .................................. *C07F 5/025* (2013.01)

(58) Field of Classification Search
CPC ....................................................... C07F 5/025
See application file for complete search history.

(56) References Cited

U.S. PATENT DOCUMENTS

| | | |
|---|---|---|
| 2,260,336 A | 10/1941 | Prescott et al. |
| 3,686,398 A | 8/1972 | Kohn et al. |
| 3,873,279 A | 3/1975 | Singer |
| 4,602,011 A | 7/1986 | West et al. |
| 4,716,035 A | 12/1987 | Sampathkamar |
| 4,766,113 A | 8/1988 | West et al. |
| 4,894,220 A | 1/1990 | Nabi et al. |
| 4,919,934 A | 4/1990 | Deckner et al. |
| 5,274,792 A | 12/1993 | Sato et al. |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,221,640 B1 | 4/2001 | Tao et al. |
| 6,306,628 B1 | 10/2001 | Rothschild et al. |
| 6,369,098 B1 | 4/2002 | Pershadsingh et al. |
| 6,521,619 B2 | 2/2003 | Link et al. |
| 6,800,645 B1 | 10/2004 | Cox et al. |
| 6,855,848 B2 | 2/2005 | Scherer et al. |
| 7,169,603 B2 | 1/2007 | Hedley et al. |
| 7,205,425 B2 | 4/2007 | Shibasaki et al. |
| 7,217,701 B2 | 5/2007 | Mikoshiba et al. |
| 7,390,806 B2 | 6/2008 | Lee et al. |
| 7,446,236 B2 | 11/2008 | Naud et al. |
| 7,465,836 B2 | 12/2008 | Lee et al. |
| 7,582,621 B2 | 9/2009 | Baker et al. |
| 7,767,657 B2 | 8/2010 | Baker et al. |
| 7,816,344 B2 | 10/2010 | Baker et al. |
| 8,039,450 B2 | 10/2011 | Akama et al. |
| 8,039,451 B2 | 10/2011 | Baker et al. |
| 8,115,026 B2 | 2/2012 | Baker et al. |
| 8,168,614 B2 | 5/2012 | Baker et al. |
| 8,343,944 B2 | 1/2013 | Xia et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0077601 A1 | 4/2004 | Adams et al. |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0048570 A1 | 2/2010 | Kim et al. |
| 2010/0256092 A1 | 10/2010 | Xia et al. |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9622023 A1 | 7/1996 |
| WO | WO 9812206 A1 | 3/1998 |
| WO | WO 0027822 | 5/2000 |
| WO | WO 0044387 A1 | 8/2000 |
| WO | WO 0075142 A2 | 12/2000 |
| WO | WO 0114578 A1 | 3/2001 |

(Continued)

OTHER PUBLICATIONS

"*Drug Synthesis Experiment*", Wang Shifan, China Medical Science Press, 2007, 1$^{st}$ edition.
"*Medicinal Chemistry Introduction*", Guo Zongru, China Medical Science Press, 1994, 1$^{st}$ edition.
U.S. Appl. No. 13/673,860, filed Nov. 9, 2012.

(Continued)

*Primary Examiner* — Sarah Pihonak
*Assistant Examiner* — Jason A Deck
(74) *Attorney, Agent, or Firm* — Morgan, Lewis & Bockius LLP

(57) ABSTRACT

This invention relates to, among other items, benzoxaborole compounds and their use for treating bacterial infections.

8 Claims, 1 Drawing Sheet

(56) References Cited

FOREIGN PATENT DOCUMENTS

| | | |
|---|---|---|
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |
| WO | WO 2010/080558 A1 | 7/2010 |

OTHER PUBLICATIONS

U.S. Appl. No. 13/607,405, filed Sep. 7, 2012.
U.S. Appl. No. 13/607,250, filed Sep. 7, 2012.
U.S. Appl. No. 13/607,321, filed Sep. 7, 2012.
U.S. Appl. No. 13/356,488, filed Jan. 23, 2012.
U.S. Appl. No. 13/224,252, filed Sep. 1, 2011.
U.S. Appl. No. 13/453,682, filed Apr. 23, 2012.
U.S. Appl. No. 11/762,038, filed Jun. 12, 2007.
U.S. Appl. No. 11/865,725, filed Oct. 1, 2007, now abandoned.
U.S. Appl. No. 12/752,789, filed Apr. 1, 2010, now abandoned.
U.S. Appl. No. 12/848,051, filed Jul. 30, 2010.
U.S. Appl. No. 13/236,543, filed Sep. 19, 2011.
U.S. Appl. No. 13/062,450, filed Mar. 4, 2011.
U.S. Appl. No. 12/464,829, filed May 12, 2009.
U.S. Appl. No. 12/641,318, filed Dec. 17, 2009.
U.S. Appl. No. 12/873,036, filed Aug. 31, 2010.
U.S. Appl. No. 13/062,491, filed Mar. 4, 2011.
U.S. Appl. No. 13/503,016, filed Jun. 25, 2012.
U.S. Appl. No. 12/857,305, filed Aug. 16, 2010, now abandoned.
U.S. Appl. No. 12/852,351, filed Aug. 6, 2010.
U.S. Appl. No. 12/944,690, filed Nov. 11, 2010.
U.S. Appl. No. 13/015,487, filed Jan. 27, 2011.
U.S. Appl. No. 12/944,699, filed Nov. 11, 2010.
U.S. Appl. No. 13/062,466, filed Mar. 4, 2011.
U.S. Appl. No. 13/639,594, filed Sep. 7, 2012.
U.S. Appl. No. 13/636,114, filed Sep. 19, 2012.
U.S. Appl. No. 13/678,576, filed Nov. 16, 2012.
U.S. Appl. No. 13/678,578, filed Nov. 16, 2012.
Adamczyk-Wozniac, et al., "Benzoxaboroles—Old Compounds with new applications", Journal of Organometalic Chemistry 694;3533-3541 (2009).
Akama, et al., "Discovery and structure-activity study of novel benzoxaborole anti-inflammatory agent (AN2728) for the potential topical treatment of psoriasis and atopic dernatitis", Bioorganic & Medicinal Chemistry Letters, (2009) 19: 2129-2132.
Alley, et al., "Recent Progress on Topical Therapy of Onychomycosis", Expert Opinion Investigate Drugs(Feb. 2007) 16(2): 157-67.
Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Progress on New Therapeutics for Fungal Nail Infections", Annual Reports in Medicinal Chemistry, vol. 40: pp. 323-335, (2005).
Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Cummings, et al., "Arylboronic Acids. A Medium-Size Ring Containing Boronic Ester Groups", Arylboronic Acids, vol. 34, No. 6; pp. 1669-1674 (Jun. 1969).
Cusack, S., et al., "The 2 A Crystal Structure of leucyl-tRNA Synthetase and its Complex with a Leucyl-Adenylate Analogue." EMBO Journal, vol. 19; pp. 2351-2361, (2000).
Dale, et al., "Substituted Styrenes VIII Syntheses and some Reactions of the Vinylbenzeneboronic Acids" J. Org. Chem. vol. 27; pp. 2598-2603, (Jan. 1, 1962).
Denis, "Pharmacology 1104 Lecture: Drug Classifications & Characteristics of Antimicrobials" (2003).
Dian, "International Nomenclature of Organics", China Petrochemical Press, 1st Edition; 50-51 (Jan. 21, 2004).
Falck, et al., "Bromo-Boronolactonization of Olefins", J. Org. Chem., vol. 66; pp. 7148-7150 (2001).
Farfan, et al., "Through-Bond Modulation on N—B Ring Formation Shown by NMR and X-Ray Diffraction Studies of Borate Derivatives of Pyridyl Alcohols," J. Chem. Soc. Perkin Trans., vol. 2; pp. 527-532 (1992).
Ferrer, "Targeting Aminocytl-tRNA Synthetases for the Treatment of Fungal Infections", Drug News Perspective, vol. 19, No. 6; pp. 347-348, (Jul./Aug. 2006).
Fungicide: Definition from Answer.com, (1998).
Goodman, et al., "Goodman & Gilman's Manual of Pharmacology and Therapeutics" Chapter 40;681-694 (2008).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).
Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Arydialkkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).

(56) References Cited

OTHER PUBLICATIONS

Hui, et al., "In Vitro Penetration of a Novel Oxaborole Antifungal (AN2690) into the Human Nail Plate", Journal of Pharmaceutical Sciences (2007) 96(10): 2622-2631.
Koster, et al., "Ein Am Bor Alkyliertes Carboran-2,3" Tetrahedron Letters, No. 25; pp. 1667-1670 (1964).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).
Lampe, et al., "Synthesis and Protien Kinase Inhibitory Activity of Balanol Analogues with Modified Benzophenone Subunits", J. Med. Chem., vol. 45(12); pp. 2624-2643, (2002).
Lee, K., et al., "Molecular Study of the Editing Active Site of *Escherichia coli* Leucyl-tRNA Synthetase: Two Amino Acid Binding Site in the Editing Domain", vol. 54; pp. 693-704, (2004).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Luan, et al., "Inhibition of Experimental Periodontitis by a topical boron-base antimicrobial" J Dent. Res, 87(2):148-152 (2008).
McMillin, et al., "Systemic Aspects of Psoriasis: An Integrative Model Based on Intestinal Etiology", Int. Med. vol. 2, Issue 2/3, (1999).
Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Mudran, "Drug Delivery to the Nail Following Topical Application", International Journal of Pharmaceutics, vol. 236: pp. 1-26, (2002).
Murugesan, et al., "Biphenylsulfonamide Endothelin Antagonists: Structure-Activity Relationships of a Series of Mono- and Disubstituted Analogues and Pharmacology of the Orally Active Endothelin Antagonist 2'-Amino-N-(3,4-dimethyl-5-isoxazolyl)-4'-(2-methylpropyl)[1,1'-biphenyl]-2-sulfonamide",J. Med. Chem vol. 41; pp. 5198-5218 (1998).
Patani, et al., "Bioisosterism: A Rational Approach to Drug Design", Chem. Rev., vol. 96; pp. 3147-3176 (1996).
Perola, E., et al., "Successful Virtual Screening of a Chemical Database for Farnesltransferase Inhibitor Leads." vol. 43; pp. 401-4008, (2000).
Qin, et al., "Luminescent Organoboron Quinolate Polymers," Journal of the American Chemical Society, vol. 126, No. 22; pp. 7015-7018, (Jun. 9, 2004).
Qin, Clinical Mycology, Fudan Press, Shanghai Medical University Press, pp. 92, 111, 340-341, 365, 437 and 487 (2001) With English Translation.
Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).
Silverman, "The Organic Chemistry of Drug Design and Drug Action", 2nd Edition, Northwestern University, Department of Chemistry, Evanston, Illinois, Section 2: 29-32 (2004).
Snyder, et al. "Common Bacteria Whose Susceptibility to Antimicrobials in no longer Predictable" J. Med. Liban, vol. 48 No. 4; pp. 208-214, (2000).
Sporzynski, et al., "1,3-Dihydro-1-hydroxy-3-morpholin-4-yl-2,1-benzoxaborole: product of the reaction of o-formylphenylboronic acid with morpholine", Appl. Organometal. Chem., vol. 19; pp. 1202-1203, (2005).
Sugar, et al., "Comparison of Three Methods of Antifungal Susceptibility Testing with the Proposed NCCLS Standard Broth Macrodilution Assay: Lack of Effect of Phenol Red" Diagn. Microbiol. Infect. Dis. vol. 21; pp. 129-133, (1995).
Tabuchi, et al., "Anticoccidial Activity of some Azacyclo Organoborinates," Heterocycles, vol. 60, No. 01; pp. 177-182, (2003).
Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).
Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).
Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).
Tschampel, et al., "Arylboronic Acids. VII. Some Reactions to o-Formybenzeneboronic Acids", J. Org. Chem. vol. 29, No. 8; pp. 2168-2172, (1964).
Turner, et al., Current Pharmaceutical Design, vol. 2; pp. 209-224 (1996).
Vippagunta, "Crystalline Solids", Advanced Drug Delivery Reviews, vol. 48; pp. 3-26, (2001).
Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).
Ye, et al., "Convenient and Versatile Syntheis of formyl-substituted Benzoxaboroles", Tetrahedron, vol. 65; pp. 8738-8744, (2009).
Williams, et al., "Foye's Principles of Medicinal Chemistry", 5th Edition, 2002, Lippincoot Williams & Wilkins, p. 59.
Zhdankin, et al., "Synthesis and Structure of Benzoboroxoles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).
Zhou, et al., "Pattern Recognition of Proteins Based on an Array of Functionalized Porphyrins," J. Am. Chem. Soc., 128:2421-2425 (2006).
Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).
"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.
"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.
"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.
"AN2718 Demonstrates Significant Efficacy in Three Phase Ib Psoriasis Microplaque Trials" Scientific Presentation at the American Academy of Dermatology Annual Meeting, San Francisco, CA Mar. 6-10, 2009.
"AN2728 Demonstrates Significant Safety and Efficacy in Phase IIa Double Blind Trial in Plaque Type Psoriasis", Scientific Presentation at the American Academy of Dermatology Annual Meeting, San Francisco, CA, Mar. 6-10, 2009.

(56) References Cited

OTHER PUBLICATIONS

"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.
"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.
"AN2920, A Novel Oxaborole, Shows In Vitro and In Vivo Activity Against *Trypanosomal brucei*", Scientific Presentation at the American Society of Tropical Medicine and Hygiene Conference, New Orleans, LA Dec. 7-11, 2008.
"A Novel Oxaborole, AN3520, Show Efficacy against Human African Trypanomiasis In Vitro and In Vivo, Including Promise in a Murine CNS Model of T. brucei Infection", Scientific Presentation at the American Society of Tropical Medicine and Hygiene Conference, New Orleans, LA Dec. 7-11, 2008.
"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.
"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.
"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.
"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.
"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.
"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.
"Preclinical Toxicology of AN2728, a Novel Borinic Acid Ester with Anti-Inflammatory Activity", American Academy of Dermatology, 65th Annual Meeting, Washington, DC, Feb. 2-6, 2007.
"AN2728, a Novel Oxaborole with Broad-Spectrum In Vitro Anti-Inflammatory Activity", American Academy of Dermatology, 65th Annual Meeting, Washington, DC, Feb. 2-6, 2007.
"In Vitro Nail Penetration of AN2690, Effect of Vehicle and Co-Efficient of Efficacy", American Academy of Dermatology, 65th Annual Meeting, Washington, DC, Feb. 2-6, 2007.
"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.
"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.
"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.
"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.
"Skin Penetration and Anti-Inflammatory Activity of AN2728, a Novel Oxaborole", American Academy of Dermatology, 65th Annual Meeting, Washington, DC, Feb. 2-6, 2007.
"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

| Compound # | A. baumannii ATCC 17978 MIC | E. coli ATCC 25922 MIC | H. influenzae ATCC 49766 MIC | K. pneumoniae ATCC 13883 MIC | P. aeruginosa ATCC 27853 MIC | MABA M. tuberculosis H37Rv MIC | LORA M. tuberculosis H37Rv MIC | M. tuberculosis LeuRS IC50 (uM) |
|---|---|---|---|---|---|---|---|---|
| A | 16 | 6 | 3 | 6 | 20 | 0.37 | >64 | 0.97 |
| B | >64 | >64 | 2 | >64 | >64 | <0.025 | >64 | 0.13 |
| C | 8 | 4 | 1 | 4 | >64 | 0.04 | 0.52 | 0.13 |
| D | >64 | >64 | 0.5 | >64 | >64 | <0.02 | 0.07 | 0.09 |
| E | >64 | >64 | 1 | >64 | >64 | 0.05 | 0.70 | 0.07 |
| F | >64 | >64 | NT | >64 | >64 | <0.2 | 26.20 | 0.2 |
| G | 8 | 16 | NT | 8 | >64 | <0.2 | 31.90 | 0.31 |
| H | >64 | >64 | NT | >64 | >64 | 16.80 | 48.46 | 27.6 |
| I | >64 | >64 | NT | >64 | >64 | 0.30 | <0.391 | 0.04 |
| J | >64 | >64 | NT | >64 | >64 | 0.59 | 0.69 | 0.03 |
| K | >64 | >64 | >64 | >64 | >64 | >64 | NT | NT |
| L | >64 | 64 | <0.12 | 32 | >64 | <0.004 | <0.039 | 0.02 |
| M | >64 | >64 | NT | >64 | >64 | NT | NT | 21.02 |
| N | 1.5 | 0.5 | NT | 1 | 3 | NT | NT | 0.09 |
| O | 32 | 0.74 | 8 | 8 | 64 | 0.28 | >64 | 0.91 |
| P | 32 | NT | 4 | 8 | 32 | 1.91 | >64 | 0.896 |
| Q | 32 | 1.1 | 16 | 8 | 64 | 3.73 | >64 | 0.878 |
| R | >64 | 1.6 | 16 | 8 | 64 | 1.01 | >64 | 0.892 |
| S | >64 | 1.1 | 8 | 8 | 64 | 0.88 | >50 | 0.61 |
| T | 16 | 1.345292 | 16 | 8 | 16 | NT | NT | 0.895 |
| U | 16 | 1.231968 | 4 | 8 | >64 | 0.33 | 5.91 | NT |
| V | >64 | >64 | 32 | 64 | >64 | NT | NT | 0.114 |

SEQUENCE LISTING

<160> NUMBER OF SEQ ID NOS: 1

<210> SEQ ID NO 1
<211> LENGTH: 2919
<212> TYPE: DNA
<213> ORGANISM: Mycobacterium tuberculosis

<400> SEQUENCE: 1

| | | | | | |
|---|---|---|---|---|---|
| catatgaccg | aaagcccgac | cgcaggtccg | ggtggtgtgc | cgcgtgcgga | tgatgcagat | 60 |
| agcgatgtgc | cgcgttatcg | ttataccgcg | gaactggcgg | cgcgtctgga | acgtacctgg | 120 |
| caggaaaact | gggcgcgtct | gggcaccttt | aacgtgccga | acccgtgggt | agcctggca | 180 |
| ccgccggatg | tgtcagcagt | gccggatgat | aaactgtttg | tgcaggatat | gtttccgtat | 240 |
| ccgagcggcg | aaggcctgca | tgtgggccat | ccgctgggct | atattgcgac | cgatgtgtat | 300 |
| gcgcgttatt | ttcgtatggt | gggccgtaac | gtgctgcatg | cgctgggctt | tgatgcgttt | 360 |
| ggtctgccgg | cggaacagta | tgcggtgcag | accggcaccc | atccgcgtac | ccgtaccgaa | 420 |
| gcgaacgtgg | tgaactttcg | tcgtcagctg | ggccgtctgg | gctttggcca | tgatagccgt | 480 |
| cgtagcttta | gcaccaccga | tgtggatttt | tatcgttgga | cccagtggat | ttttctgcag | 540 |
| atttataacg | cgtggtttga | taccaccgcg | aacaaagcgc | gtccgattag | cgaactggtg | 600 |
| gcggaatttg | aaagcggtgc | acgttgcctg | atggtggtc | gtgattgggc | aaaactgacc | 660 |
| gcaggtgaac | gtgcggatgt | gattgatgaa | tatcgtctgg | tgtatcgtgc | ggatagcctg | 720 |
| gtgaactggt | gcccgggtct | gggtaccgtg | ctggcaaacg | aagaagtgac | cgcagatggc | 780 |
| cgtagcgatc | gtggcaactt | ccggtgtttt | cgtaaacgtc | tgcgtcagtg | gatgatgcgt | 840 |
| attaccgcgt | atgcggatcg | tctgctggat | gatctggatg | tgctggattg | gccggaacag | 900 |
| gtgaaaacca | tgcagcgtaa | ctggattggc | cgtagcaccg | gcgcggtggc | gctgtttagc | 960 |
| gcgcgtgcgg | cgagcgatga | tggctttgaa | gtggatattg | aagtgtttac | cacccgtccg | 1020 |
| gatacectgt | ttggcgcgac | ctatctggtg | ctggcgccgg | aacatgatct | ggtggatgaa | 1080 |
| ctggtggcgc | aagctggcc | ggcaggtgtg | aacccgctgt | ggacctatgg | cggtggtacc | 1140 |
| ccgggtgaag | caattgcagc | atatcgtcgt | gcgattgcgg | cgaaaagcga | tctggaacgt | 1200 |
| caggaaagcc | gtgaaaaaac | cggcgtgttt | ctgggcagct | atgcgattaa | cccggcgaac | 1260 |
| ggcgaaccgg | tgccgatttt | tattgcggat | tatgtgctgg | cgggctatgg | caccggcgcg | 1320 |
| attatgcgg | tgccgggcca | tgatcagcgt | gattgggatt | ttgcgcgtgc | gtttggcctg | 1380 |
| ccgattgtgg | aagtgattgc | aggtggaaac | attagcgaaa | gcgcgtatac | cggcgatggc | 1440 |
| attctggtga | acagcgatta | tctgaacggc | atgagcgtgc | cggcagcaaa | acgtgcaatt | 1500 |
| gtggatcgtc | tggaaagcgc | aggtcgtggt | cgtgcacgta | ttgaatttaa | actgcgtgat | 1560 |
| tggctgtttg | cgcgtcagcg | ttattgggc | gaaccgttc | cgattgtgta | tgatagcgat | 1620 |
| ggccgtccgc | atgcgctgga | tgaagcggcg | ctgccggtgg | aactgccgga | tgtgccggat | 1680 |
| tatagcccgg | tgctgtttga | tccggatgat | gcggatagcg | aaccgagccc | gccgctggcg | 1740 |
| aaagcgaccg | aatgggtgca | tgtggatctg | gatctgggcg | atggcctgaa | accgtatagc | 1800 |
| cgtgatacca | acgtgatgcc | gcagtgggcg | ggcagcagct | ggtatgaact | gcgttatacc | 1860 |
| gatccgcata | acagcgaacg | tttttgcgcg | aaagaaaacg | aagcgtattg | gatgggtccg | 1920 |
| cgtccggcag | aacatggtcc | ggatgatccg | ggtggtgtgg | atctgtatgt | gggcggcgcg | 1980 |
| gaacatgcgg | tgctgcatct | gctgtatagc | cgttttggc | ataaagtgct | gtatgatctg | 2040 |
| ggccatgtga | gcagccgtga | accgtatcgt | cgtctggtga | accagggcta | tattcaggcg | 2100 |

```
tatgcgtata ccgatgcgcg tggcagctat gtgccggcgg aacaagtgat tgaacgtggc    2160
gatcgttttg tgtatccggg cccggatggc gaagtggaag tgtttcagga atttggcaaa    2220
attggcaaaa gcctgaaaaa cagcgtgagc ccggatgaaa tttgcgatgc gtatggcgcg    2280 gatacctgc gtgtgtatga aatgagcatg ggcccgctgg aagcgagccg tccgtgggcg     2340
accaaagatg tggtgggcgc gtatcgtttt ctgcagcgtg tgtggcgtct ggtggtggat    2400
gaacataccg gcgaaacccg tgtggcggat ggcgtggaac tggatattga taccctgcgt    2460
gcgctgcatc gtaccattgt gggcgtgagc gaagattttg cggcgctgcg taacaacacc    2520
gcgaccgcga aactgattga atataccaac catctgacca aaaaacatcg tgatgcagtg    2580
ccgcgtgcgg cagtggaacc gctggtgcag atgctggcac cgctggcacc gcatattgcg    2640
gaagaactgt ggctgcgtct gggcaacacc accagcctgg cgcatggccc gtttccgaaa    2700
gcggatgcgg cgtatctggt ggatgaaacc gtggaatatc cggtgcaggt gaacggcaaa    2760
gtgcgtggtc gtgtggtggt ggcggcggat accgatgaag aaaccctgaa agcggcggtg    2820
ctgaccgatg aaaaagtgca ggcgtttctg gcgggcgcga ccccgcgtaa agtgattgtg    2880
gtggcgggcc gtctggtgaa cctggtgatt taactcgag                           2919
```

BORON-CONTAINING SMALL MOLECULES

CROSS-REFERENCE TO RELATED APPLICATIONS

This application is a continuation of U.S. application Ser. No. 13/227,444, filed Sep. 7, 2011, now U.S. Pat. No. 8,703,742 issued on Apr. 22, 2014, and claims the benefit of U.S. Provisional Pat. App. No. 61/380,596, filed Sep. 7, 2010, which is incorporated by reference in its entirety for all purposes.

REFERENCE TO SEQUENCE LISTING SUBMITTED ELECTRONICALLY

The sequence listing contained in the file named "064507-5066-US_ST25.txt", created on Jan. 19, 2012 and having a size of 427 bytes, has been submitted electronically herewith via EFS-Web, and the contents of the txt file are hereby incorporated by reference in their entirety.

BACKGROUND OF THE INVENTION

The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antibiotics, useful in combating microorganisms, especially those with multidrug-resistance.

Boron-containing molecules, such as 1-hydroxy-1,3-dihydro-benzo[c][1,2]oxaborole (also sometimes known as 1-hydroxy-benzo[c][1,2]oxaborole or oxaboroles or cyclic boronic esters), useful as antimicrobials have been described previously, such as in U.S. patent application Ser. Nos. 12/142,692; 11/505,591 and 11/357,687. Generally speaking, a 1-hydroxy-1,3-dihydro-benzo[c][1,2]oxaborole has the following structure and substituent numbering system:

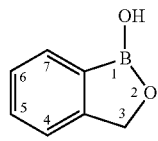

Surprisingly, it has now been discovered that certain classes of 1-hydroxy-1,3-dihydro-benzo[c][1,2]oxaboroles are effective antibacterials. This, and other uses of these 1-hydroxy-1,3-dihydro-benzo[c][1,2]oxaboroles are described herein.

SUMMARY OF THE INVENTION

In a first aspect, the invention provides a compound having a structure according to the formula:

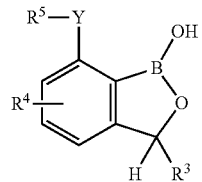

wherein $R^3$ is substituted or unsubstituted nitroalkyl or substituted or unsubstituted aminoalkyl; $R^4$ is selected from the group consisting of halogen, unsubstituted alkyl and unsubstituted phenyl; Y is O or S; $R^5$ is selected from the group consisting of substituted or unsubstituted alkyl and substituted or unsubstituted heteroalkyl, or a salt, hydrate or solvate thereof.

In a second aspect, the invention provides a combination comprising: a) a compound of the invention, or a pharmaceutically acceptable salt thereof; and b) a therapeutically active agent.

In a third aspect, the invention provides a pharmaceutical formulation comprising: a) a compound of the invention, or a pharmaceutically acceptable salt thereof; and b) a pharmaceutically acceptable excipient.

In a fourth aspect, the invention provides a method of killing or inhibiting the growth of a bacteria, said method comprising: contacting said bacteria with an effective amount of a compound of the invention or a combination of the invention, or a pharmaceutically acceptable salt thereof, thereby killing or inhibiting the growth of the bacteria.

In a fifth aspect, the invention provides a method of treating a bacterial infection comprising: administering to an animal suffering from said infection an effective amount of a compound of the invention, or a pharmaceutically-acceptable salt thereof, thereby treating the bacterial infection.

In a sixth aspect, the invention provides a method of inhibiting the editing domain of a t-RNA synthetase, comprising: contacting the synthetase with an effective amount of a compound of the invention, or a pharmaceutically-acceptable salt thereof, thereby inhibiting the synthetase.

BRIEF DESCRIPTION OF THE DRAWINGS

FIG. 1 displays biological data for exemplary compounds of the invention.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; Et$_2$O is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; K$_2$CO$_3$ is potassium carbonate; LiAlH$_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; MgSO$_4$ is magnesium sulfate; mins or min is minutes; Mp or MP is melting point; NaCNBH$_3$ is sodium cyanoborohydride; NaOH is sodium hydroxide; Na$_2$SO$_4$ is sodium sulfate; NBS is N-bromosuccinimide; NH$_4$Cl is ammonium chloride; NIS is N-iodosuccinimide; N$_2$ is nitrogen; NMM is N-methylmorpholine; n-BuLi is n-butyllithium; overnight is O/N; PdCl$_2$(pddf) is 1,1'-Bis (diphenylphosphino)ferrocene]dichloropalladium(II); Pd/C is the catalyst known as palladium on carbon; Pd$_2$(dba)$_3$ is an organometallic catalyst known as tris(dibenzylideneacetone)dipalladium(0); Ra Ni or Raney Ni is Raney nickel; Ph is phenyl; PMB is p-methoxybenzyl; PrOH is 1-propanol; iPrOH is 2-propanol; POCl$_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—NH$_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

The term "poly" as used herein means at least 2. For example, a polyvalent metal ion is a metal ion having a valency of at least 2.

"Moiety" refers to a radical of a molecule that is attached to the remainder of the molecule.

The symbol ∿, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkyl.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""' each preferably independently refer to hydrogen, substituted or unsubstituted heteroalkyl, substituted or unsubstituted aryl, e.g., aryl substituted with 1 or 2 or 3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 or 2 or 3 or 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers from 0 or 1 or 2 or 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$ or C$_2$ or C$_3$ or C$_4$ or C$_5$ or C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "excipients" is conventionally known to mean carriers, diluents and/or vehicles used in formulating drug compositions effective for the desired use.

The term "microbial infection" or "infection by a microorganism" refers to any infection of a host tissue by an infectious agent including, but not limited to, bacteria or protozoa (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of enzyme. In an exemplary embodiment, the enzyme is an editing domain of a tRNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium (such as choline or diethylamine or amino acids such as d-arginine, l-arginine, d-lysine or l-lysine) and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of salt counterions include $H^+$, $H_3O^+$, ammonium, potassium, calcium, magnesium (such as choline or diethylamine or amino acids such as d-arginine, l-arginine, d-lysine or l-lysine) and sodium. The salts of the compounds are implicitly contained in descriptions of these compounds.

II. Introduction

The invention provides novel boron compounds and methods for the preparation of these molecules. The invention further provides methods of treating bacterial infections, killing or inhibiting the growth of bacteria in part or wholly through the use of the compounds described herein. In another aspect, the invention is a combination of a compound of the invention and an antibiotic. In another aspect, the invention is a pharmaceutical formulation comprising a pharmaceutically acceptable excipient and a compound of the invention. In another aspect, the invention is a pharmaceutical formulation comprising a compound of the invention, an antibiotic, and a pharmaceutically acceptable excipient.

III. Composition of Matter

III. a.) Compounds

In one aspect the invention provides a compound of the invention. In an exemplary embodiment, the invention provides a compound described herein, or a salt thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

In an aspect, the invention provides a compound having a structure which is:

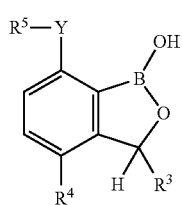

(I)

wherein R³ is substituted or unsubstituted nitroalkyl or substituted or unsubstituted aminoalkyl; R⁴ is selected from the group consisting of halogen, unsubstituted alkyl unsubstituted alkoxy and unsubstituted phenyl; Y is O or S; R⁵ is selected from the group consisting of substituted or unsubstituted alkyl and substituted or unsubstituted heteroalkyl; or a salt, hydrate or solvate thereof.

In an aspect, the invention provides a compound having a structure which is:

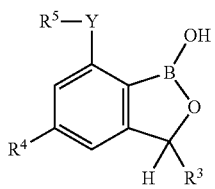

wherein R³ is substituted or unsubstituted nitroalkyl or substituted or unsubstituted aminoalkyl; R⁴ is selected from the group consisting of halogen, unsubstituted alkyl, unsubstituted alkoxy, and unsubstituted phenyl; Y is O or S; R⁵ is selected from the group consisting of substituted or unsubstituted alkyl and substituted or unsubstituted heteroalkyl; or a salt, hydrate or solvate thereof.

In an aspect, the invention provides a compound having a structure which is:

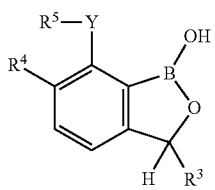

wherein R³ is substituted or unsubstituted nitroalkyl or substituted or unsubstituted aminoalkyl; R⁴ is selected from the group consisting of halogen, unsubstituted alkyl, unsubstituted alkoxy, and unsubstituted phenyl; Y is O or S; R⁵ is selected from the group consisting of substituted or unsubstituted alkyl and substituted or unsubstituted heteroalkyl; or a salt, hydrate or solvate thereof.

In an exemplary embodiment, there is provided a compound having a structure according to the following formula:

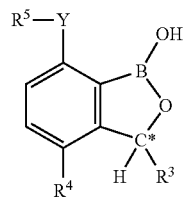

wherein C* is a carbon atom stereocenter which has a configuration which is (R) or (S). In an exemplary embodiment, the C* stereocenter is in the (S) configuration.

In an exemplary embodiment, there is provided a compound having a structure according to the following formula:

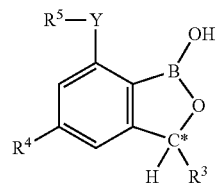

wherein C* is a carbon atom stereocenter which has a configuration which is (R) or (S). In an exemplary embodiment, the C* stereocenter is in the (S) configuration.

In an exemplary embodiment, there is provided a compound having a structure according to the following formula:

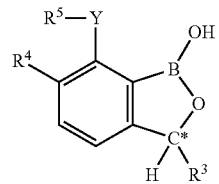

wherein C* is a carbon atom stereocenter which has a configuration which is (R) or (S). In an exemplary embodiment, the C* stereocenter is in the (S) configuration.

In an exemplary embodiment, Y, R⁵ and R⁴ are as described herein, R³ is —(CR²⁰R²¹)$_n$NR²²R²³ in which n is an integer selected from 1 to 10; each R²⁰ and each R²¹ is independently selected from the group consisting of H, R²⁶, OR²⁶, NR²⁶R²⁷SR²⁶, —S(O)R²⁶, —S(O)$_2$R²⁶, —S(O)$_2$NR²⁶R²⁷, —C(O)R²⁷, —C(O)OR²⁷, —C(O)NR²⁶R²⁷; R²² and R²³ are independently selected from the group consisting of H, —S(O)R²⁸, —S(O)$_2$R²⁸, —S(O)$_2$NR²⁸R²⁹, —C(O)R²⁸, —C(O)OR²⁸, —C(O)NR²⁸R²⁹, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein each R²⁶, each R²⁷, each R²⁸ and each R²⁹ is independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, Y, R⁵ and R⁴ are as described herein, and R³ is —CH$_2$NH$_2$ or —CH$_2$NO$_2$. In an exemplary embodiment, Y, $R^5$ and $R^4$ are as described herein, and $R^3$ is —$CH_2NH_2$. In an exemplary embodiment, Y, $R^5$ and $R^4$ are as described herein, $R^3$ is —$CH_2NH_2$, and C* has a configuration which is (S).

In an exemplary embodiment, Y, $R^5$ and $R^3$ are as described herein, and $R^4$ is selected from the group consisting of methyl, ethyl, propyl, isopropyl, butyl, isobutyl, and sec-butyl. In an exemplary embodiment, Y, $R^5$ and $R^3$ are as described herein, and $R^4$ is selected from the group consisting of fluorine, chlorine, bromine, and iodine. In an exemplary embodiment, Y, $R^5$ and $R^3$ are as described herein, and $R^4$ is chlorine or bromine. In an exemplary embodiment, Y, $R^5$ and $R^3$ are as described herein, and $R^4$ is chlorine.

In an exemplary embodiment, Y, $R^5$ and $R^3$ are as described herein, and $R^4$ is selected from the group consisting of methoxy, ethoxy, propoxy, isopropoxy, butoxy, isobutoxy, and sec-butoxy. In an exemplary embodiment, Y, $R^5$ and $R^3$ are as described herein, and $R^4$ is methoxy or ethoxy. In an exemplary embodiment, Y, $R^5$ and $R^3$ are as described herein, and $R^4$ is methoxy.

In an exemplary embodiment, Y, $R^4$ and $R^3$ are as described herein, and $R^5$ is:

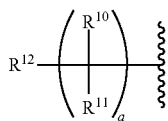

wherein a is 1, 2, 3, 4, 5, 6, 7, 8, 9, or 10; each $R^{10}$ and each $R^{11}$ is independently selected from the group consisting of H, substituted or unsubstituted alkyl, OH and $NH_2$; $R^{12}$ is selected from the group consisting of H, $R^7$, halogen, cyano, amidino, $OR^7$, $NR^7R^8$, $SR^7$, —$N(R^7)S(O)_2R^8$, —$C(O)R^7$, —$C(O)OR^7$, —$C(O)NR^7R^8$ wherein each $R^7$ and each $R^8$ is independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, Y, $R^4$, $R^3$, $R^{10}$, $R^{11}$, and $R^{12}$ are as described herein, and a is 1, 2, 3, 4, or 5. In an exemplary embodiment, Y, $R^4$, $R^3$, $R^{10}$, $R^{11}$, and $R^{12}$ are as described herein, and a is 2, 3, or 4. In an exemplary embodiment, Y, $R^4$, $R^3$, $R^{10}$, $R^{11}$, and $R^{12}$ are as described herein, and a is 3. In an exemplary embodiment, Y, $R^4$, $R^3$, a, and $R^{12}$ are as described herein, and each $R^{10}$ and each $R^{11}$ is independently selected from the group consisting of H, substituted or unsubstituted alkyl, OH, and $NH_2$. In an exemplary embodiment, Y, $R^4$, $R^3$, a, and $R^{12}$ are as described herein, and each $R^{10}$ and each $R^{11}$ is H. In an exemplary embodiment, Y, $R^4$, $R^3$, $R^{10}$, $R^{11}$, and a are as described herein, and $R^{12}$ is selected from the group consisting of H, OH, $NH_2$, methyl, ethyl, —$NHS(O)_2CH_3$, cyano, —$NHC(O)CH_3$, —$NHC(O)NHCH_2CH_3$, —$C(O)NH_2$, —$C(O)OH$, 4-(methoxy)phenyl, benzyl, benzoxy, —$NHC(O)OCH_2Ph$, —$C(O)NHCH_2CH_2OH$ and —$C(NH_2)(NH)$.

In an exemplary embodiment, $R^4$, $R^3$, and $R^5$ are as described herein, and Y is O. In an exemplary embodiment, $R^4$, $R^3$, and Y are as described herein, and $R^5$ is unsubstituted alkyl. In an exemplary embodiment, $R^4$, $R^3$, and Y are as described herein, and $R^5$ is selected from the group consisting of methyl, ethyl, propyl, isopropyl, butyl, isobutyl, t-butyl, and sec-butyl.

In an exemplary embodiment, $R^4$ is halogen, $R^3$ is —$CH_2NH_2$; Y is O; and $R^5$ is selected from the group consisting of methyl, ethyl, propyl, isopropyl, butyl, isobutyl, t-butyl, and sec-butyl. In an exemplary embodiment, $R^4$ is halogen, $R^3$ is —$CH_2NH_2$; Y is O; and $R^5$ is selected from the group consisting of methyl, ethyl, propyl, and isopropyl. In an exemplary embodiment, $R^4$ is halogen, $R^3$ is —$CH_2NH_2$; Y is O; and $R^5$ is selected from the group consisting of butyl, isobutyl, t-butyl, and sec-butyl.

In an exemplary embodiment, $R^4$ is chlorine, $R^3$ is —$CH_2NH_2$; Y is O; and $R^5$ is selected from the group consisting of methyl, ethyl, propyl, and isopropyl. In an exemplary embodiment, $R^4$ is chlorine, $R^3$ is —$CH_2NH_2$; Y is O; and $R^5$ is selected from the group consisting of butyl, isobutyl, t-butyl, and sec-butyl.

In an exemplary embodiment, $R^4$ is fluorine, $R^3$ is —$CH_2NH_2$; Y is O; and $R^5$ is selected from the group consisting of methyl, ethyl, propyl, and isopropyl. In an exemplary embodiment, $R^4$ is fluorine, $R^3$ is —$CH_2NH_2$; Y is O; and $R^5$ is selected from the group consisting of butyl, isobutyl, t-butyl, and sec-butyl.

In an exemplary embodiment, $R^4$ is bromine, $R^3$ is —$CH_2NH_2$; Y is O; and $R^5$ is selected from the group consisting of methyl, ethyl, propyl, and isopropyl. In an exemplary embodiment, $R^4$ is bromine, $R^3$ is —$CH_2NH_2$; Y is O; and $R^5$ is selected from the group consisting of butyl, isobutyl, t-butyl, and sec-butyl.

In an exemplary embodiment, $R^4$ is halogen, $R^3$ is —$CH_2NH_2$; Y is O; and $R^5$ is methyl. In an exemplary embodiment, $R^4$ is fluorine, $R^3$ is —$CH_2NH_2$; Y is O; and $R^5$ is methyl. In an exemplary embodiment, $R^4$ is chlorine, $R^3$ is —$CH_2NH_2$; Y is O; and $R^5$ is methyl. In an exemplary embodiment, $R^4$ is bromine, $R^3$ is —$CH_2NH_2$; Y is O; and $R^5$ is methyl.

In an exemplary embodiment, $R^4$ is halogen, $R^3$ is —$CH_2NH_2$; Y is O; and $R^5$ is ethyl. In an exemplary embodiment, $R^4$ is fluorine, $R^3$ is —$CH_2NH_2$; Y is O; and $R^5$ is ethyl. In an exemplary embodiment, $R^4$ is chlorine, $R^3$ is —$CH_2NH_2$; Y is O; and $R^5$ is ethyl. In an exemplary embodiment, $R^4$ is bromine, $R^3$ is —$CH_2NH_2$; Y is O; and $R^5$ is ethyl.

In an exemplary embodiment, $R^4$ is halogen, $R^3$ is —$CH_2NH_2$; Y is O; and $R^5$ is propyl. In an exemplary embodiment, $R^4$ is fluorine, $R^3$ is —$CH_2NH_2$; Y is O; and $R^5$ is propyl. In an exemplary embodiment, $R^4$ is chlorine, $R^3$ is —$CH_2NH_2$; Y is O; and $R^5$ is propyl. In an exemplary embodiment, $R^4$ is bromine, $R^3$ is —$CH_2NH_2$; Y is O; and $R^5$ is propyl.

In an exemplary embodiment, $R^4$ is halogen, $R^3$ is —$CH_2NH_2$; Y is O; and $R^5$ is isopropyl. In an exemplary embodiment, $R^4$ is fluorine, $R^3$ is —$CH_2NH_2$; Y is O; and $R^5$ is isopropyl. In an exemplary embodiment, $R^4$ is chlorine, $R^3$ is —$CH_2NH_2$; Y is O; and $R^5$ is isopropyl. In an exemplary embodiment, $R^4$ is bromine, $R^3$ is —$CH_2NH_2$; Y is O; and $R^5$ is isopropyl.

In an exemplary embodiment, $R^4$ is halogen, $R^3$ is —$CH_2NH_2$; Y is O; and $R^5$ is unsubstituted $C_4$ alkyl. In an exemplary embodiment, $R^4$ is fluorine, $R^3$ is —$CH_2NH_2$; Y is O; and $R^5$ is unsubstituted $C_4$ alkyl. In an exemplary embodiment, $R^4$ is chlorine, $R^3$ is —$CH_2NH_2$; Y is O; and $R^5$ is unsubstituted $C_4$ alkyl. In an exemplary embodiment, $R^4$ is bromine, $R^3$ is —$CH_2NH_2$; Y is O; and $R^5$ is unsubstituted $C_4$ alkyl.

In an exemplary embodiment, $R^4$ is halogen, $R^3$ is —$CH_2NH_2$; Y is O; and $R^5$ is unsubstituted $C_5$ alkyl. In an exemplary embodiment, $R^4$ is fluorine, $R^3$ is —$CH_2NH_2$; Y is O; and $R^5$ is unsubstituted $C_5$ alkyl. In an exemplary embodiment, R⁴ is chlorine, R³ is —CH₂NH₂; Y is O; and R⁵ is unsubstituted C₅ alkyl. In an exemplary embodiment, R⁴ is bromine, R³ is —CH₂NH₂; Y is O; and R⁵ is unsubstituted C₅ alkyl.

In an exemplary embodiment, R⁴ is halogen, R³ is —CH₂NH₂; Y is O; and R⁵ is unsubstituted C₆ alkyl. In an exemplary embodiment, R⁴ is fluorine, R³ is —CH₂NH₂; Y is O; and R⁵ is unsubstituted C₆ alkyl. In an exemplary embodiment, R⁴ is chlorine, R³ is —CH₂NH₂; Y is O; and R⁵ is unsubstituted C₆ alkyl. In an exemplary embodiment, R⁴ is bromine, R³ is —CH₂NH₂; Y is O; and R⁵ is unsubstituted C₆ alkyl.

In an exemplary embodiment, R⁴ is chlorine, R³ is —CH₂NH₂; Y is O; and R⁵ is selected from the group consisting of methyl, ethyl, propyl, and isopropyl. In an exemplary embodiment, R⁴ is chlorine, R³ is —CH₂NH₂; Y is O; and R⁵ is selected from the group consisting of butyl, isobutyl, t-butyl, and sec-butyl.

In an exemplary embodiment, R⁴ is fluorine, R³ is —CH₂NH₂; Y is O; and R⁵ is selected from the group consisting of methyl, ethyl, propyl, and isopropyl. In an exemplary embodiment, R⁴ is fluorine, R³ is —CH₂NH₂; Y is O; and R⁵ is selected from the group consisting of butyl, isobutyl, t-butyl, and sec-butyl.

In an exemplary embodiment, R⁴ is bromine, R³ is —CH₂NH₂; Y is O; and R⁵ is selected from the group consisting of methyl, ethyl, propyl, and isopropyl. In an exemplary embodiment, R⁴ is bromine, R³ is —CH₂NH₂; Y is O; and R⁵ is selected from the group consisting of butyl, isobutyl, t-butyl, and sec-butyl.

In an exemplary embodiment, R⁴ is as described herein, R³ is —CH₂NH₂; Y is O; and R⁵ is substituted or unsubstituted alkyl. In an exemplary embodiment, Y and R⁵ are as described herein, R³ is —CH₂NH₂; and R⁴ is halogen. In an exemplary embodiment, Y is as described herein, R⁴ is halogen; Y is O; and R⁵ is unsubstituted alkyl. In an exemplary embodiment, R³ is —CH₂NH₂; R⁴ is chlorine; Y is O; and R⁵ is substituted or unsubstituted alkyl. In an exemplary embodiment, R⁴ is as described herein, R³ is —CH₂NH₂; Y is O; and R⁵ is ethyl.

In an exemplary embodiment, the compound has a structure which is

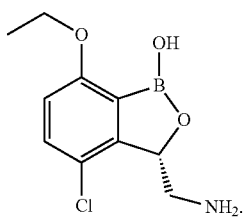 [SMILES: CCOc1ccc(Cl)c2c1B(O)O[C@@H]2CN]

In an exemplary embodiment, the compound has a structure which is

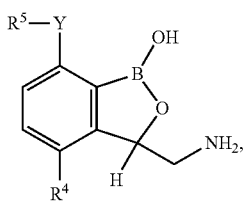

wherein R⁴, Y and R⁵ are as described herein.

In an exemplary embodiment, the compound has a structure which is

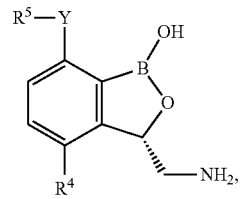

wherein R⁴, Y and R⁵ are as described herein. In an exemplary embodiment, Y is O, and R⁴ and R⁵ are as described herein. In an exemplary embodiment, Y is O, R⁴ is halogen, and R⁵ are as described herein. In an exemplary embodiment, Y is O, R⁴ is halogen, and R⁵ is unsubstituted alkyl. In an exemplary embodiment, Y is O, R⁴ is halogen, and R⁵ is methyl or ethyl or propyl or isopropyl. In an exemplary embodiment, Y is O, R⁴ is halogen, and R⁵ is butyl or isobutyl or neobutyl or t-butyl.

In an exemplary embodiment, the compound has a structure which is

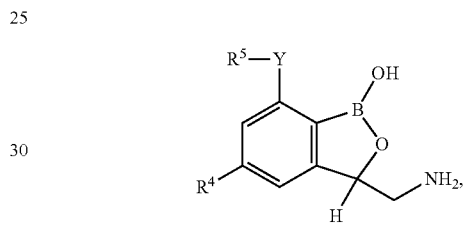

wherein R⁴, Y and R⁵ are as described herein.

In an exemplary embodiment, the compound has a structure which is

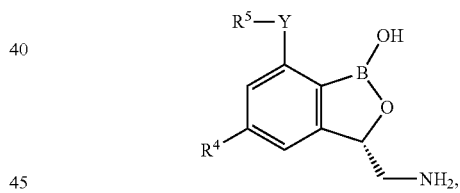

wherein R⁴, Y and R⁵ are as described herein. In an exemplary embodiment, Y is O, and R⁴ and R⁵ are as described herein. In an exemplary embodiment, Y is O, R⁴ is halogen, and R⁵ are as described herein. In an exemplary embodiment, Y is O, R⁴ is halogen, and R⁵ is unsubstituted alkyl. In an exemplary embodiment, Y is O, R⁴ is halogen, and R⁵ is methyl or ethyl or propyl or isopropyl. In an exemplary embodiment, Y is O, R⁴ is halogen, and R⁵ is butyl or isobutyl or neobutyl or t-butyl.

In an exemplary embodiment, the compound has a structure which is

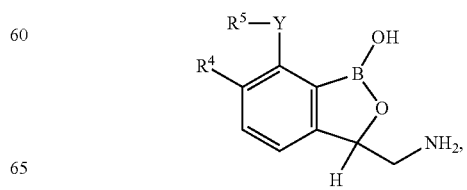

wherein R⁴, Y and R⁵ are as described herein.

In an exemplary embodiment, the compound has a structure which is

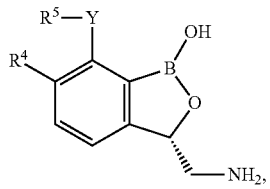

wherein $R^4$, Y and $R^5$ are as described herein. In an exemplary embodiment, Y is O, and $R^4$ and $R^5$ are as described herein. In an exemplary embodiment, Y is O, $R^4$ is halogen, and $R^5$ are as described herein. In an exemplary embodiment, Y is O, $R^4$ is halogen, and $R^5$ is unsubstituted alkyl. In an exemplary embodiment, Y is O, $R^4$ is halogen, and $R^5$ is methyl or ethyl or propyl or isopropyl. In an exemplary embodiment, Y is O, $R^4$ is halogen, and $R^5$ is butyl or isobutyl or neobutyl or t-butyl.

In an exemplary embodiment, said alkyl is linear alkyl or branched alkyl, In an exemplary embodiment, said heteroalkyl is linear heteroalkyl or branched heteroalkyl.

In an exemplary embodiment, the invention provides poly- or multi-valent species of the compounds of the invention, including a dimer or a trimer. Another exemplary embodiment of the invention provides an anhydride of the compounds of the invention. In another exemplary embodiment, the invention provides poly- or multi-valent species of the compounds of the invention. In an exemplary embodiment, the invention provides a dimer of the compounds described herein. In an exemplary embodiment, the invention provides a dimer of the compounds described herein.

In an exemplary embodiment, the invention provides an anhydride of the compounds described herein. In an exemplary embodiment, the invention provides an anhydride of the compounds described herein.

In an exemplary embodiment, the invention provides a trimer of the compounds described herein. In an exemplary embodiment, the invention provides a trimer of the compounds described herein.

The compounds of the invention can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein. In an exemplary embodiment, the invention provides a compound as described in FIG. 1, or a salt thereof. In an exemplary embodiment, the invention provides a compound as described in FIG. 1, or a pharmaceutically acceptable salt thereof.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent, or a salt, prodrug, hydrate or solvate thereof. In an exemplary embodiment, the compound of the invention is a compound described herein, or a salt thereof. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in sections III a) or b).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

In an exemplary embodiment, the additional therapeutic agent is an antibacterial agent. In an exemplary embodiment, the additional therapeutic agent is an antituberculosis agent. In an exemplary embodiment, the additional therapeutic agent is rifampicin. In an exemplary embodiment, the additional therapeutic agent is isoniazid. In an exemplary embodiment, the additional therapeutic agent is pyrazinamide. In an exemplary embodiment, the additional therapeutic agent is ethambutol. In an exemplary embodiment, the additional therapeutic agent is isoniazid. In an exemplary embodiment, the additional therapeutic agent is streptomycin. In an exemplary embodiment, the additional therapeutic agent is an aminoglycoside. In an exemplary embodiment, the additional therapeutic agent is amikacin or kanamycin. In an exemplary embodiment, the additional therapeutic agent is a polypeptide. In an exemplary embodiment, the additional therapeutic agent is selected from the group consisting of capreomycin, viomycin, and enviomycin. In an exemplary embodiment, the additional therapeutic agent is a fluoroquinolone. In an exemplary embodiment, the additional therapeutic agent is selected from the group consisting of ciprofloxacin, levofloxacin, and moxifloxacin. In an exemplary embodiment, the additional therapeutic agent is a thioamide. In an exemplary embodiment, the additional therapeutic agent is ethionamide or prothionamide. In an exemplary embodiment, the additional therapeutic agent is cycloserine. In an exemplary embodiment, the additional therapeutic agent is p-aminosalicylic acid. In an exemplary embodiment, the additional therapeutic agent is selected from the group consisting of rifabutin, linezolid, thioacetazone, thioridazine, arginine, vitamin D, and R207910. In an exemplary embodiment, the additional therapeutic agent is a macrolide.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (for example, a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a single unit dosage form which includes a compound of the invention; an antibiotic and a pharmaceutically acceptable excipient. In an exemplary embodiment, the pharmaceutical formulation is a single unit dosage form which includes a compound of the invention; an antibiotic and at least one pharmaceutically acceptable excipient. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an antibiotic and d) a second pharmaceutically acceptable excipient.

III. c) Preparation of Boron-Containing Compounds

Compounds of use in the invention can be prepared using commercially available starting materials, known intermediates, or by using the synthetic methods published in references described and incorporated by reference herein, such as U.S. patent application Ser. No. 12/142,692 and U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues.

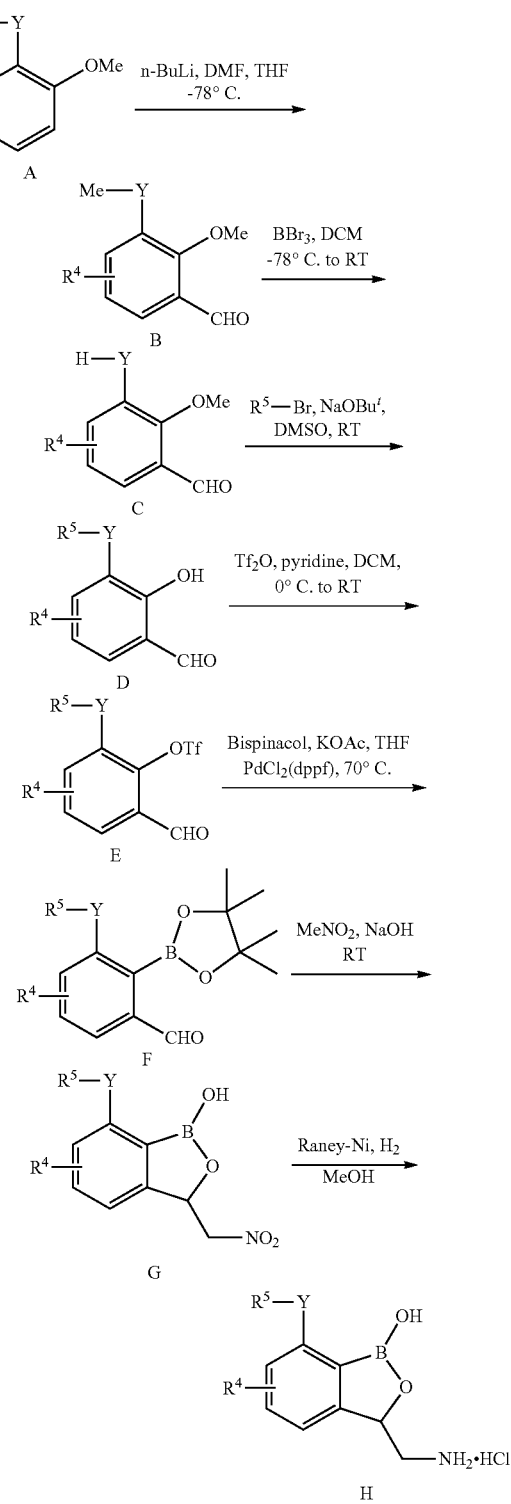

Scheme 1 describes a synthesis for compounds of (I), wherein $R^4$ is fluorine or chlorine and Y and $R^5$ are as described herein. The fluoro or chloro compound of formula A, which may be prepared or maybe available commercially from Sigma-Aldrich, is reacted with a strong base (such as n-BuLi, sec-BuLi, or t-BuLi, 2 equiv) followed by quenching with a formylating agent (such as DMF, dimethylformamide, formanilide, N-formylmorpholine, large excess) to give the compound of formula B. Treatment of compound B with a demethylating agent (typically $BBr_3$, 2 equiv) in a suitable solvent (dichloromethane, THF) gives the phenol of formula C. Compound C can react with a corresponding bromide or mesylate (1-1.5 equiv) in the presence of a base (such as KOtBu, $K_2CO_3$, or $Cs_2CO_3$, 1.5-2 equiv) in an aprotic solvent such as DMF or DMSO to afford the compound of formula D. Compound D may be converted to triflate E by the reaction with 1.2 equiv of trifluoromethanesulfonic anhydride and pyridine in dichloromethane. The conversion of triflate E to boronate F can be achieved by the reaction with bis(pinacolato)diborane (2 equiv), KOAc (3 equiv) and catalytic amount of $PdCl_2$(dppf) (4-8 mol %). The reaction of compound F with nitromethane (3 equiv) in the presence of sodium hydroxide (3 equiv) in water or THF gives the nitro compound of formula G. The compound G can be converted to the final product of formula H by the Raney-Ni reduction (Raney Ni, 2 equiv w/w, 2.0 M $NH_3$ in EtOH, absolute EtOH).

General reaction scheme 2

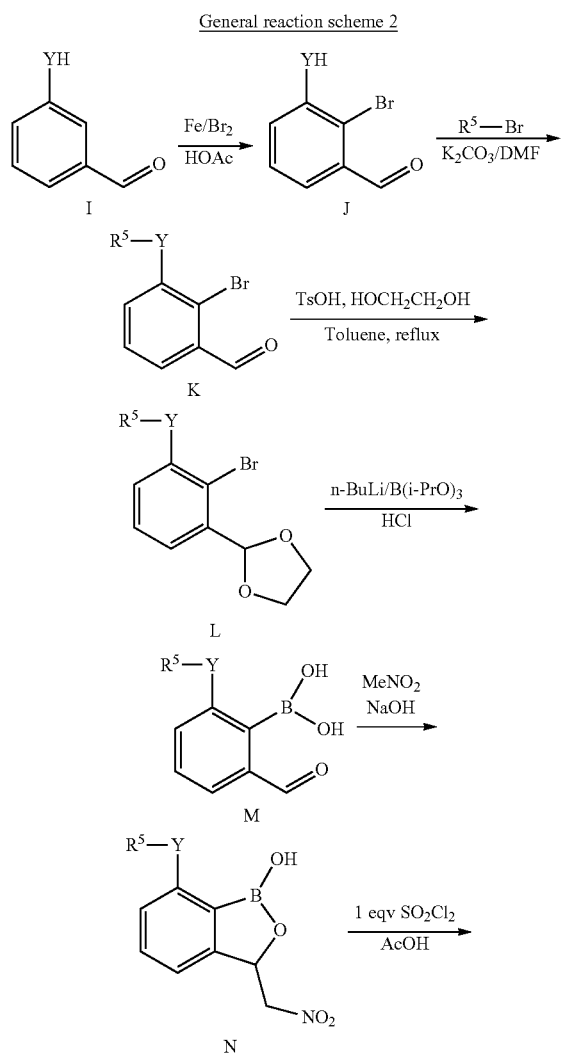

Scheme 2 describes a synthesis for compounds of (I), wherein $R^4$ is chlorine, Y and $R^5$ are as described herein. The phenol or thiophenol of formula I, which may be prepared or maybe available commercially from Sigma-Aldrich, react with a solution of bromine and catalytic amount of iron powder in glacial acetic acid to give the bromo substituted compound of formula J. The alkylation of J can be achieved by reacting with a bromide in the presence of a base such as potassium carbonate in solvents like DMF or acetonitrile. The protection of aldehyde K may be achieved by refluxing with ethylene glycol in toluene, in the presence of catalytic amount of p-toluenesulfonic acid. The reaction of the compound L with BuLi and triisopropyl borate, followed by treating with hydrochloric acid yields boronic acid M. The reaction of compound M with nitromethane in the presence of sodium hydroxide gives the nitro compound of formula N. The treatment of N with 1 equivalent of sulfuryl chloride affords the chloro substituted compound O. The Raney-Ni reduction of compound O in MeOH gives the final product of formula P.

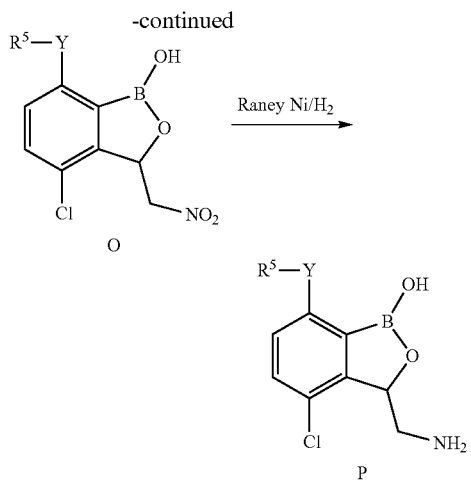

General reaction scheme 3

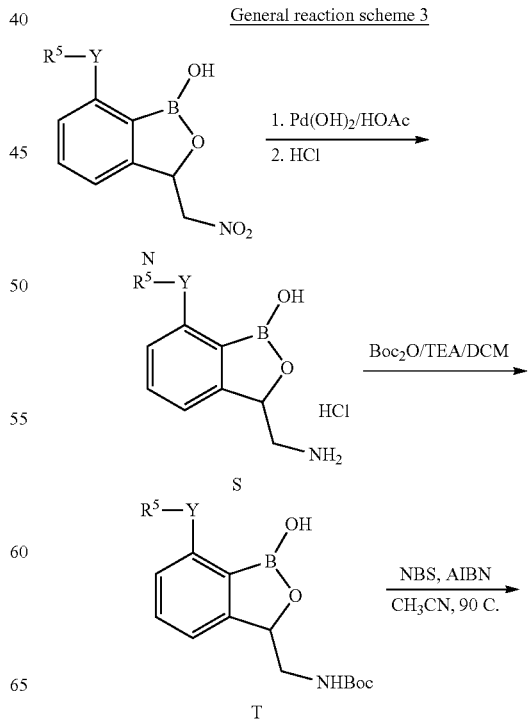

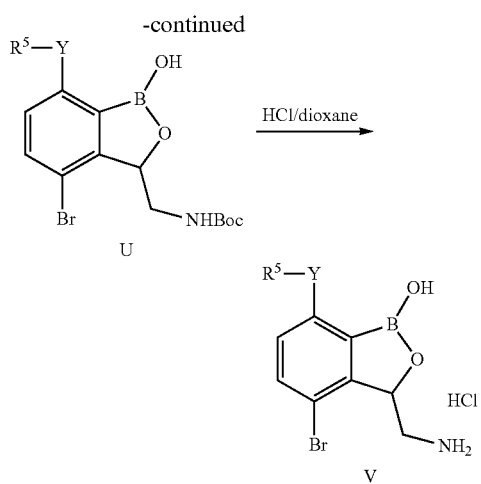

Scheme 3 describes a synthesis for compounds of (I), wherein $R^4$ is bromine, Y and $R^5$ are as described herein. The compound of formula N, which may be prepared according to Scheme 2, can be reduced to the amine of formula S, by hydrogenation in the presence of palladium hydroxide or Raney-Ni reduction as described above. The amine of formula S reacts with an N-Protecting reagent such as Boc anhydride in the presence of base like triethylamine in dichloromethane to give Boc-protected compound of formula T. The treatment of T with N-bromosuccinimide and catalytic amount of AIBN in acetonitrile gives the bromo substituted compound of formula U. Deprotection of compound U in the presence of acid such as HCl in dioxane will afford the final compound of formula U.

General reaction scheme 4

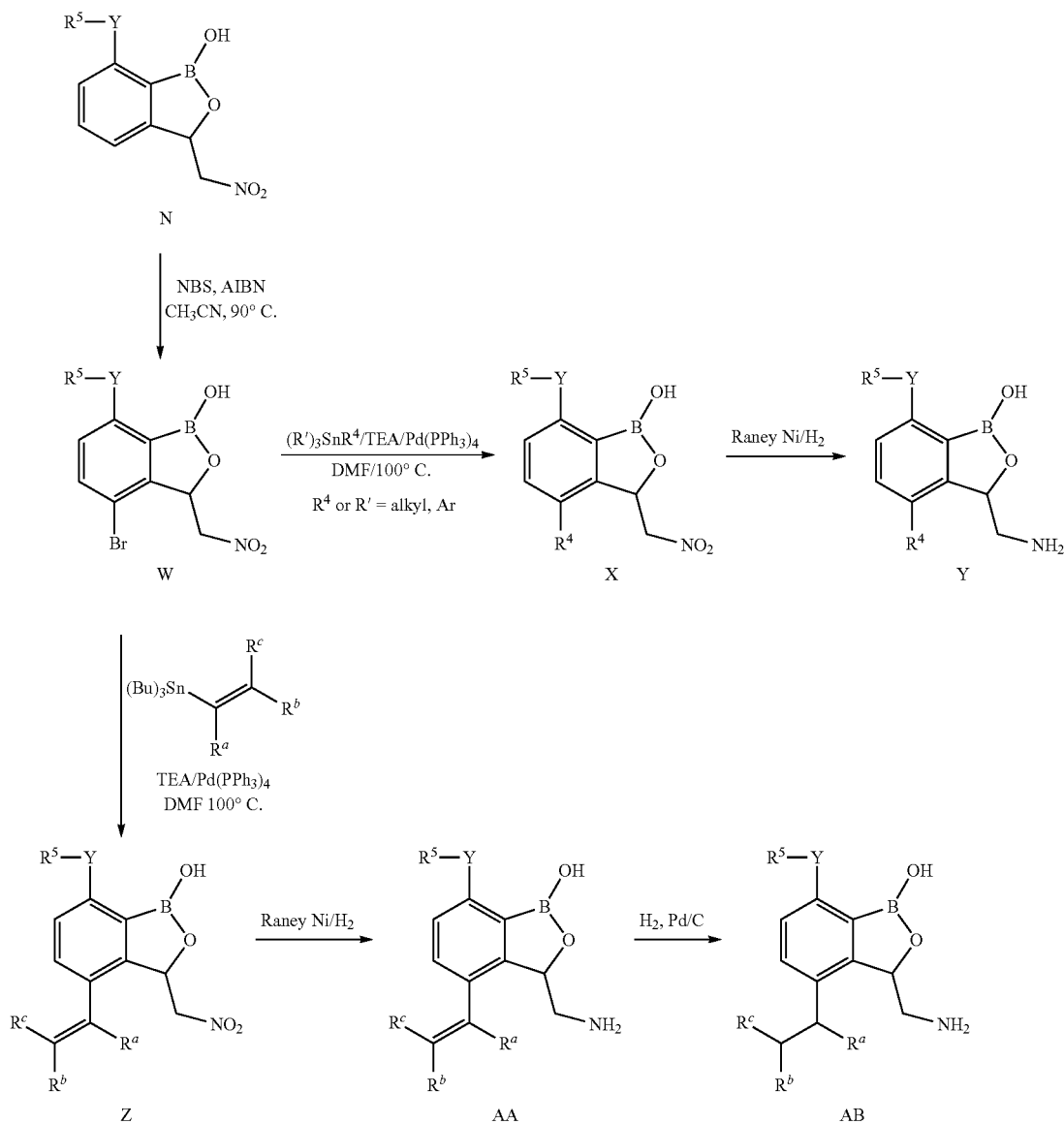

Scheme 4 describes a synthesis for compounds of (I), wherein $R^4$ is an alkyl or aryl group, Y and $R^5$ are as described herein. The compound of formula N, which may be prepared according to Scheme 2, can be brominated with N-bromosuccinimide and catalytic amount of AIBN in a solvent such as acetonitrile to give the bromide of formula W. Stille coupling of W with an organotin compound such as tetramethylstannane or tributyl-phenyl-stannane in the presence of catalytic $Pd(Ph_3P)_4$ in DMF affords the compound of formula X. Compound X can be reduced to the final compound of formula Y by hydrogenation in the presence of palladium on carbon or Raney-Ni reduction as described above. Alternatively, Stille reaction of W with an organotin compound such as vinyltributyltin in the presence of catalytic amount of $Pd(Ph_3P)_4$ in DMF affords the compound of formula Z. After Raney-Ni reduction of compound Z, further hydrogenation in the presence of palladium on carbon as described above will afford the final compound of formula AB.

Scheme 5 describes a method to separate compounds (1) into their enantiomeric isomers, wherein $R^4$, Y, and $R^5$ are as described herein. The compound of formula AC, which may be prepared according to Scheme 1 or Scheme 2 or Scheme 3 or Scheme 4, can be converted to the Boc-protected compound AD by the reaction with an N-Protecting reagent such as Boc anhydride in the presence of base like triethylamine in dichloromethane. Racemic compound AD can be resolved via chiral HPLC using a chiral column such as ChiralPak AD-H and SF $CO_2$/methanol as eluent. Two compounds collected are enantiomer AE and enantiomer AF. Analysis of the enantiomeric purity of each isomer can be achieved using a chiral column such as ChiralPak AD column. The Boc-protected compounds AE and AF can be converted to the final chiral compounds AG and AH, by deprotection using acid such as HCl in dioxane.

General reaction scheme 5: Chiral separation

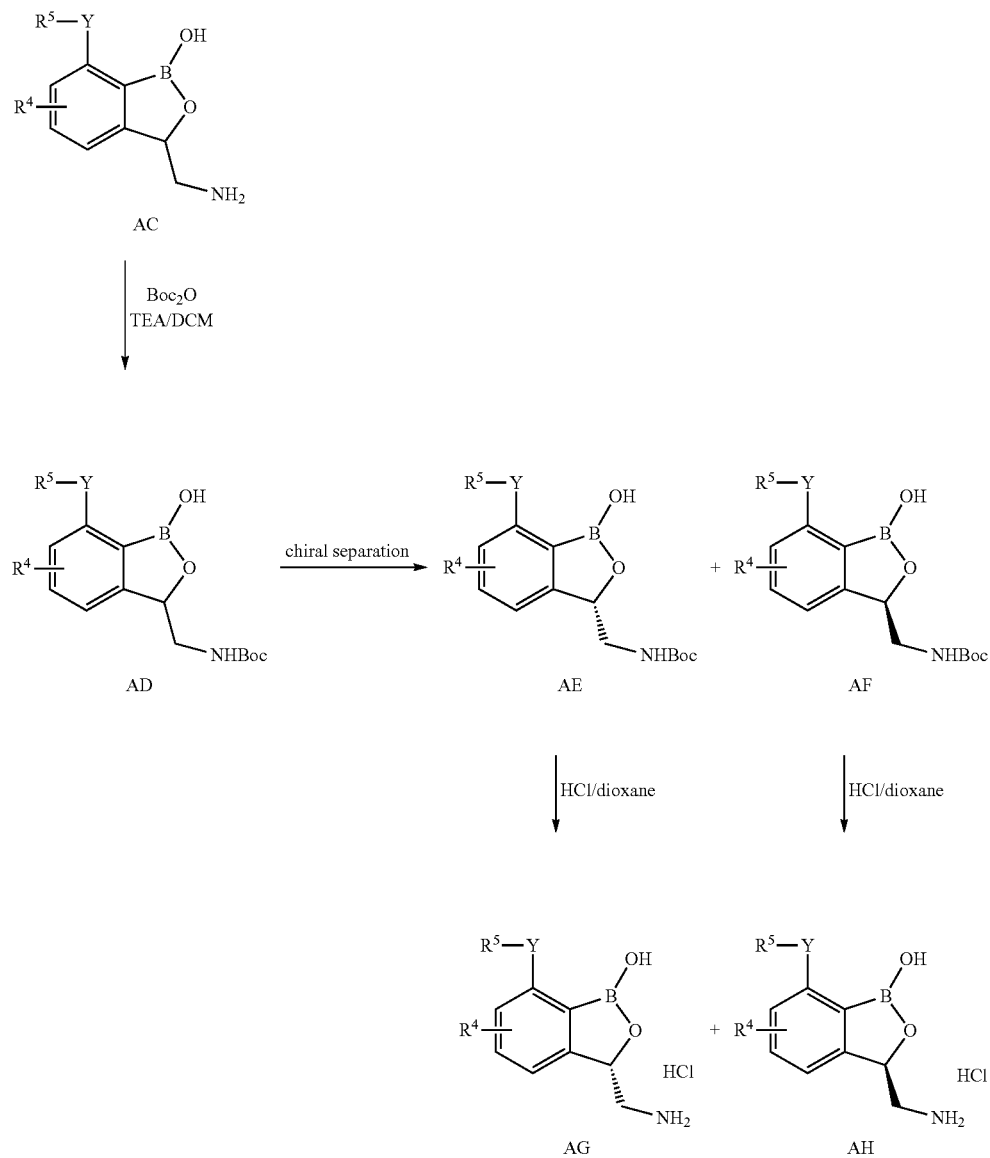

General reaction scheme 6: Chiral separation

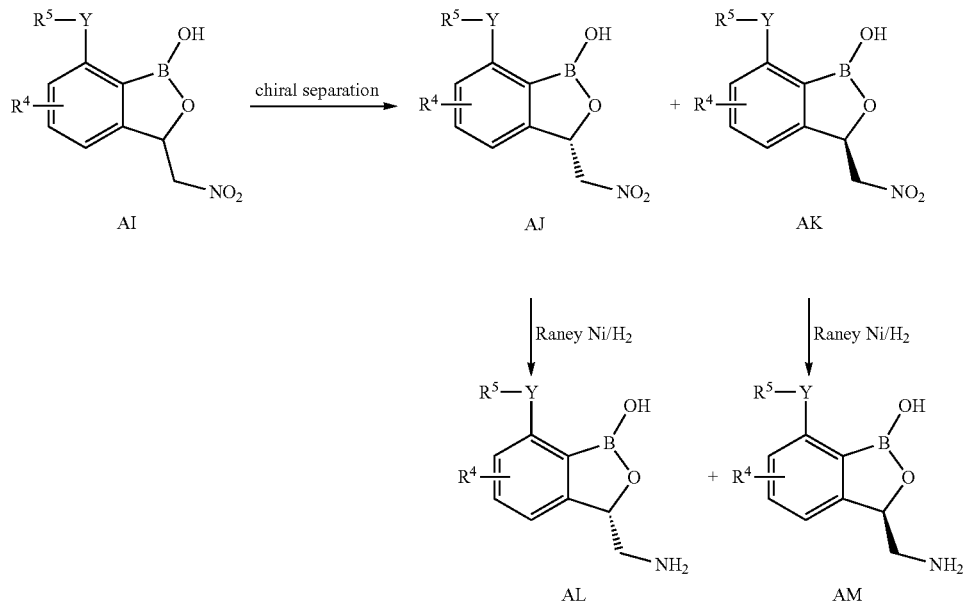

Scheme 6 describes an alternative method to separate chiral compounds AI into their enantiomeric isomers, wherein $R^4$, Y, and $R^5$ are as described herein. The compound of formula AI may be prepared according to Scheme 1 or Scheme 2 or Scheme 3 or Scheme 4. The separation of the two enantiomers was achieved by dissolving the racemic material AI in a suitable solvent and applying to an appropriate chiral column and eluent system. The collected separated enantiomer samples were then concentrated and used in the next step without further purification. Using this technique, it is possible to achieve a range of enantiomeric excesses of the separated enantiomers. The nitro compound AJ and AK can be converted to the final chiral compounds AL and AM, respectively, by Raney-Ni reduction (Raney Ni, 2 equiv w/w, 2.0 M $NH_3$ in EtOH, absolute EtOH).

IV. Assays

Art-recognized techniques of genetics and molecular biology are of use to identify compounds that bind to and/or inhibit an enzyme, such as a tRNA synthetase. Moreover, these techniques are of use to distinguish whether a compound binds to and/or inhibits a particular domain of the enzyme. For example, for leucyl tRNA synthetase (LeuRS), these techniques can distinguish whether a compound binds to and/or inhibits the synthetic domain, the editing domain, or both the editing and synthetic domains. The *Mycobacterium tuberculosis* leuS gene was synthesized by Genscript (Piscataway, N.J.) using *E. coli* optimized codons and protein was made using standard T7 RNA polymerase over-expression protocols and standard purification protocols.

IV. a) LeuRS

In an exemplary assay, activity of a representative compound against the editing domain was confirmed. To identify the target of a novel boron-containing antibacterial compound, mutants in *E. coli* showing resistance to the compound were isolated. Characterization of mutants showed that they have an 32-256 fold increase in resistance to the compound over wildtype. The mutants were furthermore shown to be sensitive to various antibacterial agents with known modes of action, suggesting that the cellular target of the compound is distinct from the target of the other antibacterial agents. The leuS gene from the mutants was cloned onto a plasmid and their resistance was confirmed by MIC. The editing domain from these mutants were sequenced and the mutations were all located in the editing domain of this enzyme.

Assays to determine whether, and how effectively, a particular compound binds to and/or inhibits the editing domain of a selected tRNA synthetase are also set forth herein, and additional assays are readily available to those of skill in the art. Briefly, in an exemplary assay, an improperly charged tRNA and a tRNA synthetase that is capable of editing the improperly charged tRNA are combined. The resulting mixture is contacted with the putative inhibitor and the degree of editing inhibition is observed.

Another assay uses genetics to show that a drug works via the editing domain. In this assay, the compound is first tested against a strain of cells over-expressing copies of the tRNA synthetase gene. The compound's effect on the over-expressing strain is compared with a control strain to determine whether the compound is active against the synthetase. If the minimum inhibitory concentration (MIC) is 2-fold higher in the strain with extra copies of the synthetase gene than the MIC of the inhibitor against a wild type cell, a further genetic screen is conducted to determine whether the increased resistance is due to mutations in the editing domain. In this second screen, the control strain is challenged against a high concentration of the inhibitor. The colonies surviving the challenge are isolated and DNA from these cells is isolated. The editing domain is amplified using a proof-reading PCR enzyme and the appropriate primers. The PCR product can be purified using standard procedures. The sequence amplified mutant DNA is compared to wild-type. If the mutant DNA bears mutations in the editing domain, such results would suggest that the compound binds to the editing domain and affects the editing function of the molecule through this domain.

Generally, the compounds to be tested are present in the assays in ranges from about 1 pM to about 100 mM, preferably from about 1 pM to about 1 µM. Other compounds range from about 1 nM to about 100 nM, preferably from about 1 nM to about 1 µM.

The effects of the test compounds upon the function of the enzymes can also be measured by any suitable physiological change. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

Utilizing the assays set forth herein and others readily available in the art, those of skill in the art will be able to readily and routinely determine other compounds and classes of compounds that operate to bind to and/or inhibit the editing domain of tRNA synthetases.

In another aspect, the invention provides a method for identifying a compound which binds to an editing domain of a tRNA synthetase comprising: a) contacting said editing domain with a test compound under conditions suitable for binding; and b) detecting binding of said test compound to said editing domain. In an exemplary embodiment, detecting binding of said compound comprises use of at least one detectable element, isotope, or chemical label attached to said compound. In an exemplary embodiment, the element, isotope or chemical label is detected by a fluorescent, luminescent, radioactive, or absorbance readout. In an exemplary embodiment, the contacting of said test compound with said editing domain also includes further contacting said test compound and said editing domain with a member selected from AMP and a molecule with a terminal adenosine. In an exemplary embodiment, the tRNA synthetase is derived from leucyl tRNA synthetase. In an exemplary embodiment, the tRNA synthetase is derived from a mutated tRNA synthetase, wherein said mutated tRNA synthetase comprises amino acid mutations in an editing domain. In another exemplary embodiment, wherein said editing domain of a tRNA synthetase comprises the amino acid sequence of a peptide sequence described herein.

In another aspect, the invention provides a method for identifying a compound which binds to an editing domain of a tRNA synthetase, said assay comprising: a) contacting said editing domain of a tRNA synthetase with said compound under conditions suitable for binding of said compound with said editing domain of a tRNA synthetase; b) comparing a biological activity of said editing domain of a tRNA synthetase contacting said compound to said biological activity when not contacting said compound; and c) identifying said compound as binding to said editing domain of a tRNA synthetase if said biological activity of said editing domain of a tRNA synthetase is reduced when contacting said compound. In an exemplary embodiment, the biological activity is hydrolysis of noncognate amino acid. In another exemplary embodiment, the hydrolysis of said noncognate amino acid is detected through the use of one or more labels. In another exemplary embodiment, the labels include a radiolabel, a fluorescent marker, an antibody, or a combination thereof. In another exemplary embodiment, said labels can be detected using spectroscopy. In another exemplary embodiment, said editing domain of a tRNA synthetase is derived from leucyl tRNA synthetase.

In another aspect, the invention provides a method of generating a tRNA molecule with a noncognate amino acid comprising: a) creating or isolating a mutated tRNA synthetase with altered amino acid editing domains; and b) contacting a tRNA molecule with said mutated tRNA synthetase and a noncognate amino acid. In another exemplary embodiment, the mutated tRNA synthetase contains one or more amino acid mutations in an editing domain. In another exemplary embodiment, the mutated tRNA synthetase is unable to bind with a compound of the invention. In another exemplary embodiment, the mutated tRNA synthetase is unable to bind with a compound described herein, or a pharmaceutically acceptable salt thereof. In another exemplary embodiment, the mutated tRNA synthetase is unable to bind with a compound according to a formula described herein, or a pharmaceutically acceptable salt thereof.

In another aspect, the invention provides a composition that comprises one or more tRNA molecules attached to noncognate amino acids, wherein said tRNA molecules are synthesized using one or more mutated tRNA synthetases isolated from a microorganism or a cell line derived from a microorganism. In an exemplary embodiment, the microorganism is a bacteria. In an exemplary embodiment, wherein said mutated tRNA synthetases contain amino acid mutations in their editing domains.

V. Amino Acid and Nucleotide Sequences Used in Assays

Amino acid and nucleotide sequences of use in the invention are published in references described and incorporated by reference herein, such as U.S. Pat. No. 7,816,344 and U.S. Pat. Pubs. US20060234981, US20070155699 and US20070293457. The sequence for the codon optimized *M. tuberculosis* leuS gene is as follows:

```
                                              (SEQ. ID. 1)
CATATGACCGAAAGCCCGACCGCAGGTCCGGGTGGTGTGCCGCGTGCGGA

TGATGCAGATAGCGATGTGCCGCGTTATCGTTATACCGCGGAACTGGCGG

CGCGTCTGGAACGTACCTGGCAGGAAAACTGGGCGCGTCTGGGCACCTTT

AACGTGCCGAACCCGGTGGGTAGCCTGGCACCGCCGGATGGTGCAGCAGT

GCCGGATGATAAACTGTTTGTGCAGGATATGTTTCCGTATCCGAGCGGCG

AAGGCCTGCATGTGGGCCATCCGCTGGGCTATATTGCGACCGATGTGTAT

GCGCGTTATTTTCGTATGGTGGGCCGTAACGTGCTGCATGCGCTGGGCTT

TGATGCGTTTGGTCTGCCGGCGGAACAGTATGCGGTGCAGACCGGCACCC

ATCCGCGTACCCGTACCGAAGCGAACGTGGTGAACTTTCGTCGTCAGCTG

GGCCGTCTGGGCTTTGGCCATGATAGCCGTCGTAGCTTTAGCACCACCGA

TGTGGATTTTTATCGTTGGACCCAGTGGATTTTTCTGCAGATTTATAACG

CGTGGTTTGATACCACCGCGAACAAAGCGCGTCCGATTAGCGAACTGGTG

GCGGAATTTGAAAGCGGTGCACGTTGCCTGGATGGTGGTCGTGATTGGGC

AAAACTGACCGCAGGTGAACGTGCGGATGTGATTGATGAATATCGTCTGG

TGTATCGTGCGGATAGCCTGGTGAACTGGTGCCCGGGTCTGGGTACCGTG

CTGGCAAACGAAGAAGTGACCGCAGATGGCCGTAGCGATCGTGGCAACTT

TCCGGTGTTTCGTAAACGTCTGCGTCAGTGGATGATGCGTATTACCGCGT

ATGCGGATCGTCTGCTGGATGATCTGGATGTGCTGGATTGGCCGGAACAG

GTGAAAACCATGCAGCGTAACTGGATTGGCCGTAGCACCGGCGCGGTGGC

GCTGTTTAGCGCGCGTGCGGCGAGCGATGATGGCTTTGAAGTGGATATTG
```

-continued
```
AAGTGTTTACCACCCGTCCGGATACCCTGTTTGGCGCGACCTATCTGGTG

CTGGCGCCGGAACATGATCTGGTGGATGAACTGGTGGCGGCAAGCTGGCC

GGCAGGTGTGAACCCGCTGTGGACCTATGGCGGTGGTACCCCGGGTGAAG

CAATTGCAGCATATCGTCGTGCGATTGCGGCGAAAAGCGATCTGGAACGT

CAGGAAAGCCGTGAAAAAACCGGCGTGTTTCTGGGCAGCTATGCGATTAA

CCCGGCGAACGGCGAACCGGTGCCGATTTTTATTGCGGATTATGTGCTGG

CGGGCTATGGCACCGGCGCGATTATGCGGTGCCGGGCCATGATCAGCGT

GATTGGGATTTTGCGCGTGCGTTTGGCCTGCCGATTGTGGAAGTGATTGC

AGGTGGAAACATTAGCGAAAGCGCGTATACCGGCGATGGCATTCTGGTGA

ACAGCGATTATCTGAACGGCATGAGCGTGCCGGCAGCAAAACGTGCAATT

GTGGATCGTCTGGAAAGCGCAGGTCGTGGTCGTGCACGTATTGAATTTAA

ACTGCGTGATTGGCTGTTTGCGCGTCAGCGTTATTGGGGCGAACCGTTTC

CGATTGTGTATGATAGCGATGGCCGTCCGCATGCGCTGGATGAAGCGGCG

CTGCCGGTGGAACTGCCGGATGTGCCGGATTATAGCCCGGTGCTGTTTGA

TCCGGATGATGCGGATAGCGAACCGAGCCCGCCGCTGGCGAAAGCGACCG

AATGGGTGCATGTGGATCTGGATCTGGGCGATGGCCTGAAACCGTATAGC

CGTGATACCAACGTGATGCCGCAGTGGGCGGGCAGCAGCTGGTATGAACT

GCGTTATACCGATCCGCATAACAGCGAACGTTTTTGCGCGAAAGAAAACG

AAGCGTATTGGATGGGTCCGCGTCCGGCAGAACATGGTCCGGATGATCCG

GGTGGTGTGGATCTGTATGTGGGCGGCGCGGAACATGCGGTGCTGCATCT

GCTGTATAGCCGTTTTTGGCATAAAGTGCTGTATGATCTGGGCCATGTGA

GCAGCCGTGAACCGTATCGTCGTCTGGTGAACCAGGGCTATATTCAGGCG

TATGCGTATACCGATGCGCGTGGCAGCTATGTGCCGGCGGAACAAGTGAT

TGAACGTGGCGATCGTTTTGTGTATCCGGCCCGGATGGCGAAGTGGAAG

TGTTTCAGGAATTTGGCAAAATTGGCAAAAGCCTGAAAAACAGCGTGAGC

CCGGATGAAATTTGCGATGCGTATGGCGCGGATACCCTGCGTGTGTATGA

AATGAGCATGGGCCCGCTGGAAGCGAGCCGTCCGTGGGCGACCAAAGATG

TGGTGGGCGCGTATCGTTTTCTGCAGCGTGTGTGGCGTCTGGTGGTGGAT

GAACATACCGGCGAAACCCGTGTGGCGGATGGCGTGGAACTGGATATTGA

TACCCTGCGTGCGCTGCATCGTACCATTGTGGGCGTGAGCGAAGATTTTG

CGGCGCTGCGTAACAACACCGCGACCGCGAAACTGATTGAATATACCAAC

CATCTGACCAAAAAACATCGTGATGCAGTGCCGCGTGCGGCAGTGGAACC

GCTGGTGCAGATGCTGGCACCGCTGGCACCGCATATTGCGGAAGAACTGT

GGCTGCGTCTGGGCAACACCACCAGCCTGGCGCATGGCCCGTTTCCGAAA

GCGGATGCGGCGTATCTGGTGGATGAAACCGTGGAATATCCGGTGCAGGT

GAACGGCAAAGTGCGTGGTCGTGTGGTGGTGGCGGCGGATACCGATGAAG

AAACCCTGAAAGCGGCGGTGCTGACCGATGAAAAAGTGCAGGCGTTTCTG

GCGGGCGCGACCCCGCGTAAAGTGATTGTGGTGGCGGGCCGTCTGGTGAA

CCTGGTGATTTAACTCGAG
```

VI. Methods

In another aspect, the compounds of the invention can be utilized to inhibit an enzyme. In another aspect, the compounds of the invention and/or combinations of the invention exhibit potency against microorganisms, such as bacteria, and therefore have the potential to kill and/or inhibit the growth of microorganisms. In another aspect, the compounds of the invention and/or combinations of the invention exhibit potency against microorganisms, such as bacteria, and therefore have the potential to achieve therapeutic efficacy in the animals described herein.

VI. a) LeuRS

In an exemplary embodiment, the compounds of the invention exhibit the ability of inhibiting the editing domain of tRNA synthetases, such as leucyl tRNA synthetase, of microorganisms, such as bacteria, and therefore have the potential to be used as editing domain inhibitors of microorganism tRNA synthetases.

According to another aspect of the invention, a method for binding to and/or inhibiting the editing domain of a tRNA synthetase is provided which comprises contacting a tRNA synthetase with a compound of the invention that inhibits the editing domain under conditions in which the tRNA synthetase interacts with its substrate to form an aminoacyl adenylate intermediate and, preferably, to form a charged tRNA. Such conditions are known to those skilled in the art. In an exemplary embodiment, the compound has a structure according to a formula described herein. In an exemplary embodiment, the compound is described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the invention provides a compound described herein, or a salt thereof. The tRNA synthetase is contacted with an amount of compound of the invention sufficient to result in a detectable amount of tRNA synthetase inhibition. This method can be performed on a tRNA synthetase that is contained within an organism or which is outside an organism. In an exemplary embodiment, the method is performed on a tRNA synthetase that is contained within a microorganism or a microbial cell that is in, or on the surface of, an animal. In an exemplary embodiment, the animal is a human. The method results in a decrease in the amount of charged tRNA produced by the tRNA synthetase that has an inhibited editing domain. In an exemplary embodiment, the inhibition takes place in a cell, such as a microorganism cell. In another exemplary embodiment, the microorganism cell is a bacteria. In another exemplary embodiment, the tRNA synthetase is leucyl tRNA synthetase.

In an exemplary embodiment, the invention provides a method of inhibiting conversion of a tRNA molecule into a charged tRNA molecule. The method involves contacting a tRNA synthetase with a compound of the invention effective to inhibit activity of an editing domain of said tRNA synthetase, under conditions sufficient to inhibit said activity, thereby inhibiting said conversion. In an exemplary embodiment, the compound of the invention is a compound described herein, or a pharmaceutically acceptable salt thereof. In an exemplary embodiment, the inhibition occurs within a cell, and the cell is a microorganism cell. In another exemplary embodiment, the microorganism cell is a bacteria. In another exemplary embodiment, the microorganism cell is a bacteria which is described herein. In another exemplary embodiment, the enzyme is a leucyl tRNA synthetase of a bacteria described herein. In another exemplary embodiment, the tRNA synthetase is leucyl tRNA synthetase. In another exemplary embodiment, the compound has a $K_{D, \text{ synthesis}}$ of greater than 100 µM against a synthetic domain of said tRNA synthetase.

In certain embodiments, the mechanism of action of a compound of the invention is to inhibit the conversion of a tRNA molecule into a charged tRNA molecule by binding to and/or inhibiting at least the editing domain of the synthetase. The compounds of use in this method may also inhibit or otherwise interact with the synthetic domain (e.g., the active site of the synthetic domain). In a presently preferred embodiment, the editing domain is inhibited selectively in the presence of the synthetic domain. In a preferred embodiment, the synthetic domain is essentially uninhibited, while the editing domain is inhibited at least 50%, preferably at least 60%, more preferably at least 70%, still more preferably, at least 80% and even still more preferably at least 90% of the activity of the tRNA synthetase. In another preferred embodiment, the synthetic domain is inhibited by at most 50%, preferably at most 30%, preferably at most 20%, 10%, preferably at most 8%, more preferably at most 5%, still more preferably, at most 3% and even still more preferably at most 1%. Inhibition of the editing domain produces a decrease in the amount of the properly charged tRNA which results in retardation or cessation of cell growth and division.

In another exemplary embodiment, the ratio of a minimum concentration of said compound inhibiting said editing domain to a minimum concentration of said compound inhibiting said synthetic domain of said tRNA synthetase, represented as $K_{D, \text{ edit}}/K_{D, \text{ synthesis}}$, is less than one. In another exemplary embodiment, the $K_{D, \text{ edit}}/K_{D, \text{ synthesis}}$ of the compound is a member selected from less than 0.5, less than 0.1 and less than 0.05.

VI. b) Inhibiting Microorganism Growth or Killing Microorganisms

The compounds of the invention and/or combinations of the invention exhibit potency against microorganisms, such as bacteria, and therefore have the potential to treat, and/or prevent a microorganism infection, or kill and/or inhibit the growth of microorganisms.

In a further aspect, the invention provides a method of treating and/or preventing a microorganism infection, or a method of killing and/or inhibiting the growth of a microorganism, said method comprising: contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising: contacting said microorganism with an effective amount of a combination of the invention, thereby killing and/or inhibiting the growth of the microorganism.

In a further aspect, the invention provides a method of treating a bacterial infection comprising administering to an animal suffering from the infection an effective amount of a compound of the invention or a combination of the invention, or a pharmaceutically acceptable salt thereof, thereby treating the bacterial infection. In an exemplary embodiment, the invention provides a method of treating a bacterial infection comprising administering to an animal suffering from the infection an effective amount of a compound of the invention, or a pharmaceutically acceptable salt thereof, and an effective amount of an antibiotic, or a pharmaceutically acceptable salt thereof, thereby treating the bacterial infection.

In a further aspect, the invention provides a method of preventing a bacterial infection comprising administering to an animal a prophylactic amount of a compound of the invention or a combination of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof.

In an exemplary embodiment, the microorganism is a bacteria. In an exemplary embodiment, the compound or combination is described herein, or a salt, prodrug, hydrate or solvate thereof, or a combination thereof. In an exemplary embodiment, the invention provides a compound or combination described herein, or a salt, hydrate or solvate thereof. In an exemplary embodiment, the invention provides a compound or combination described herein, or a prodrug thereof. In an exemplary embodiment, the invention provides a compound or combination described herein, or a salt thereof. In another exemplary embodiment, the compound or combination of the invention is a compound or combination described herein, or a pharmaceutically acceptable salt thereof. In another exemplary embodiment, the compound or compound of the combination is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the contacting occurs under conditions which permit entry of the compound into the organism. Such conditions are known to one skilled in the art and are described herein.

In another aspect, the microorganism is inside, or on the surface of an animal. In another exemplary embodiment, the animal is described herein. In another exemplary embodiment, the animal is a human.

In an exemplary embodiment, the microorganism infection is treated and/or prevented, or the microorganism is killed or its growth is inhibited, through oral administration of the compound of the invention and/or the combination of the invention. In an exemplary embodiment, the microorganism infection is treated and/or prevented, or the microorganism is killed or its growth is inhibited through intravenous administration of the compound of the invention and/or the combination of the invention.

In an exemplary embodiment, the microorganism is a bacterium. In an exemplary embodiment, an infection is caused by and/or associated with a microorganism, particularly a bacterium. In an exemplary embodiment, the bacterium is a gram-positive bacteria. In another exemplary embodiment, the gram-positive bacterium is selected from the group consisting of *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the gram-positive bacterium is selected from the group consisting of *Propionibacterium acnes, Staphylococcus aureus, Staphylococcus epidermidis, Staphylococcus saprophyticus, Staphylococcus haemolyticus, Streptococcus pyogenes, Streptococcus agalactiae, Streptococcus pneumoniae, Enterococcus faecalis, Enterococcus faecium, Actinomyces israelii, Bacillus anthracis, Corynebacterium diph-* theria, *Clostridium perfringens, Clostridium botulinum, Clostridium tetani*, and *Clostridium difficile*. In another exemplary embodiment, the gram-positive bacterium is selected from the group consisting of *Staphylococcus aureus, Staphylococcus epidermidis, Streptococcus pneumoniae, Streptococcus pyogenes, Enterococcus faecalis, Enterococcus faecium, Clostridium difficile* and *Propionibacter acnes*. In another exemplary embodiment, the bacterium is a gram-negative bacterium. In another exemplary embodiment, the gram-negative bacterium is selected from the group consisting of *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species, *Helicobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is selected from the group consisting of *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is selected from the group consisting of *Neisseria gonorrhoeae, Neisseria meningitidis, Pseudomonas aeruginosa, Legionella pneumophila, Escherichia coli, Yersinia pestis, Haemophilus influenzae, Helicobacter pylori, Campylobacter fetus, Campylobacter jejuni, Vibrio cholerae, Vibrio parahemolyticus, Trepomena pallidum, Rickettsia prowazekii, Rickettsia rickettsii, Chlamydia trachomatis, Chlamydia psittaci, Brucella abortus, Agrobacterium tumefaciens, Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is selected from the group consisting of *Pseudomonas aeruginosa, Escherichia coli, Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is selected from the group consisting of *Enterobacter aerogenes, Enterobacter cloacae, Enterobacter sakazakii, Escherichia coli, Klebsiella pneumoniae, Proteus mirabilis, Serratia marcescens* and *Citrobacter freundii*. In another exemplary embodiment, the gram-negative bacterium is a *Providencia* spp.

In an exemplary embodiment, the microorganism is an acid-fact bacteria. In another exemplary embodiment, the bacterium is a *Mycobacterium* spp. In another exemplary embodiment, the bacterium is *Mycobacterium avium*. In another exemplary embodiment, the bacterium is *Mycobacterium avium-intracellulare*. In another exemplary embodiment, the bacterium is *Mycobacterium kansasii*. In another exemplary embodiment, the bacterium is *Mycobacterium leprae*. In another exemplary embodiment, the bacterium is *Mycobacterium lepromatosis*. In another exemplary embodiment, the bacterium is *Mycobacterium africanum*. In another exemplary embodiment, the bacterium is *Mycobacterium canetti*. In another exemplary embodiment, the bacterium is *Mycobacterium microti*. In another exemplary embodiment, the bacterium is *Mycobacterium tuberculosis*. In another exemplary embodiment, the bacterium is *Mycobacterium tuberculosis* which is multi-drug resistant. In another exemplary embodiment, the bacterium is *Mycobacterium tuberculosis* which is extensively drug resistant. In another exemplary embodiment, the bacterium is *Mycobacterium tuberculosis* which is resistant to rifampicin. In another exemplary embodiment, the bacterium is *Mycobacterium tuberculosis* which is resistant to isoniazid. In another exemplary embodiment, the bacterium is *Mycobacterium tuberculosis* which is resistant to kanamycin. In another exemplary embodiment, the bacterium is *Mycobacterium tuberculosis* which is resistant to capreomycin. In another exemplary embodiment, the bacterium is *Mycobacterium tuberculosis* which is resistant to amikacin.

In another exemplary embodiment, the bacterium is a *Pseudomonas* species. In another exemplary embodiment, the bacterium is *Pseudomonas aeruginosa*. In another exemplary embodiment, the bacterium is selected from the group consisting of *Pseudomonas aeruginosa, Acinetobacter baumannii, Stenotrophomonas maltophilia* and *Burkholderia cepacia*. In another exemplary embodiment, the bacterium is *Acinetobacter baumannii*. In another exemplary embodiment, the bacterium is *Stenotrophomonas maltophilia*. In another exemplary embodiment, the bacterium is *Burkholderia cepacia*. In another exemplary embodiment, the bacterium is *Acinetobacter* species. In another exemplary embodiment, the bacterium is *Acinetobacter anitratus*. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii* and *Providencia* spp. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii, Providencia* spp., *S. aureus, S. pneumonia, S. pyogenes, E. faecalis*, and *E. faecium*. In another exemplary embodiment, the bacterium is selected from the group consisting of *Pseudomonas aeruginosa, Acinetobacter baumannii, Stenotrophomonas maltophilia, Burkholderia cepacia*. In another exemplary embodiment, the bacterium is selected from the group consisting of *S. aureus, S. pneumonia, S. pyogenes, E. faecalis*, and *E. faecium*. In another exemplary embodiment, the bacterium is selected from the group consisting of Viridans group Strep. In another exemplary embodiment, the bacterium is selected from the group consisting of *Strep. mitis, Strep. mutans, Strep. oralis, Strep. sanguis, Strep. sobrinus* and *Strep. millari*. In another exemplary embodiment, the bacterium is *S. pneumonia*. In another exemplary embodiment, the bacterium is *H. influenzae*. In another exemplary embodiment, the bacterium is *S. aureus*. In another exemplary embodiment, the bacterium is *M. catarrhalis*. In another exemplary embodiment, the bacterium is *M. pneumoniae*. In another exemplary embodiment, the bacterium is *L. pneumoniae*. In another exemplary embodiment, the bacterium is *C. pneumoniae*. In another exemplary embodiment, the bacterium is *S. pyogenes*. In another exemplary embodiment, the bacterium is an anaerobe. In another exemplary embodiment, the bacterium is an *Alcaligenes* species. In another exemplary embodiment, the bacterium is a *B. cepacia*. In another exemplary embodiment, the bacterium is selected from the group consisting of *Enterobacter cloacae, Escherichia coli, Klebsiella pneumoniae, Proteus mirabilis, Providencia stuartii, Serratia marcescens*, and *Citrobacter freundii*. In another exemplary embodiment, the bacterium is resistant to methicillin. In another exemplary embodiment, the bacterium is methicillin-resistant *Staphylococcus aureus*. In another exemplary embodiment, the bacterium is selected from the group consisting of *Streptococcus pneumoniae, Haemophilus influenzae, Staphylococcus aureus, Mycobacterium catarrhalis, Mycobacterium pneumoniae, Legionella pneumophila* and *Chlamydia pneumoniae*. In another exemplary embodiment, the bacterium is selected from the group consisting of *Enterobacter cloacae, Escherichia coli, Klebsiella pneumoniae, Proteus mirabilis, Serratia marcescens, Citrobacter freundii, Providencia stuartii, Pseudomonas aeruginosa, Acinetobacter baumannii, Stenotrophomonas maltophilia, Burkholderia cepacia, Staphylococcus aureus, Streptococcus pneumoniae, Streptococcus pyogenes, Enterococcus faecalis,* and *Enterococcus faecium*. In another exemplary embodiment, the bacterium is selected from the group consisting of *Staphylococcus aureus, Staphylococcus epidermidis, Staphylococcus haemolyticus, Streptococcus pyogenes, Streptococcus agalactiae* and *Streptococcus pneumoniae*.

In an exemplary embodiment, the microorganism is a bacterium, which is selected from the group consisting of bacilli, including *Bacillus* species, *Corynebacterium* species (also *Propionibacterium*) and *Clostridium* species; filamentous bacteria, including *Actinomyces* species and *Streptomyces* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

VI. b) Microorganism Infection

The compounds of the invention and/or combinations of the invention exhibit potency against microorganisms, such as bacteria, and therefore have the potential to be used to treat and/or prevent a microorganism infection, such as a bacterial infection.

In a further aspect, the invention provides a method of treating a bacterial infection comprising administering to an animal suffering from the infection an effective amount of a compound of the invention, or a pharmaceutically acceptable salt thereof, thereby treating the bacterial infection. In an exemplary embodiment, the invention provides a method of treating a bacterial infection comprising administering to an animal suffering from the infection an effective amount of a compound of the invention, or a pharmaceutically acceptable salt thereof, and an effective amount of an antibiotic, or a pharmaceutically acceptable salt thereof, thereby treating the bacterial infection.

In a further aspect, the invention provides a method of preventing a bacterial infection comprising administering to an animal a prophylactic amount of a compound of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof, and an effective amount of an antibiotic, or a pharmaceutically acceptable salt thereof, thereby treating the bacterial infection.

VI. c) Diseases

The compounds of the invention and/or combinations of the invention exhibit potency against microorganisms, such as bacteria, and therefore have the potential to achieve therapeutic efficacy in the animals described herein.

In another aspect, the invention provides a method of treating and/or preventing a disease. In an exemplary embodiment, the method includes administering to the animal a therapeutically effective amount of a compound of the invention, thereby treating and/or preventing the disease. In an exemplary embodiment, the method includes administering to the animal a therapeutically effective amount of a combination of the invention, thereby treating and/or preventing the disease. In an exemplary embodiment, the compound of the invention or the combination of the invention can be used in human or veterinary medical therapy, particularly in the treatment or prophylaxis of bacterial-associated disease. In an exemplary embodiment, the compound is described herein, or a salt, prodrug, hydrate or solvate thereof, or a combination thereof. In an exemplary embodiment, the invention provides a compound described herein, or a prodrug thereof. In an exemplary embodiment, the invention provides a compound described herein, or a salt, hydrate or solvate thereof. In an exemplary embodiment, the invention provides a compound described herein, or a salt thereof. In another exemplary embodiment, the compound of the invention is a compound described herein, or a pharmaceutically acceptable salt thereof. In an exemplary embodiment, the compound is a compound described herein, or a pharmaceutically acceptable salt thereof. In an exemplary embodiment, the compound is according to a formula described herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the disease is a systemic disease. In another exemplary embodiment, the disease is a topical disease. In an exemplary embodiment, the animal being administered the compound is not otherwise in need of treatment with the compound.

In an exemplary embodiment, the disease is treated through oral administration of a compound of the invention and/or a combination of the invention. In an exemplary embodiment, the disease is treated through intravenous administration of a compound of the invention and/or a combination of the invention. In an exemplary embodiment, the disease is treated through subcutaneous administration of a compound of the invention and/or a combination of the invention.

Systemic Diseases

In another aspect, the invention provides a method of treating a systemic disease. The method involves contacting an animal with a compound of the invention and/or a combination of the invention.

In another exemplary embodiment, the disease is associated with a bacteria described herein. In another exemplary embodiment, the disease is associated with infection by a Gram-positive bacteria. In an exemplary embodiment, the disease is associated with a *Staphylococcus* species. In another exemplary embodiment, the disease is selected from the group consisting of pneumonia, gastroenteritis, toxic shock syndrome, community acquired pneumonia (CAP), meningitis, septic arthritis, urinary tract infection, bacteremia, endocarditis, osteomylitis, skin and skin-structure infection. In an exemplary embodiment, the disease is associated with a *Streptococcus* species. In another exemplary embodiment, the disease is selected from the group consisting of strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diphtheria. In an exemplary embodiment, the disease is associated with a *Listeria* species. In another exemplary embodiment, the disease is meningitis. In an exemplary embodiment, the disease is associated with a *Bacillus* species. In another exemplary embodiment, the disease is anthrax or food poisoning. In an exemplary embodiment, the disease is associated with a *Clostridium* species. In another exemplary embodiment, the disease is selected from the group consisting of botulism, tetanus, gas gangrene and diarrhea.

In an exemplary embodiment, the disease is associated with a *Mycobacterium* species. In an exemplary embodiment, the disease is associated with *Mycobacterium tuberculosis*. In an exemplary embodiment, the disease is associated with *Mycobacterium kansasii*. In an exemplary embodiment, the disease is associated with *Mycobacterium avium-intracellulare*. In another exemplary embodiment, the disease is leprosy. In another exemplary embodiment, the disease is *tuberculosis*. In another exemplary embodiment, the disease is pulmonary *tuberculosis*. In another exemplary embodiment, the disease is extrapulmonary *tuberculosis*. In another exemplary embodiment, the disease is associated with multi-drug resistant *tuberculosis*. In another exemplary embodiment, the disease is associated with extensively drug resistant *tuberculosis*.

In another exemplary embodiment, the disease is associated with infection by a Gram-negative bacteria. In an exemplary embodiment, the disease is associated with a *Neisseria* species. In another exemplary embodiment, the disease is selected from the group consisting of meningitis, gonorrhea, otitis extema and folliculitis. In an exemplary embodiment, the disease is associated with an *Escherichia* species. In another exemplary embodiment, the disease is selected from the group consisting of diarrhea, urinary tract infections, meningitis, sepsis and HAP. In an exemplary embodiment, the disease is associated with a *Shigella* species. In another exemplary embodiment, the disease is selected from the group consisting of diarrhea, bacteremia, endocarditis, meningitis and gastroenteritis. In an exemplary embodiment, the disease is associated with a *Salmonella* species. In another exemplary embodiment, the disease is selected from the group consisting of Typhoid fever, sepsis, gastroenteritis, endocarditis, sinusitis and meningitis. In an exemplary embodiment, the disease is associated with a *Yersinia* species. In another exemplary embodiment, the disease is selected from the group consisting of Typhoid fever, bubonic plague, enteric fever and gastroenteritis. In an exemplary embodiment, the disease is associated with a *Klebsiella* species. In another exemplary embodiment, the disease is sepsis or urinary tract infection. In an exemplary embodiment, the disease is associated with a *Proteus* species. In another exemplary embodiment, the disease is an urinary tract infection. In an exemplary embodiment, the disease is associated with an *Enterobacter* species. In another exemplary embodiment, the disease is a hospital-acquired infection. In an exemplary embodiment, the disease is associated with a *Serratia* species. In another exemplary embodiment, the disease is selected from the group consisting of a urinary tract infection, skin and skin-structure infection and pneumonia. In an exemplary embodiment, the disease is associated with a *Vibrio* species. In another exemplary embodiment, the disease is cholera or gastroenteritis. In an exemplary embodiment, the disease is associated with a *Campylobacter* species. In another exemplary embodiment, the disease is gastroenteritis. In an exemplary embodiment, the disease is associated with a *Helicobacter* species. In another exemplary embodiment, the disease is chronic gastritis. In an exemplary embodiment, the disease is associated with a *Pseudomonas* species. In another exemplary embodiment, the disease is selected from the group consisting of pneumonia, osteomylitis, burn-wound infections, sepsis, UTIs, endocarditis, otitis and corneal infections. In an exemplary embodiment, the disease is associated with a *Bacteroides* species. In another exemplary embodiment, the disease is periodontal disease or aspiration pneumonia. In an exemplary embodiment, the disease is associated with a *Haemophilus* species. In another exemplary embodiment, the disease is selected from the group consisting of meningitis, epiglottitis, septic arthritis, sepsis, chancroid and vaginitis. In an exemplary embodiment, the disease is associated with a *Bordetella* species. In another exemplary embodiment, the disease is Whooping cough. In an exemplary embodiment, the disease is associated with a *Legionella* species. In another exemplary embodiment, the disease is pneumonia or pontiac fever. In an exemplary embodiment, the disease is associated with a *Francisella* species. In another exemplary embodiment, the disease is tularemia. In an exemplary embodiment, the disease is associated with a *Brucella* species. In another exemplary embodiment, the disease is brucellosis. In an exemplary embodiment, the disease is associated with a *Pasteurella* species. In another exemplary embodiment, the disease is a skin infection. In an exemplary embodiment, the disease is associated with a *Gardnerella* species. In another exemplary embodiment, the disease is vaginitis. In an exemplary embodiment, the disease is associated with a *Spirochetes* species. In another exemplary embodiment, the disease is syphilis or Lyme disease. In an exemplary embodiment, the disease is associated with a *Chlamydia* species. In another exemplary embodiment, the disease is *chlamydia*. In an exemplary embodiment, the disease is associated with a *Rickettsiae* species. In another exemplary embodiment, the disease is Rocky Mountain spotted fever or typhus.

In an exemplary embodiment, the disease is associated with *Mycoplasma pneumoniae*. In another exemplary embodiment, the disease is tracheobronchitis or walking pneumonia. In an exemplary embodiment, the disease is associated with *Ureaplasma urealyticum*. In another exemplary embodiment, the disease is urethritis. In another exemplary embodiment, the disease is pyelonephritis. In another exemplary embodiment, the disease is an intra-abdominal infection. In another exemplary embodiment, the disease is febrile neutropenia. In another exemplary embodiment, the disease is a pelvic infection. In another exemplary embodiment, the disease is bacteraemia. In another exemplary embodiment, the disease is septicaemia.

In an exemplary embodiment, the disease is an acute exacerbation of chronic obstructive pulmonary disease. In an exemplary embodiment, the disease is chronic obstructive pulmonary disease. In an exemplary embodiment, the disease is pharyngitis. In an exemplary embodiment, the disease is tonsillitis. In an exemplary embodiment, the disease is Acute Exacerbation of Chronic Bronchitis (AECB). In an exemplary embodiment, the disease is cervicitis. In an exemplary embodiment, the disease is genital ulcer disease.

In an exemplary embodiment, for any of the methods described herein, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is selected from the group consisting of a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention, a combination of the invention, a compound described herein or a pharmaceutically acceptable salt thereof, or combination described herein, and/or a pharmaceutical formulation described herein can be used.

VII. Pharmaceutical Formulation

In another aspect, the invention provides a pharmaceutical formulation comprising: a) a compound of the invention; and b) a pharmaceutically acceptable excipient. In another aspect, the invention provides a pharmaceutical formulation comprising: a) a combination of the invention; and b) a pharmaceutically acceptable excipient. In an exemplary embodiment, the compound is according to a formula described herein. In an exemplary embodiment, the compound is according to an example described herein. In an exemplary embodiment, the compound of the invention or combination of the invention is a compound described herein or combination described herein, or a pharmaceutically acceptable salt thereof. In an exemplary embodiment, the compound of the invention is a compound described herein.

In an exemplary embodiment, the compound of the invention is present in the pharmaceutical formulation in an amount of between about 0.0001% to about 60% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 1.0% and about 2.0% (w/w). In an exemplary embodiment, the amount is between about 2.0% and about 3.0% (w/w). In an exemplary embodiment, the amount is between about 3.0% and about 4.0% (w/w). In an exemplary embodiment, the amount is between about 4.0% and about 5.0% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The compositions of the invention may be administered orally, topically, parenterally, by inhalation or spray or rectally in dosage unit formulations containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; lubricating agents, for example magnesium stearate, stearic acid or talc; and extenders and bulking agents, such as microcrystalline cellulose. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Other dispersing agents include hydrophilic polymers, electrolytes, Tween™ 60 or 80, PEG, polyvinylpyrrolidone (PVP; commercially known as Plasdone™), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone™ e.g., S-630), 4-(1,1,3,3-tetramethylbutyl)-phenol polymer with ethylene oxide and formaldehyde (also known as tyloxapol), poloxamers (e.g., Pluronics F68™, F88™, and F108™, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical composition described herein includes an additional active ingredient. In another exemplary embodiment, the additional active ingredient is a compound that has been approved for human use by the United States Food and Drug Administration. In another exemplary embodiment, the additional active ingredient is an immunosuppressive agent. In still another exemplary embodiment, the additional active ingredient is selected from the group consisting of corticosteroids, aminosalicylates, azathioprine (6-mercaptopurine), methotrexate and cyclosporine, etanercept, infliximab, adalimumab, alefacept, efalizumab and anakinra.

In still another exemplary embodiment, the additional active ingredient is selected from the group consisting of betamethasone, tacrolimus and pimecrolimus. In still another exemplary embodiment, the additional active ingredient is selected from the group consisting of an activated vitamin D analog and an arotinoid (an aromatic retinoic acid analog). In still another exemplary embodiment, the additional active ingredient is carcipotriol, such as Tazorac (tazarotene).

VII. a) Topical Formulations

In a preferred embodiment, the methods of the invention can be employed through the topical application of the compounds described herein. Topical administration includes for example, transmucosal, transdermal, ungual and transungual routes of administration. The topical compositions useful in the subject invention can be made into a wide variety of product types. These include, but are not limited to, lotions, creams, gels, sticks, sprays, ointments, pastes, foams, mousses, masks, eye ointments, eye or ear drops, impregnated dressings, wipes, cleansers including soaps, body washes and shampoos, and make-up products, such as bases, blushes, lipsticks, and eye shadows, among others. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in Remington: The Science and Practice of Pharmacy, supra. The formulation can be selected to maximize delivery to a desired target site in the body. The formulations can also include various conventional colorants, fragrances, thickeners, preservatives, humectants, emollients, demulcents, solubilizing excipients, dispersants, penetration enhancers, plasticizing agents, preservatives, stabilizers, demulsifiers, wetting agents, sunscreens, emulsifiers, moisturizers, astringents, deodorants, and the like, which can be added to provide additional benefits such as, for example, improving the feel and/or appearance of the topical preparation.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethylcellulose, or the like.

Creams containing the active agent for delivery according to the invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in Remington: The Science and Practice of Pharmacy, supra, is generally a nonionic, anionic, cationic or amphoteric surfactant.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Preferred water-soluble ointment bases are prepared from polyethylene glycols of varying molecular weight; again, reference may be had to Remington: The Science and Practice of Pharmacy, supra, for further information.

Useful formulations of the invention also encompass sprays and aerosols. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration. Examples of aerosol technology are disclosed in U.S. Pat. Nos. 6,682,716; 6,716,415; 6,716,417; 6,783,753; 7,029,658; and 7,033,575.

Examples of solubilizing excipients include polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, tocopherol esters, and sterol esters.

Exemplary embodiments are summarized herein below.

In an exemplary embodiment, the invention provides a compound having a structure according to a formula which is:

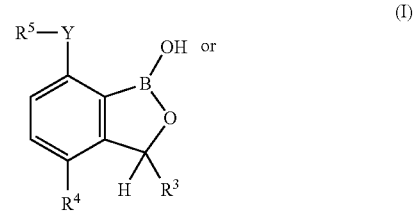

(I)

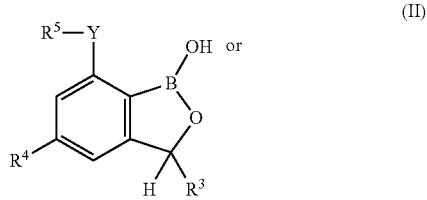

(II)

-continued

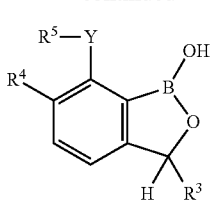
(III)

wherein R³ is substituted or unsubstituted nitroalkyl or substituted or unsubstituted aminoalkyl; R⁴ is selected from the group consisting of halogen, unsubstituted alkyl, unsubstituted alkoxy, and unsubstituted phenyl; Y is O or S; and R⁵ is selected from the group consisting of substituted or unsubstituted alkyl and substituted or unsubstituted heteroalkyl; or a salt, hydrate or solvate thereof.

In an exemplary embodiment, according to the above paragraph, having a structure which is

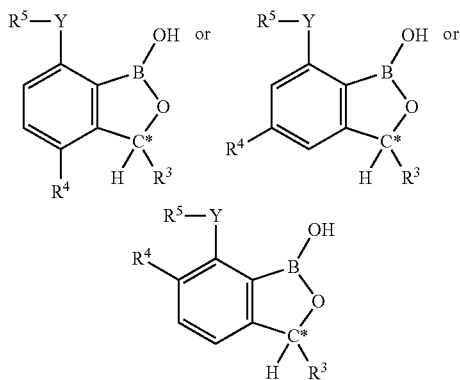

wherein C* is a carbon atom stereocenter which has a configuration which is (R) or (S).

In an exemplary embodiment, according to any of the above paragraphs, wherein C* stereocenter is in a (S) configuration.

In an exemplary embodiment, according to any of the above paragraphs, wherein R³ is —(CR²OR²¹)ₙNR²²R²³ in which n is 1, 2, 3, 4, 5, 6, 7, 8, 9, or 10;
each R²⁰ and each R²¹ is independently selected from the group consisting of H, R²⁶, OR²⁶, NR²⁶R²⁷, SR²⁶, —S(O)R²⁶, —S(O)₂R²⁶, —S(O)₂NR²⁶R²⁷, —C(O)R²⁷, —C(O)OR²⁷ and —C(O)NR²⁶R²⁷
R²² and R²³ are independently selected from the group consisting of H, —S(O)R²⁸, —S(O)₂R²⁸, —S(O)₂NR²⁸R²⁹, —C(O)R²⁸, —C(O)OR²⁸, —C(O)NR²⁸R²⁹, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein each R²⁶, each R²⁷, each R²⁸ and each R²⁹ is independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, R³ is —CH₂NH₂.

In an exemplary embodiment, according to any of the above paragraphs, R³ is —CH₂NH₂, and C* has a configuration which is (S).

In an exemplary embodiment, according to any of the above paragraphs, R⁴ is selected from the group consisting of methyl, ethyl, propyl, isopropyl, butyl, isobutyl, and sec-butyl.

In an exemplary embodiment, according to any of the above paragraphs, R⁴ is selected from the group consisting of fluorine, chlorine, bromine, and iodine.

In an exemplary embodiment, according to any of the above paragraphs, R⁴ is fluorine.

In an exemplary embodiment, according to any of the above paragraphs, R⁴ is chlorine.

In an exemplary embodiment, according to any of the above paragraphs, R⁴ is bromine.

In an exemplary embodiment, according to any of the above paragraphs, R⁵ is:

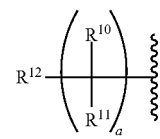

wherein a is 1, 2, 3, 4, 5, 6, 7, 8, 9, or 10; each R¹⁰ and each R¹¹ is independently selected from the group consisting of H, substituted or unsubstituted alkyl, OH and NH₂;
R¹² is selected from the group consisting of H, R⁷, halogen, cyano, amidino, OR⁷, NR⁷R⁸, SR⁷, —N(R⁷)S(O)₂R⁸, —C(O)R⁷, —C(O)OR⁷, —C(O)NR⁷R⁸ wherein each R⁷ and each R⁸ is independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, a is 1, 2, 3, 4, or 5.

In an exemplary embodiment, according to any of the above paragraphs, a is 2, 3, or 4.

In an exemplary embodiment, according to any of the above paragraphs, each R¹⁰ and each R¹¹ is independently selected from the group consisting of H, substituted or unsubstituted alkyl, OH, and NH₂.

In an exemplary embodiment, according to any of the above paragraphs, each R¹⁰ and each R¹¹ is H.

In an exemplary embodiment, according to any of the above paragraphs, R¹² is selected from the group consisting of H, OH, NH₂, methyl, ethyl, —NHS(O)₂CH₃, cyano, —NHC(O)CH₃, —NHC(O)NHCH₂CH₃, —C(O)NH₂, —C(O)OH, 4-(methoxy)phenyl, benzyl, benzoxy, —NHC(O)OCH₂Ph, —C(O)NHCH₂CH₂OH and —C(NH₂)(NH).

In an exemplary embodiment, according to any of the above paragraphs, Y is O.

In an exemplary embodiment, according to any of the above paragraphs, R⁵ is unsubstituted alkyl.

In an exemplary embodiment, according to any of the above paragraphs, R⁵ is selected from the group consisting of methyl, ethyl, propyl, isopropyl, butyl, isobutyl, t-butyl, and sec-butyl.

In an exemplary embodiment, according to any of the above paragraphs, R³ is —CH₂NH₂; and Y is O; and R⁵ is substituted or unsubstituted alkyl.

In an exemplary embodiment, according to any of the above paragraphs, R³ is —CH₂NH₂; and R⁴ is halogen.

In an exemplary embodiment, according to any of the above paragraphs, $R^4$ is halogen; Y is O; and $R^5$ is unsubstituted alkyl.

In an exemplary embodiment, according to any of the above paragraphs, $R^3$ is —$CH_2NH_2$, and C* has a configuration which is (S) and $R^4$ is halogen.

In an exemplary embodiment, according to any of the above paragraphs, $R^3$ is —$CH_2NH_2$, and C* has a configuration which is (S), $R^5$ is unsubstituted alkyl and $R^4$ is halogen.

In an exemplary embodiment, according to any of the above paragraphs, Y is O, $R^3$ is —$CH_2NH_2$, and C* has a configuration which is (S), $R^5$ is unsubstituted $C_1$ or $C_2$ or $C_3$ or $C_4$ alkyl and $R^4$ is halogen.

In an exemplary embodiment, according to any of the above paragraphs, $R^3$ is —$CH_2NH_2$; $R^4$ is chlorine; Y is O; and $R^5$ is substituted or unsubstituted alkyl.

In an exemplary embodiment, according to any of the above paragraphs, $R^3$ is —$CH_2NH_2$; Y is O; and $R^5$ is ethyl.

In an exemplary embodiment, according to any of the above paragraphs, the compound has a structure which is

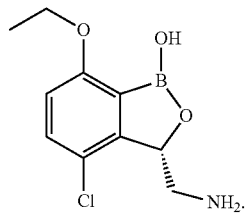 [SMILES: CCOc1ccc(Cl)c2c1B(O)O[C@@H]2CN]

In an exemplary embodiment, the invention provides a composition comprising: (a) a) a first stereoisomer of the compound according to any of the above paragraphs; b) at least one additional stereoisomer of the first stereoisomer; wherein the first stereoisomer is present in an enantiomeric excess of at least 80% relative to said at least one additional stereoisomer.

In an exemplary embodiment, according to any of the above paragraphs, wherein said enantiomeric excess is at least 92%.

In an exemplary embodiment, according to any of the above paragraphs, wherein the C* stereocenter of the first stereoisomer is in a (S) configuration.

In an exemplary embodiment, according to any of the above paragraphs, wherein $R^3$ is —$CH_2NH_2$.

In an exemplary embodiment, the invention provides a composition according to any of the above paragraphs, wherein the C* stereocenter is in a (S) configuration, and said composition is substantially free of the (R) enantiomer of the compound.

In an exemplary embodiment, the invention provides a combination comprising the compound according to any of the above paragraphs, or a pharmaceutically acceptable salt thereof, together with at least one other therapeutically active agent.

In an exemplary embodiment, the invention provides a pharmaceutical formulation comprising: (a) a compound according to any of the above paragraphs, or a pharmaceutically acceptable salt thereof; and (b) a pharmaceutically acceptable excipient.

In an exemplary embodiment, according to any of the above paragraphs, the formulation is in a unit dosage form.

In an exemplary embodiment, according to any of the above paragraphs, the formulation is for oral or topical use.

In an exemplary embodiment, the invention provides a method of inhibiting an enzyme, comprising: contacting the enzyme with the compound according to any of the above paragraphs, thereby inhibiting the enzyme.

In an exemplary embodiment, according to any of the above paragraphs, the enzyme is a t-RNA synthetase which comprises an editing domain.

In an exemplary embodiment, according to any of the above paragraphs, the enzyme is a leucyl t-RNA synthetase.

In an exemplary embodiment, the invention provides a method of killing and/or preventing the growth of a microorganism, comprising: contacting the microorganism with an effective amount of a compound according to any of the above paragraphs, or a pharmaceutically acceptable salt thereof, thereby killing and/or preventing the growth of the microorganism.

In an exemplary embodiment, according to any of the above paragraphs, the microorganism is a bacterium.

In an exemplary embodiment, according to any of the above paragraphs, the microorganism is *Mycobacterium tuberculosis*.

In an exemplary embodiment, the invention provides a method of treating and/or preventing a disease in an animal, comprising: administering to the animal a therapeutically effective amount of compound according to any of the above paragraphs, or a pharmaceutically-acceptable salt thereof, thereby treating and/or preventing the disease.

In an exemplary embodiment, according to any of the above paragraphs, the disease is *tuberculosis*.

In an exemplary embodiment, according to any of the above paragraphs, the animal is a human.

In an exemplary embodiment, the invention provides a method of inhibiting the editing domain of a t-RNA synthetase, comprising: contacting the synthetase with an effective amount of a compound according to any of the above paragraphs, or a pharmaceutically-acceptable salt thereof, thereby inhibiting the synthetase.

In an exemplary embodiment, according to any of the above paragraphs, the synthetase is a leucyl t-RNA synthetase.

In an exemplary embodiment, according to any of the above paragraphs, the synthetase is a *Mycobacterium tuberculosis* leucyl t-RNA synthetase.

In an exemplary embodiment, the invention provides the use of a compound according to any of the above paragraphs or a combination according to any of the above paragraphs or a pharmaceutically acceptable salt thereof, in the manufacture of a medicament for the treatment and/or prophylaxis of bacterial infection.

It is to be understood that the present invention covers all combinations of aspects and/or embodiments, as well as suitable, convenient and preferred groups described herein.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

The *M. tuberculosis* LeuRS gene (DNA sequence listed herein) was prepared by GenScript and cloned into the T7 expression vector pET28a(+) at the NdeI-XhoI sites. Overexpression of *M. tuberculosis* LeuRS from this construct generated a version of *M. tuberculosis* LeuRS with an

Example 1

A. 3-Aminomethyl-4-fluoro-7-(3-hydroxy-propoxy)-3H-benzo[c][1,2]oxaborol-1-ol; bis trifluoroacetic salt 6-Fluoro-2,3-dimethoxy-benzaldehyde

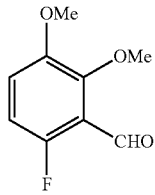 [SMILES: COc1ccc(F)c(C=O)c1OC]

To a solution of 4-fluoro-1,2-dimethoxy-benzene (20.0 g, 128.07 mmol) in anhydrous THF (200 mL) under nitrogen at −78° C. was added dropwise a 2.5M solution in hexane of n-BuLi (102.4 mL, 256.14 mmol) for duration 30 min and the reaction mixture was further stirred at the same temperature for 3 h. The reaction mixture was quenched carefully with DMF (100 mL) at −65° C. to −40° C. and left overnight. 2N HCl (300 mL) was added dropwise at −60° C. and the mixture stirred for 30 min. The two layers were separated and the aqueous layer extracted with EtOAc. The combined organic layers were washed with water and brine, dried over MgSO$_4$, filtered and concentrated in vacuo. Purification was completed by flash column chromatography (20% EtOAc/hexane). Yield 18.0 g (85%). $^1$H NMR (400 MHz, CHLOROFORM-d) δ ppm 10.39 (s, 1H), 7.09 (dd, J=9.4, 5.1 Hz, 1H), 6.84 (t, J=9.6 Hz, 1H), 3.98 (s, 3H), 3.88 (s, 3H). $^{19}$F NMR (376 MHz, CHLOROFORM-d): −126 ppm.

6-Fluoro-2,3-dihydroxy-benzaldehyde

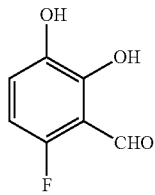 [SMILES: O=Cc1c(F)ccc(O)c1O]

To a solution of 6-fluoro-2,3-dimethoxy-benzaldehyde (18.0 g, 97.74 mmol) in anhydrous dichloromethane (100 mL) under nitrogen at −60° C. was added dropwise BBr$_3$.OEt$_2$ (195 mL, 195.48 mmol) over 30 min and the solution was allowed to warm up to r.t and stirred for 4 h. The reaction mixture was cooled to −60° C. and 2N HCl (250 mL) was carefully added drop wise. The mixture was stirred at r.t overnight. The two layers were separated and the aqueous layer extracted with DCM. The combined organic layers were washed with water, sat. NaHCO$_3$ solution, water and brine and dried over MgSO$_4$. The solvent was removed in vacuo to provide the title compound which was used in the next step without further purification. Yield 11.15 g (74%). $^1$H NMR (400 MHz, CHLOROFORM-d) δ ppm 11.53 (s, 1H), 10.23 (s, 1H), 7.11 (dd, J=8.8, 5.3 Hz, 1H), 6.57 (t, J=9.6 Hz, 1H), 5.48 (s, 1H). $^{19}$F NMR (376 MHz, CHLOROFORM-d): −132 ppm.

3-(3-Benzyloxy-propoxy)-6-fluoro-2-hydroxy-benzaldehyde

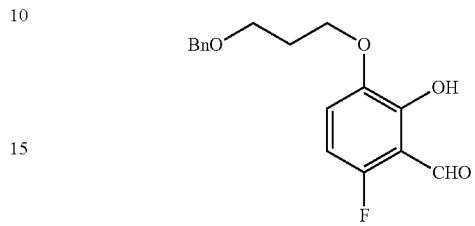

To a solution of 6-fluoro-2,3-dihydroxy-benzaldehyde (11.15 g, 71.42 mmol) in anhydrous DMSO (88 mL) under nitrogen were added sequentially sodium t-butoxide (13.72 g, 142.84 mmol) and benzyl-3-bromopropyl ether (17.29 g, 78.56 mmol) and the reaction mixture stirred at rt for 18 h. The mixture was diluted with water (400 mL) and extracted with EtOAc (4×100 mL). The combined organic layer was washed with water and brine, dried over MgSO$_4$, filtered and concentrated in vacuo. Purification was completed by flash chromatography (20% EtOAc/hexane). Yield 11.5 g (77%). $^1$H NMR (400 MHz, CHLOROFORM-d) δ ppm 11.62 (s, 1H), 10.23 (s, 1H), 7.42-7.16 (m, 5H), 7.05 (dd, J=8.8, 5.3 Hz, 1H), 6.54 (t, J=9.6 Hz, 1H), 4.52 (s, 2H), 4.13 (t, J=6.3 Hz, 2H), 3.68 (t, J=6.1 Hz, 2H), 2.12 (quin, J=6.2 Hz, 2H). $^{19}$F NMR (376 MHz, CHLOROFORM-d): −132 ppm.

Trifluoro-methanesulfonic acid 6-(3-benzyloxy-propoxy)-3-fluoro-2-formyl-phenyl ester

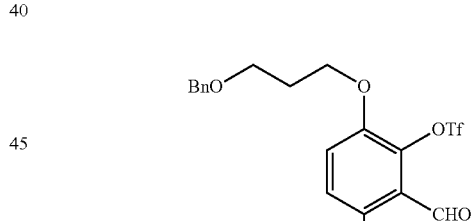

Trifluoromethanesulfonic anhydride (1.11 g, 3.94 mmol) was added dropwise to a solution of pyridine (389 mg, 4.92 mmol) and 3-(3-benzyloxy-propoxy)-6-fluoro-2-hydroxy-benzaldehyde (1 g, 3.28 mmol) in CH$_2$Cl$_2$ (5 mL) at 0° C. (bath temp). The reaction mixture was then allowed to warm to rt and was stirred until complete consumption of starting material (as determined by TLC). Et$_2$O and 2 N HCl were then added. The organic layer was separated and washed with sat. NaHCO$_3$ then brine. The organic layer was dried (Na$_2$SO$_4$) and filtered through a short silica gel plug, washing with Et$_2$O. The filtrate was concentrated in vacuo to give 1.10 g of the desired triflate (yield 76%) that was used directly without further purification. $^1$H NMR (400 MHz, CHLOROFORM-d) δ ppm 10.32 (s, 1H), 7.44-7.21 (m, 7H), 4.51 (s, 2H), 4.18 (t, J=6.1 Hz, 2H), 3.68 (t, J=5.7 Hz, 2H), 2.14 (quin, J=5.8 Hz, 2H).

3-(3-Benzyloxy-propoxy)-6-fluoro-2-(4,4,5,5-tetramethyl-[1,3,2]dioxaborolan-2-yl)-benzaldehyde

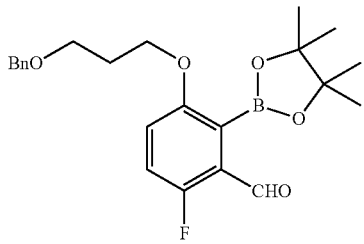 [SMILES: CC1(C)OB(c2c(OCCCOCc3ccccc3)ccc(F)c2C=O)OC1(C)C]

A solution of trifluoro-methanesulfonic acid 6-(3-benzyloxy-propoxy)-3-fluoro-2-formyl-phenyl ester (1.092 g, 2.50 mmol) in anhydrous 1,4-dioxane (10 mL) was added bis(pinacolato)diborane (953 mg, 3.75 mmol) and KOAc (736 mg, 7.50 mmol) at rt, then degassed with $N_2$ for 20 min. $PdCl_2$(dppf) (46 mg, 8 mol %) was added and the resulting solution was stirred at 100° C. until the reaction was complete. The solution was cooled to rt, filtered through Celite® or silica gel and concentrated in vacuo. The residue was taken up in EtOAc. The organic layer was then washed with $H_2O$ then brine, dried ($Na_2SO_4$), filtered, and concentrated in vacuo. The product was purified by flash chromatography (20% EtOAc/hexane) to give 0.5 g of the title compound along with detriflated by product ratio ~1:1 by H NMR spectrum. $^1$H NMR (400 MHz, CHLOROFORM-d) δ ppm 10.33 (s, 1H), 7.41-7.23 (m, 6H), 7.19 (d, J=9.4 Hz, 1H), 4.57-4.42 (m, 2H), 4.06 (t, J=6.3 Hz, 2H), 3.69-3.64 (m, 2H), 2.20-2.00 (m, 2H), 1.44 (s, 12H); $^{19}$F NMR (376 MHz, CHLOROFORM-d) δ ppm −73.72.

7-(3-Benzyloxy-propoxy)-4-fluoro-3-nitromethyl-3H-benzo[C][1,2]oxaborol-1-ol

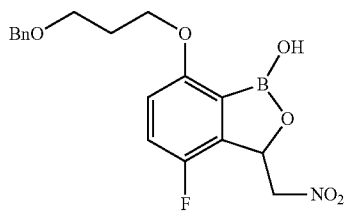 [SMILES: O=[N+]([O-])CC1OB(O)c2c(OCCCOCc3ccccc3)ccc(F)c21]

NaOH (48 mg, 1.20 mmol) was added to 3-(3-benzyloxy-propoxy)-6-fluoro-2-(4,4,5,5-tetramethyl-[1,3,2]dioxaborolan-2-yl)-benzaldehyde (500 mg, 1.2 mmol) in $H_2O$ (3 mL) at rt, and the reaction mixture was stirred at rt for 5 min. $MeNO_2$ (219 mg, 3.6 mmol) was added dropwise and the mixture was stirred at rt for 16 h. The reaction mixture was acidified with 2 N HCl and extracted with EtOAc. The organic fraction was washed with $H_2O$ then brine, dried ($MgSO_4$), and concentrated in vacuo. Purification was accomplished by flash chromatography (10-40% EtOAc/hexane) to give 120 mg of the title compound by $^1$H NMR spectrum. $^1$H NMR (400 MHz, CHLOROFORM-d) δ ppm 7.40-7.22 (m, 5H), 7.11 (t, J=8.8 Hz, 1H), 6.81 (t, J=8.6 Hz, 1H), 5.93 (dd, J=9.0, 2.3 Hz, 1H), 4.99 (dd, J=13.1, 2.5 Hz, 1H), 4.62-4.53 (m, 2H), 4.43 (dd, J=12.9, 9.0 Hz, 1H), 4.19-4.01 (m, 2H), 3.66 (dt, J=15.9, 5.7 Hz, 2H), 2.18-1.94 (m, 2H); $^{19}$F NMR (376 MHz, CHLOROFORM-d) δ ppm −72.81 (s, 1F); MS (ESI) m/z=374 (M−1, negative).

3-Aminomethyl-4-fluoro-7-(3-hydroxy-propoxy)-3H-benzo[c][1,2]oxaborol-1-ol; bis-trifluoroacetic acid salt

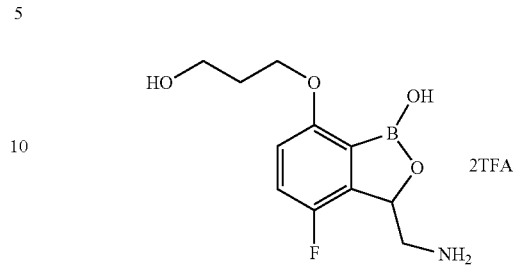

A mixture of 7-(3-benzyloxy-propoxy)-4-fluoro-3-nitromethyl-3H-benzo[C][1,2]oxaborol-1-ol (120 mg, 0.32 mmol) and 20% Pd(OH)$_2$ (120 mg, 1:1 w/w substrate to catalyst) in AcOH (10 mL) was shaken under an atmosphere of $H_2$ (45-50 psi) in a Parr shaker. Once the reaction was complete, the mixture was filtered through Celite®. The filtrate was concentrated in vacuo to give a gummy material. Remaining AcOH was removed by co-evaporation with toluene (3×) to give the amine. Purification by preparative HPLC (0.1% aq $CF_3CO_2H/CH_3CN$) produced 12 mg of the title compound as a white solid (yield 8.4%). $^1$H NMR (400 MHz, DMSO-d$_6$) δ ppm 9.14 (br. s., 1H), 8.02 (br. s., 3H), 7.25 (d, J=7.8 Hz, 1H), 6.93 (d, J=7.4 Hz, 1H), 5.43 (br. s., 1H), 4.55 (br. s., 1H), 4.07 (br. s., 2H), 3.56 (br. s., 2H), 3.42-3.37 (m, 1H), 2.95 (br. s., 1H), 1.86 (br. s., 2H); $^{19}$F NMR (376 MHz, DMSO-d$_6$) δ ppm −73.90 (s, 6F), −131.51 (s, 1F); MS (ESI) m/z=256 (M+1, positive); HPLC purity: 95.65% (MaxPlot 200-400 nm), 96.63% (220 nm).

B. 3-(Aminomethyl)-4-chloro-7-(3-hydroxy-propoxy)benzo[c][1,2]oxaborol-1(3H)-ol hydrochloride 3-(3-Benzyloxy-propoxy)-2-hydroxy-benzaldehyde

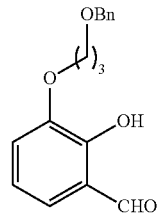

NaH (2.95 g, 72.4 mmol) was added to an ice-cold solution of 2,3-dihydroxybenzaldehyde (5.0 g, 36 mmol) in anhydrous DMSO (45 mL). Benzyl-3-bromopropyl ether (6.45 mL, 36.2 mmol) was then added and the mixture was stirred at rt for 12 h. The mixture was neutralized using 1 N HCl and then extracted with EtOAc. The organic fraction was washed with $H_2O$ and concentrated in vacuo. The residue was purified by flash chromatography (8:2 hexane/EtOAc) to give the title compound as a brown oil: yield 8.40 g (81%). $^1$H NMR (400 MHz, CDCl$_3$) δ (ppm): 9.93 (s, 1H), 7.36-7.23 (m, 6H), 7.20-7.16 (m, 2H), 6.98-6.91 (m, 1H), 4.53 (s, 2H), 4.19 (t, J=6.2 Hz, 2H), 3.70 (t, J=6.1 Hz, 2H), 2.19-2.16 (m, 2H).

3-(3-Benzyloxy-propoxy)-2-(4,4,5,5-tetramethyl-[1,3,2]dioxaborolan-2-yl)-benzaldehyde

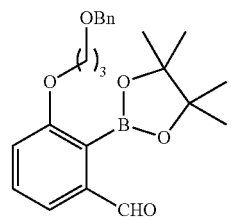

Trifluoromethanesulfonic anhydride (4.60 mL, 27.9 mmol) was added dropwise to a solution of pyridine (3.42 mL, 42.5 mmol) and 3-(3-benzyloxy-propoxy)-2-hydroxy-benzaldehyde (7.6 g, 26 mmol) in $CH_2Cl_2$ (200 mL) at 0° C. (bath temp). The reaction mixture was then allowed to warm to rt and was stirred until complete consumption of starting material (as determined by TLC). $Et_2O$ and 2 N HCl were then added. The organic layer was separated and washed with sat. $NaHCO_3$ then brine. The organic layer was dried ($Na_2SO_4$) and filtered through a short silica gel plug, washing with $Et_2O$. The filtrate was concentrated in vacuo to give 8.60 g of the desired triflate (yield 77%) that was used directly without further purification. $^1H$ NMR (400 MHz, $CDCl_3$) δ (ppm): 10.23 (s, 1H), 7.54-7.47 (m, 1H), 7.43 (t, J=8.0 Hz, 1H), 7.36-7.22 (m, 6H), 4.52 (s, 2H), 4.23 (t, J=6.3 Hz, 2H), 3.71 (t, J=6.1 Hz, 2H), 2.21-2.17 (m, 2H).

A solution of trifluoro-methanesulfonic acid 2-(3-benzyloxy-propoxy)-6-formyl-phenyl ester (8.0 g, 19 mmol) in anhydrous 1,4-dioxane (160 mL) was added bis(pinacolato)diborane (9.71 g, 38.2 mmol) and KOAc (5.71 g, 57.4 mmol) at rt, then degassed with $N_2$ for 20 min. $PdCl_2(dppf)$ (1.39 g, 1.89 mmol) was added and the resulting solution was stirred at 100° C. until the reaction was complete. The solution was cooled to rt, filtered through Celite® or silica gel and concentrated in vacuo. The residue was taken up in EtOAc. The organic layer was then washed with $H_2O$ then brine, dried ($Na_2SO_4$), filtered, and concentrated in vacuo. The product was purified by flash chromatography (9:1 hexane/EtOAc) to give 4.80 g of the title compound (yield 43%) along with some pinacol contamination and was used without further purification. $^1H$ NMR (400 MHz, $CDCl_3$) δ (ppm): 9.93 (s, 1H), 7.46 (t, J=7.8 Hz, 1H), 7.41-7.36 (m, 1H), 7.35-7.24 (m, 5H), 7.08 (d, J=7.8 Hz, 1H), 4.50 (s, 2H), 4.10 (t, J=6.3 Hz, 2H), 3.67 (t, J=6.3 Hz, 2H), 2.11 (quin, J=6.2 Hz, 2H), 1.43 (s, 12H).

7-(3-Benzyloxy-propoxy)-3-nitromethyl-3H-benzo[c][1,2]oxaborol-1-ol

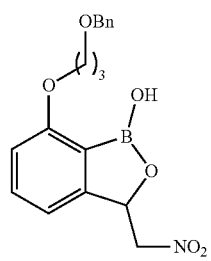

NaOH aq. (NaOH (3.64 g, 83 mmol) was added to 3-(3-benzyloxy-propoxy)-2-(4,4,5,5-tetramethyl-[1,3,2]dioxaborolan-2-yl)-benzaldehyde (36 g, 91 mmol) in $H_2O$ (180 mL), and THF (50 mL) at rt, and the reaction mixture was stirred at rt for 5 min. $MeNO_2$ (16.6 g, 273 mmol) was added dropwise and the mixture was stirred at rt for 16 h. The reaction mixture was acidified with 2 N HCl and extracted with EtOAc. The organic fraction was washed with $H_2O$ then brine, dried ($MgSO_4$), and concentrated in vacuo. Purification was accomplished by flash chromatography (1:1 hexane/EtOAc) to give 15.9 g of the title compound as a light yellow oil (yield 50%). $^1H$ NMR (400 MHz, DMSO-$d_6$) δ ppm: 9.05 (s, 1H), 7.44 (t, J=7.8 Hz, 1H), 7.35-7.20 (m, 5H), 7.06 (d, J=7.4 Hz, 1H), 6.88 (d, J=8.2 Hz, 1H), 5.70 (dd, J=9.4, 2.3 Hz, 1H), 5.29 (dd, J=13.7, 2.7 Hz, 1H), 4.53 (dd, J=13.3, 9.4 Hz, 1H), 4.45 (s, 2H), 4.11 (t, J=6.1 Hz, 2H), 3.60 (t, J=6.3 Hz, 2H), 2.04-1.91 (m, 2H); MS (ESI): m/z=356 (M−1, negative); HPLC purity: 99.35% (MaxPlot 200-400 nm), 97.32% (220 nm).

4-Chloro-7-(3-hydroxy-propoxy)-3-nitromethyl-3H-benzo[c][1,2]oxaborol-1-ol

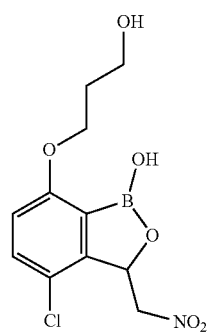 [SMILES: O=[N+]([O-])CC1OB(O)c2c(OCCCO)ccc(Cl)c21]

To 7-(3-benzyloxy-propoxy)-3-nitromethyl-3H-benzo[c][1,2]oxaborol-1-ol (1.1 g, 3.0 mmol) in glacial AcOH (10 mL) in cold water bath was added $SO_2Cl_2$ (0.7 mL, 9.07 mmol) dropwise over 5 minutes period. The resulting solution was stirred for 30 minutes at the same temperature then 1.5 h at room temperature. The solution was quenched with crushed ice and then diluted with EtOAc (100 mL). The organic layer was washed with water, dried over $Na_2SO_4$, filtered and concentrated under reduced pressure. To the crude residue in MeOH (20 mL) was added $Pd(OH)_2$ (10% w/w on carbon, 0.7 g), conc HCl was added until pH was 1, and the reaction vessel was pressurized to 40 psi with hydrogen for 30 minutes at room temperature. The resulting mixture was filtered through a pad of Celite® and washed with EtOAc. The filtrate was concentrated in vacuo, then the residue was purified by silica gel column chromatography (EtOAc:Hex, 1:1) providing the title compound (0.2 g, 24% in 2 steps). $^1H$ NMR (400 MHz, DMSO-$d_6$) δ ppm 9.31 (br. s., 1H), 7.49 (d, J=8.2 Hz, 1H), 6.98 (d, J=8.6 Hz, 1H), 5.76 (dd, J=8.2, 2.7 Hz, 1H), 5.33 (dd, J=13.2, 2.3 Hz, 1H), 4.70 (dd, J=13.0, 8.4 Hz, 1H), 4.55 (br. s., 1H), 4.15-4.05 (m, 2H), 3.61-3.55 (m, 2H), 1.95-1.77 (m, 2H).

3-Aminomethyl-4-chloro-7-(3-hydroxy-propoxy)-3H-benzo[c][1,2]oxaborol-1-ol hydrogen chloride

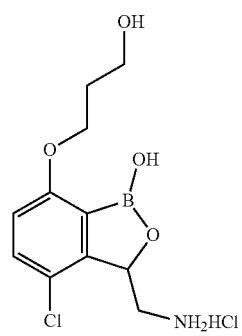

4-Chloro-7-(3-hydroxy-propoxy)-3-nitromethyl-3H-benzo[c][1,2]oxaborol-1-ol (105 mg, 0.35 mmol) in methanolic ammonia solution (2 M, 20 mL) was added Ra/Ni (0.15 g, 2800 Nickel slurry in water) and the reaction vessel was pressurized to 40 psi with hydrogen overnight at room temperature. The resultant mixture was filtered through a pad of Celite® and washed with EtOAc. The filtrate was concentrated in vacuo and the residue was added water (1 mL), followed by conc HCl to pH 1. The heterogeneous mixture was lyophilized provide the title compound (130 mg, quantitative) as a white solid. $^1$H NMR (400 MHz, DMSO-$d_6$) δ ppm 9.14 (br. s., 1H), 8.36 (br. s., 3H), 7.49 (d, J=8.2 Hz, 1H), 6.99 (d, J=8.2 Hz, 1H), 5.40 (d, J=7.0 Hz, 1H), 4.40 (br. s., 1H), 4.10 (br. s., 2H), 3.59 (br. s., 2H), ~3.30 (hidden, 1H), 2.89 (br. s., 1H), 1.89 (br.s, 2H); MS (ESI) m/z=272 (M+1, positive); HPLC purity: 96.92% (MaxPlot 200-400 nm), 97.96% (220 nm).

C. 3-Aminomethyl-7-ethoxy-4-fluoro-3H-benzo[c][1,2]-oxaborol-1-ol; hydrochloride 6-Fluoro-2,3-dimethoxy-benzaldehyde

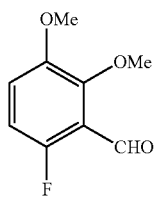 [SMILES: COc1ccc(F)c(C=O)c1OC]

To a cold (−78° C.) solution of 4-fluoro-1,2-dimethoxy-benzene (15.00 g, 96.05 mmol) in anhydrous THF (150 mL) was added n-BuLi (84.5 mL, 211.32 mmol, 2.5 M solution in hexanes) under nitrogen and stirred it for 3 h at −78° C. Quenched the reaction with DMF (75 mL) at −65° C., added 2N HCl (300 mL) dropwise and further stirred for 30 min. Two layers separation was observed. Aqueous layer was extracted with EtOAc. Combined organic layers were washed with water, brine and dried over MgSO$_4$. Filtered the ethyl acetate layer and concentrated it in vacuo. The title compound was purified by flash column chromatography using pure hexanes then 10 and 20% EtOAc in hexanes which provided 14.40 g (78.19 mmol, 82%) of the title compound as a white solid. $^1$H NMR (400 MHz, DMSO-$d_6$) δ ppm 10.23 (s, 1H), 7.36 (dd, J=9.0, 5.1 Hz, 1H), 7.03 (t, J=9.6 Hz, 1H), 3.87 (s, 3H), 3.83 (s, 3H); $^{19}$F NMR (376 MHz, DMSO-$d_6$) δ ppm −131.68--−131.66 (m, 1F).

6-Fluoro-2,3-dihydroxy-benzaldehyde

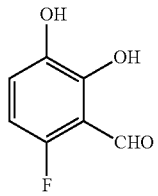 [SMILES: O=Cc1c(F)ccc(O)c1O]

To a cold (−78° C.) solution of 6-fluoro-2,3-dimethoxy-benzaldehyde (4.50 g, 24.43 mmol) in anhydrous dichloromethane (30 mL) was added BBr$_3$ (1M in DCM, 48.8 mL, 48.87 mmol) dropwise (duration 30 min). The reaction was warmed to room temperature and stirred for 4 h. Again cooled it to −78° C. and added 2N HCl (60 mL) to it dropwise. The reaction was stirred for overnight at room temperature and extracted with DCM. Combined organic layers were washed with water, sat. NaHCO$_3$ solution, brine and dried over MgSO$_4$. Filtration and removal of solvent provided 2.42 g (15.50 mmol, 64%) of the title compound as a yellow solid. This was used in the next step without further purification. $^1$H NMR (400 MHz, DMSO-$d_6$) δ ppm 10.22 (s, 1H), 7.04 (dd, J=8.6, 5.5 Hz, 1H), 6.61 (dd, J=10.4, 8.8 Hz, 1H); $^{19}$F NMR (376 MHz, DMSO-$d_6$) δ ppm −131.69--−131.65 (m, 1F).

3-Ethoxy-6-fluoro-2-hydroxy-benzaldehyde

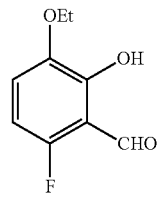 [SMILES: CCOc1ccc(F)c(C=O)c1O]

To a solution of 6-fluoro-2,3-dihydroxy-benzaldehyde (1.00 g, 6.40 mmol) in dry DMSO (10 mL) was added NaOBu$^t$ (1.23 g, 12.81 mmol) and ethyl bromide (0.77 g, 7.04 mmol) under N$_2$ and stirred at RT for 18 h. The resultant mixture was diluted with water, acidified to pH ~6 with 2N.HCl and extracted with EtOAc (4×25 mL). Combined organic layers were washed with water and brine and dried over MgSO$_4$. Filtration and removal of the solvent under reduced pressure provided 1.05 g (5.70 mmol, 89%) of the title compound as yellow solid. $^1$H NMR (400 MHz, CHLOROFORM-d) δ ppm 10.24 (s, 1H), 7.04 (dd, J=8.8, 5.3 Hz, 1H), 6.61-6.50 (m, 1H), 4.09 (q, J=7.0 Hz, 3H), 1.46 (t, J=7.0 Hz, 3H); $^{19}$F NMR (376 MHz, CHLOROFORM-d) δ ppm −132.19--−132.15 (m, 1F).

Trifluoro-methanesulfonic acid 6-ethoxy-3-fluoro-2-formyl-phenyl ester

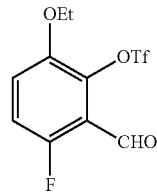 [SMILES: CCOc1ccc(F)c(C=O)c1OS(=O)(=O)C(F)(F)F]

To a cold (0° C.) solution of 3-ethoxy-6-fluoro-2-hydroxy-benzaldehyde (1.05 g, 5.70 mmol) in dry DCM (90 ml) was added pyridine (675 mg, 8.53 mmol) under nitrogen and stirred the reaction mixture at 0° C. for 10 min. Then added triflic anhydride (1.93 g, 6.84 mmol) slowly and continued stirring for 3 h at RT. Diluted the reaction with 1N.HCl (25 mL) and extracted with DCM (2×100 mL). The organic layer was washed with water and brine and dried over MgSO$_4$. Filtered and concentrated the filtrate. Purification of the residue by flash column chromatography with 5% ethyl acetate in hexanes gave 1.12 g, (3.54 mmol, 62%) of the title compound as a white solid. $^1$H NMR (400 MHz, CHLOROFORM-d) δ ppm 10.34 (s, 1H), 7.31-7.13 (m, 2H), 4.13 (q, J=7.0 Hz, 2H), 1.48 (t, J=7.0 Hz, 3H); $^{19}$F NMR (376 MHz, CHLOROFORM-d) δ ppm −128.15-−128.11 (m, 1F), −73.56 (s, 3F).

3-Ethoxy-6-fluoro-2-(4,4,5,5-tetramethyl-[1,3,2]dioxaborolan-2-yl)-benzaldehyde

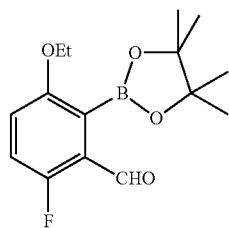 [SMILES: CCOc1ccc(F)c(C=O)c1B1OC(C)(C)C(C)(C)O1]

A solution of trifluoro-methanesulfonic acid 6-ethoxy-3-fluoro-2-formyl-phenyl ester (1.60 g, 5.05 mmol) in anhydrous THF (50 mL) was degassed for 40 min. Added bis(pinacolato)diborane (3.85 g, 15.17 mmol), KOAc (1.50 g, 15.17 mmol) and PdCl$_2$(dppf) (296 mg, 8 mol %) and stirred the reaction at 70° C. (bath temp) for 3 h. Another addition of bis(pinacolato)diborane (1.40 g, 5.51 mmol) and heating at 70° C. for 2 h completed the reaction. The resultant mixture was cooled to room temperature and filtered through a pad of Celite®. Concentrated the filtrate. Purification of the residue by flash column chromatography with hexanes and 5% EtOAc/hexanes yielded 1.65 g of title compound as white solid. $^1$H NMR confirms presence of title compound but with some impurities. It was used in next step without further purification. $^1$H NMR (400 MHz, CHLOROFORM-d) δ ppm 10.29 (s, 1H), 7.12-6.97 (m, 2H), 4.00 (q, J=7.0 Hz, 2H), 1.46 (s, 12H), 1.41 (t, J=6.8 Hz, 3H); $^{19}$F NMR (376 MHz, CHLOROFORM-d) δ ppm −133.71-−133.67 (m, 1F).

7-Ethoxy-4-fluoro-3-nitromethyl-3H-benzo[c][1,2]oxaborol-1-ol

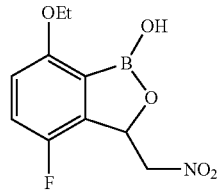 [SMILES: CCOc1ccc(F)c2c1B(O)OC2C[N+](=O)[O-]]

3-Ethoxy-6-fluoro-2-(4,4,5,5-tetramethyl-[1,3,2]dioxaborolan-2-yl)-benzaldehyde (1.65 g, 5.61 mmol) was added to a solution of NaOH (225 mg, 5.60 mmol) in H$_2$O (10 mL) and stirred for 10 min at RT. Added nitromethane (1.03 g, 16.83 mmol) dropwise and stirred for 4 h at RT. The reaction mixture was acidified with 4N HCl and extracted with ethyl acetate. Organic layer was washed with water, brine and dried over MgSO$_4$, filtered and concentrated in vacuo. Purification of the residue by flash column chromatography with 10 to 40% EtOAc/hexanes afforded 1.7 g of a mixture of compounds by $^1$H NMR spectrum. This mixture was used in next step without further purification. $^1$H NMR (400 MHz, CHLOROFORM-d) δ ppm 7.13 (t, J=8.8 Hz, 1H), 6.79 (dd, J=8.8, 2.5 Hz, 1H), 5.95 (d, J=9.0 Hz, 1H), 5.14 (s, 1H), 5.01 (dd, J=13.3, 2.3 Hz, 1H), 4.44 (dd, J=13.3, 9.0 Hz, 1H), 4.10 (q, J=6.8 Hz, 2H), 1.45 (t, J=6.8 Hz, 3H); $^{19}$F NMR (376 MHz, CHLOROFORM-d) δ ppm −131.00-−130.97 (m, 1F).

7-Ethoxy-4-fluoro-1-hydroxy-1,3-dihydro-benzo[c][1,2]oxaborol-3-ylmethyl)-carbamic acid tert-butyl ester

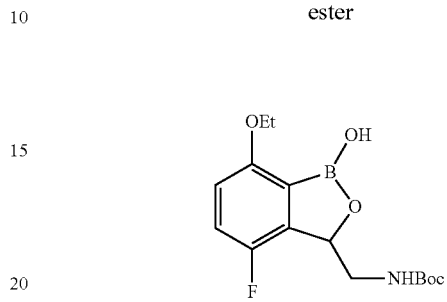

To a cold (0° C.) solution of 7-ethoxy-4-fluoro-3-nitromethyl-3H-benzo[c][1,2]oxaborol-1-ol (500 mg, 1.96 mmol) in dry MeOH (20 mL) was added (Boc)$_2$O (856 mg, 3.92 mmol) followed by NiCl$_2$.6H$_2$O (466 mg, 1.96 mmol) under nitrogen. Stirred the reaction mixture under nitrogen for 20 min and added NaBH$_4$ (445 mg, 11.76 mmol) in portions and left it for overnight at RT. Evaporated the solvent and diluted the reaction with 30 ml of ethyl acetate and filtered it through Celite. Filtrate was concentrated and residue was purified by flash column chromatography using 5% MeOH/DCM, but a mixture (950 mg) of products was obtained which was used in next step without further purification.

3-Aminomethyl-7-ethoxy-4-fluoro-3H-benzo[c][1,2]oxaborol-1-ol; hydrochloride

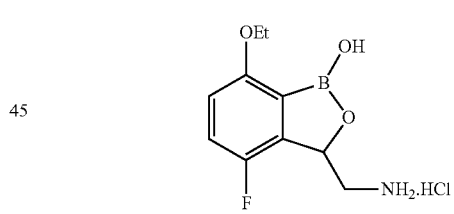

A solution of 7-ethoxy-4-fluoro-1-hydroxy-1,3-dihydro-benzo[c][1,2]oxaborol-3-ylmethyl)-carbamic acid tert-butyl ester (450 mg, 1.38 mmol) in 4M HCl (in 1,4-dioxane, 15 mL) was stirred at RT for overnight. The solvent was removed under reduced pressure. Recrystallization from EtOAc/hexanes provided 245 mg (0.93 mmol, 62%) of the title compound as white solid. $^1$H NMR (400 MHz, DMSO-d$_6$) δ ppm 9.15 (br. s., 1H), 8.20 (br. s., 3H), 7.26 (t, J=9.0 Hz, 1H), 6.95-6.85 (m, 1H), 5.45 (d, J=6.3 Hz, 1H), 3.30 (hidden, 1H), 4.05 (q, J=6.9 Hz, 2H), 2.89 (br. s., 1H), 1.30 (t, J=6.8 Hz, 3H); $^{19}$F NMR (376 MHz, DMSO-d$_6$) δ ppm −131.68-−131.66 (m, 1F); MS (ESI) m/z=226 (M+1, positive); HPLC purity: 91.87% (MaxPlot 200-400 nm), 90.33% (220 nm); Anal. Calcd for C$_{10}$H$_{14}$BClFNO$_3$ 0.5 H$_2$O: C, 44.40%; H, 5.59%; N, 5.18%. Found: C, 44.30%; H, 5.42%; N, 5.50%.

D. 3-(Aminomethyl)-4-chloro-7-ethoxybenzo[c][1,2]oxaborol-1(3H)-ol

2-Bromo-3-hydroxybenzaldehyde

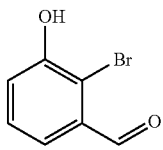

The suspension of 3-hydroxybenzaldehyde (5 g, 0.04 mol), iron powder (172 mg, 3 mmol) and sodium acetate (6.72 g, 0.08 mol) in acetic acid (40 mL) was warmed until a clear solution was obtained and then cooled to room temperature. To this mixture was dropwise added a solution of bromine in glacial acetic acid (10 mL) over 15 min. After the addition, the reaction mixture was stirred for 2 h and then poured into ice-water. The resulting mixture was extracted with dichloromethane (3×50 mL). The combined extracts were dried over anhydrous $Na_2SO_4$ and concentrated. The residue was re-crystallized from dichloromethane to afford the product (2.3 g, yield 28%). $^1$H NMR (400 MHz, DMSO-$d_6$) δ 10.30 (s, 1H), 7.54-7.51 (m, 1H), 7.39-7.35 (m, 1H), 7.31-7.27 (m, 1H), 5.90 (s, 1H).

2-Bromo-3-ethoxybenzaldehyde

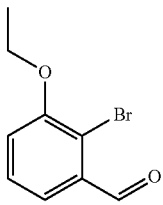

The suspension of 2-bromo-3-hydroxybenzaldehyde (120 g, 0.60 mol), $K_2CO_3$ (247 g, 1.79 mol) and bromoethane (135 mL, 1.79 mol) in DMF (700 mL) was stirred at 70° C. for 3 h. After the reaction was quenched with water (50 mL), the resulting mixture was extracted with EtOAc (3×60 mL). The combined organic layers were washed with water (50 mL) and aqueous LiCl solution (50 mL), dried over anhydrous $Na_2SO_4$ and concentrated to dryness in vacuo. The residue was purified by column chromatography on silica gel to give the target compound (128 g, yield 94%). $^1$H NMR (400 MHz, DMSO-$d_6$) δ 10.45 (s, 1H), 7.52-7.50 (d, 1H), 7.38-7.34 (t, 1H), 7.13-7.10 (d, 1H), 4.18-4.13 (m, 2H), 1.53-1.50 (m, 3H).

2-(2-Bromo-3-ethoxyphenyl)-1,3-dioxolane

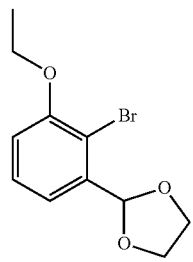

To a solution of 2-bromo-3-ethoxybenzaldehyde (128 g, 0.56 mol) and glycol (253 mL, 4.49 mol) in toluene (600 mL) was added p-toluenesulfonic acid (10 g, 0.06 mol). The reaction flask had a Dean and Stark condenser attached and the reaction mixture was refluxed to remove the water for 4 h. The reaction mixture was then cooled to room temperature and concentrated in vacuo. The residue was purified by column chromatography on silica gel to give the target compound (132 g, yield 86%).

Diisopropyl 2-(1,3-dioxolan-2-yl)-6-ethoxyphenylboronate

To the solution of 2-(2-bromo-3-ethoxyphenyl)-1,3-dioxolane (132 g, 0.48 mol) in anhydrous THF (500 mL) was dropwise added n-BuLi (2.5 M in THF, 386 mL, 0.97 mol) at −78° C. under nitrogen protection. The mixture was stirred at −78° C. for 2 h and then triisopropyl borate (227 mL, 0.97 mol) was dropwise added. The resulting mixture was stirred at this temperature for 4 h. After the reaction was quenched by adding saturated aqueous $NH_4Cl$ solution (200 mL), the resulting mixture was extracted with EtOAc (3×300 mL). The combined organic layers were washed with water (200 mL) and brine (200 mL), dried over anhydrous $Na_2SO_4$ and concentrated to dryness. The residue was purified by column chromatography on silica gel to give the target compound (136 g, yield 87%).

2-Ethoxy-6-formylphenylboronic acid

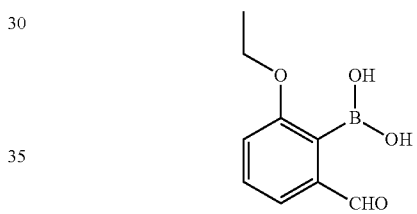

To the mixture of diisopropyl 2-(1,3-dioxolan-2-yl)-6-ethoxyphenylboronate (136 g, 0.42 mol) in THF (500 mL) was added diluted HCl (2N, 200 mL) slowly at room temperature with stirring. After stirred for 1.5 h at room temperature, the reaction mixture was basified with 20% aqueous solution of NaOH to pH=12 and then washed with EtOAc (2×100 mL). The aqueous layer was acidified by using the diluted HCl (2N) to pH=2 and then extracted with EtOAc (3×100 mL). The combined organic layers were dried over anhydrous $Na_2SO_4$ and concentrated to dryness. The residue was purified by column chromatography on silica gel to give the target compound as white solid (80 g, yield 83%). $^1$H NMR (400 MHz, DMSO-d) δ 9.93 (s, 1H), 7.92 (s, 2H), 7.45-7.48 (m, 2H), 7.23-7.28 (d, 1H), 4.01-4.06 (m, 2H), 1.69-1.20 (m, 3H).

7-Ethoxy-3-(nitromethyl)benzo[c][1,2]oxaborol-1(3H)-ol

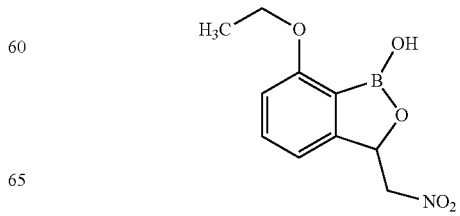

The mixture of 2-ethoxy-6-formylphenylboronic acid (80 g, 0.41 mol), NaOH (16.5 g, 0.41 mol) and CTAB (7.7 g, 20 mmol) in H$_2$O (100 mL) and THF (500 mL) was stirred for 0.5 h at room temperature After dropwise addition of nitromethane (14 mL, 2.4 mol), the reaction mixture was stirred at room temperature for 3 h. Then the cyclization was afforded by adding the diluted HCl (2 N) to pH=2 and then extracted with EtOAc (3×300 mL). The combined organic layers were washed with brine (250 mL), dried over anhydrous Na$_2$SO$_4$ and concentrated to dryness in vacuo. The residue was purified by column chromatography on silica gel to give the target compound as white solid (92 g, yield 94%). $^1$H NMR (400 MHz, DMSO-d$_6$ δ 9.06 (s, 1H), 7.46-7.43 (t, 1H), 7.07-7.05 (d, 1H), 6.89-6.87 (d, 1H), 5.71-5.69 (m, 1H), 5.31-5.27 (m, 1H), 4.57-4.51 (m, 1H), 4.12-4.07 (m, 2H), 1.34-1.30 (t, 3H).

4-Chloro-7-ethoxy-3-(nitromethyl)benzo[c][1,2]
oxaborol-1(3H)-ol

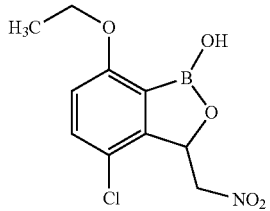 [SMILES: CCOc1ccc(Cl)c2c1B(O)OC2C[N+](=O)[O-]]

To a solution of 7-ethoxy-3-(nitromethyl)benzo[c][1,2] oxaborol-1(3H)-ol (42 g, 0.18 mol) in DMF (200 mL) at 80° C. was added a solution of NCS (11.8 g, 0.18 mol) in DMF (50 mL) in 30 min. The reaction was quenched with an aqueous solution of LiCl solution (500 mL) and the resulting mixture was extracted by EtOAc (3×250 mL). The combined organic layers were dried over anhydrous Na$_2$SO$_4$ and concentrated in vacuo. The residue was purified by column chromatography on silica gel to give the compound as white solid. (39.7 g, contaminated with 18% C6-Cl regioisomer). The mixture was then re-crystallized from Ether/PE (1/5) to give the pure compound (28 g, yield 46.3%). $^1$H NMR (400 MHz, DMSO-d$_6$) δ 9.32 (s, 1H), 7.50-7.48 (d, 1H), 6.98-6.96 (d, 1H), 5.77-5.74 (d, 1H), 5.35-5.31 (d, 1H), 4.73-4.67 (m, 1H), 4.12-4.07 (m, 2H), 1.34-1.28 (t, 3H).

3-(Aminomethyl)-4-chloro-7-ethoxybenzo[c][1,2]
oxaborol-1(3H)-ol hydrochloride

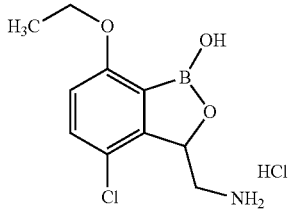 [SMILES: CCOc1ccc(Cl)c2c1B(O)OC2CN ; Cl]

A mixture of 4-chloro-7-ethoxy-3-(nitromethyl)benzo[c] [1,2]oxaborol-1(3H)-ol (47 g, 0.17 mol), Raney Ni (2 g) and 2 M NH$_3$ in EtOH (40 mL) in EtOH (200 mL) was stirred under an atmosphere of H$_2$ for 2 h and then filtrated. The filtrate was acidified by using 4.5 N HCl in EtOH (100 mL). After stirring for 30 min, the mixture was concentrated and the residue was washed with CH$_3$CN (2×50 mL) to give the product as white solid (43 g, yield 89%). $^1$H NMR (400 MHz, DMSO-d$_6$) δ 9.13 (s, 1H), 8.18 (s, 3H), 7.50-7.51 (d, 1H), 6.97-7.00 (d, 1H), 5.36-5.39 (m, 1H), 4.08-4.14 (m, 2H), 3.55-3.59 (m, 1H), 2.90-2.95 (m, 1H), 1.33-1.36 (m, 3H); MS (ESI) m/z=242 [M+H]$^+$.

E. 3-(Aminomethyl)-4-bromo-7-ethoxybenzo[c][1,2]
oxaborol-1(3H)-ol 2,2,2-trifluoroacetate salt 3-(Aminomethyl)-7-ethoxybenzo[c][1,2]oxaborol-1
(3H)-ol hydrochloride salt

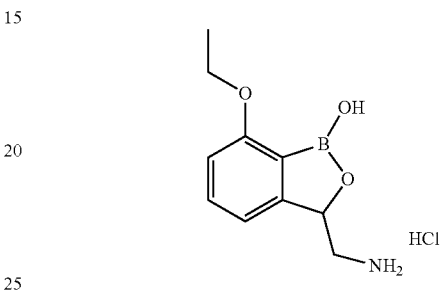

To the solution of 7-ethoxy-3-(nitromethyl)benzo[c][1,2] oxaborol-1(3H)-ol (2 g, 8.43 mmol), Raney Ni (200 mg) and 2 M NH$_3$ in EtOH (10 mL) in ethanol (35 mL) was shaken under an atmosphere of H$_2$ for 2 h at room temperature. The mixture was filtered through a bed of Celite and the filtrate was concentrated in vacuo. The crude amine was dissolved in EtOAc (10 mL) and HCl in Et$_2$O (30 mL) was added immediately. After 1 h, the suspension was filtered and the resulting solid was washed with acetonitrile/hexanes (2:1, 2×20 mL) to give the compound as white solid (1 g, yield 57.2%). $^1$H NMR (400 MHz, DMSO-d$_6$) δ 8.89 (s, 1H), 8.22 (s, 3H), 7.48-7.44 (t, 1H), 7.06-7.04 (d, 1H), 6.90-6.88 (d, 1H), 5.31-5.29 (m, 1H), 4.13-4.08 (m, 2H), 3.45-3.39 (m, 1H), 2.80-2.78 (m, 1H), 1.36-1.33 (m, 3H); MS (ESI) m/z=208 [M+H]$^+$.

tert-Butyl (7-ethoxy-1-hydroxy-1,3-dihydrobenzo[c]
[1,2]oxaborol-3-yl)methyl-carbamate

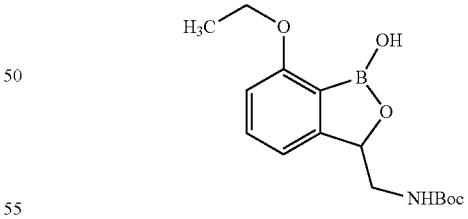

To the mixture of 3-(aminomethyl)-7-ethoxybenzo[c][1, 2]oxaborol-1(3H)-ol hydrochloride salt (300 mg, 1.23 mmol) and triethylamine (622 mg, 6.16 mmol) in dichloromethane (35 mL) at 0° C. was added di-tert-butyl dicarbonate (402.8 mg, 1.85 mmol) and the mixture was stirred for 2 h at room temperature. After the reaction was quenched with sat. NaHCO$_3$ (45 mL) and the resulting mixture was extracted with EtOAc (3×30 mL), the combined organic layers were dried over anhydrous Na$_2$SO$_4$ and concentrated in vacuo. The residue was purified by flash-column chromatography to give the product (320 mg, yield 84.6%).

tert-Butyl (4-bromo-7-ethoxy-1-hydroxy-1,3-dihydrobenzo[c][1,2]oxaborol-3-yl)-methylcarbamate

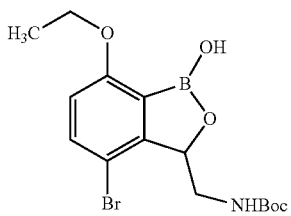 [SMILES: CCOc1ccc(Br)c2c1B(O)OC2CNC(=O)OC(C)(C)C]

To the solution of tert-butyl (7-ethoxy-1-hydroxy-1,3-dihydrobenzo[c][1,2]oxaborol-3-yl)methyl-carbamate (250 mg, 0.81 mmol) and 1-bromopyrrolidine-2,5-dione (173.9 mg, 0.98 mmol) in CH$_3$CN (50 mL) was added 2,2'-Azobis(2-methylpropionitrile) (10 mg) and the mixture was stirred for 1 h at 90° C. The reaction mixture was then concentrated in high vacuo and the residue was purified by prep-HPLC to give the product (200 mg, yield 63.6%). $^1$H NMR (400 MHz, DMSO-d$_6$) δ 8.90 (s, 1H), 7.55-7.53 (d, 1H), 6.85-6.82 (d, 1H), 5.08-5.07 (d, 1H), 4.11-4.07 (m, 2H), 3.82-3.79 (d, 1H), 3.06-3.03 (m, 1H), 1.39 (s, 9H), 1.30 (t, 3H); MS (ESI) m/z=387 [M+H]$^+$.

3-(Aminomethyl)-4-bromo-7-ethoxybenzo[c][1,2]oxaborol-1(3H)-ol 2,2,2-trifluoroacetate salt

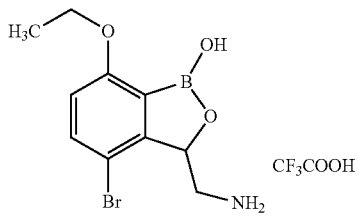 [SMILES: CCOc1ccc(Br)c2c1B(O)OC2CN ; "CF3COOH"]

The mixture of tert-butyl (4-bromo-7-ethoxy-1-hydroxy-1,3-dihydrobenzo[c][1,2]oxaborol-3-yl)-methylcarbamate (200 mg, 51.8 mmol) in 2,2,2-trifluoroacetic acid and dichloromethane (1:1, 20 mL) was stirred at room temperature for 1 h and concentrated to dryness (water bath <30° C.). The residue was washed with acetonitrile (2×5 mL) and the white solid was dried in high vacuo to give the product (190 mg, yield 91.6%). $^1$H NMR (400 MHz, DMSO-d$_6$) δ 9.12 (s, 1H), 8.04 (s, 3H), 7.65-7.62 (d, 1H), 6.94-6.92 (d, 1H), 5.27-5.25 (m, 1H), 4.13-4.08 (m, 2H), 3.64-3.61 (m, 1H), 2.99-2.92 (m, 1H), 1.36-1.33 (m, 3H); MS (ESI) m/z=287 [M+H]$^+$.

F. 3-(Aminomethyl)-7-ethoxy-4-methylbenzo[c][1,2]oxaborol-1(3H)-ol hydrochloride salt 7-Ethoxy-4-methyl-3-(nitromethyl)benzo[c][1,2]oxaborol-1(3H)-ol

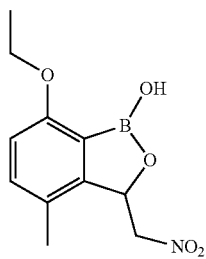 [SMILES: CCOc1ccc(C)c2c1B(O)OC2C[N+](=O)[O-]]

A mixture of 4-bromo-7-ethoxy-3-(nitromethyl)benzo[c][1,2]oxaborol-1(3H)-ol (200 mg, 0.63 mmol), tetramethylstannane (341.7 mg, 1.90 mmol) and Pd(PPh$_3$)$_4$ (Cat. 20 mg) in DMF (35 mL) was stirred overnight at 90° C. under N$_2$ protection. The reaction was quenched by adding ice-water and the resulting mixture was extracted with ethyl acetate (3×30 mL). The combined extracts were dried over anhydrous Na$_2$SO$_4$ and concentrated in vacuo. The residue was purified by prep-TLC to give the product (72 mg, yield 45.3%). $^1$H NMR (400 MHz, DMSO-d$_6$) δ 9.00 (s, 1H), 7.23-7.21 (d, 1H), 6.83-6.81 (d, 1H), 5.77-5.75 (m, 1H), 5.27-5.24 (m, 1H), 4.50-4.44 (m, 1H), 4.08-4.03 (m, 2H), 2.25 (s, 3H), 1.33-1.29 (t, 3H).

3-(Aminomethyl)-7-ethoxy-4-methylbenzo[c][1,2]oxaborol-1(3H)-ol hydrochloride salt

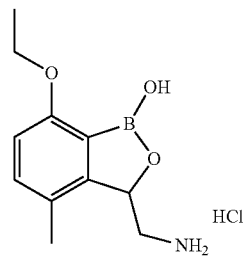 [SMILES: CCOc1ccc(C)c2c1B(O)OC2CN ; Cl]

A mixture of 7-ethoxy-4-methyl-3-(nitromethyl)benzo[c][1,2]oxaborol-1(3H)-ol (80 mg, 0.32 mmol), Raney Ni (50 mg) and NH$_3$/EtOH (2 mL) in EtOH (10 mL) was stirred under an atmosphere of H$_2$ for 2 h and then filtrated. The filtrate was acidified by using 4.5 N HCl in EtOH (15 mL). After stirring for 30 min, the mixture was concentrated in vacuo and the residue was washed with CH$_3$CN (2×3 mL) to give the product as white solid (39 mg, yield 47.5%). $^1$H NMR (400 MHz, DMSO-d$_6$) δ 8.80 (s, 1H), 8.15 (s, 3H), 7.24-7.22 (d, 1H), 6.83-6.81 (d, 1H), 5.37-5.35 (m, 1H), 4.08-4.03 (m, 2H), 3.36-3.28 (m, 1H), 2.73-2.70 (m, 1H), 2.23 (s, 3H), 1.34-1.30 (t, 3H); MS (ESI) m/z=222 [M+H]$^+$.

G. 3-(Aminomethyl)-7-ethoxy-4-ethylbenzo[c][1,2]oxaborol-1(3H)-ol

7-Ethoxy-3-(nitromethyl)-4-vinylbenzo[c][1,2]oxaborol-1(3H)-ol

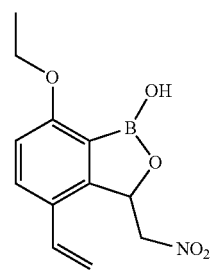

A mixture of 4-bromo-7-ethoxy-3-(nitromethyl)benzo[c][1,2]oxaborol-1(3H)-ol (900 mg, 2.85 mmol), vinyltributyltin (5.2 g, 53 mmol) and Pd(Ph$_3$P)$_4$ (230 mg, 0.2 mmol) in DMF (45 mL) was degassed for 15 min with N$_2$ and then stirred at 100° C. for 30 min in microwave reactor (Biotage).

After the reaction was quenched with ice-water, the resulting mixture was extracted with EtOAc (3×30 mL). The combined organic layers were washed with water (20 mL) and brine (20 mL), dried over anhydrous Na$_2$SO$_4$ and then concentrated to dryness in vacuo. The residue was purified by column chromatography on silica gel to give the compound (650 mg, yield 87%). $^1$H NMR (400 MHz, DMSO-d$_6$) δ 9.10 (s, 1H), 7.64-7.66 (d, 1H), 6.93-6.95 (d, 1H), 6.77-6.84 (m, 1H), 5.93-5.96 (d, 1H), 5.69-5.73 (d, 1H), 5.28-5.31 (d, 1H), 5.10-5.14 (d, 1H), 4.44-4.49 (m, 1H), 4.09-4.14 (m, 2H), 1.32-1.35 (m, 3H); MS (ESI) m/z=264 [M+H]$^+$.

3-(Aminomethyl)-7-ethoxy-4-vinylbenzo[c][1,2]oxaborol-1(3H)-ol

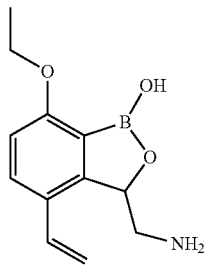 [SMILES: C=Cc1ccc(OCC)c2c1C(C[N+](=O)[O-])OB2O]

A mixture of 7-ethoxy-3-(nitromethyl)-4-vinylbenzo[c][1,2]oxaborol-1(3H)-ol (205 mg, 0.78 mmol), Raney-Ni (50 mg) and 2 M NH$_3$ in EtOH (5 mL) in EtOH (10 mL) was shaken under an atmosphere of H$_2$ for 2 h at room temperature. The mixture was filtered through a bed of Celite and the filtrate was concentrated in vacuo. The crude amine was dissolved in EtOAc (2 mL) and HCl in Et$_2$O (20 mL) was added immediately. After 1 h, the suspension was filtered and the resulting solid was used directly for the next step without further purification.

3-(Aminomethyl)-7-ethoxy-4-ethylbenzo[c][1,2]oxaborol-1(3H)-ol

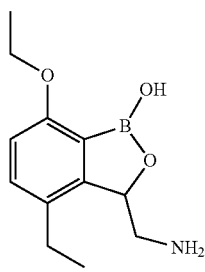 [SMILES: CCOc1ccc(CC)c2c1B(O)OC2CN]

To a suspension of 3-(aminomethyl)-7-ethoxy-4-vinylbenzo[c][1,2]oxaborol-1(3H)-ol (175 mg, 0.75 mmol) with Pd/C (40 mg) in EtOH (5 ml) was shaken under an atmosphere of H$_2$ for 2 h at room temperature. The mixture was filtered through a bed of Celite and the filtrate was concentrated in vacuo. The crude amine was dissolved in EtOAc (2 mL) and HCl in Et$_2$O (15 mL) was added immediately. After 1 h, the suspension was filtered and the resulting solid was washed with hexanes to give the target compound (23 mg, yield 13%). $^1$H NMR (400 MHz, DMSO-d$_6$) δ 8.81 (s, 1H), 8.18 (s, 3H), 7.31-7.29 (d, 1H), 6.68-6.88 (d, 1H), 5.38-5.40 (d, 1H), 4.04-4.09 (d, 2H), 3.30-3.35 (m, 1H), 2.66-2.71 (m, 1H), 1.31-1.34 (m, 3H), 1.15-1.17 (m, 3H); MS (ESI) m/z=236 [M+H]$^+$.

H. 3-(Aminomethyl)-7-ethoxy-4-phenylbenzo[c][1,2]oxaborol-1(3H)-ol

7-Ethoxy-3-(nitromethyl)-4-phenylbenzo[c][1,2]oxaborol-1(3H)-ol

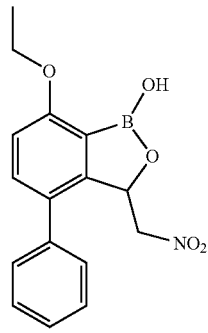 [SMILES: CCOc1ccc(-c2ccccc2)c2c1B(O)OC2C[N+](=O)[O-]]

A mixture of 4-bromo-7-ethoxy-3-(nitromethyl)benzo[c][1,2]oxaborol-1(3H)-ol (315 mg, 1 mmol), tributyl-phenyl-stannane (750 mg, 2 mmol) and Pd(Ph$_3$P)$_4$ (Cat.) in DMF (15 mL) was degassed for 15 min with N$_2$ and then stirred at 100° C. for 30 min in microwave reactor (Biotage). After the reaction was quenched with ice-water, the resulting mixture was extracted with EtOAc (3×40 mL). The combined organic layers were washed with water (20 mL) and brine (20 mL), dried over anhydrous Na$_2$SO$_4$ and then concentrated to dryness. The residue was purified by column chromatography on silica gel to give the compound as white solid (60 mg, yield 20%). $^1$HNMR (400 MHz, DMSO-d$_6$) δ 9.13 (s, 1H), 7.46-7.49 (m, 5H), 7.34-7.48 (m, 2H), 6.17-6.20 (m, 1H), 4.88-4.92 (m, 1H), 4.21-4.25 (m, 1H), 4.05-4.16 (m, 2H), 1.34-1.37 (m, 3H).

3-(Aminomethyl)-7-ethoxy-4-phenylbenzo[c][1,2]oxaborol-1(3H)-ol

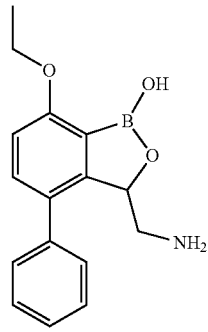 [SMILES: CCOc1ccc(-c2ccccc2)c2c1B(O)OC2CN]

A mixture of 7-ethoxy-3-(nitromethyl)-4-phenylbenzo[c][1,2]oxaborol-1(3H)-ol (60 mg, 0.19 mmol), Raney-Ni (~25 mg) and 2 M NH$_3$ in EtOH (2 mL) in EtOH (10 mL) was shaken under an atmosphere of H$_2$ for 2 h at room temperature. The mixture was filtered through a bed of Celite and the filtrate was concentrated in vacuo. The crude amine was dissolved in EtOAc (1 mL) and HCl in Et₂O (5 mL) was added immediately. After 1 h, the suspension was filtered and the resulting solid was washed with hexanes to give the compound as white solid (30 mg, yield 51%). ¹HNMR (400 MHz, DMSO-d₆) δ 8.89 (s, 1H), 8.04 (s, 3H), 7.43-7.46 (d, 5H), 7.36-7.38 (d, 1H), 6.98-7.00 (d, 1H), 5.78-5.81 (d, 1H), 4.09-4.14 (m, 2H), 2.56-2.59 (m, 1H), 2.24-2.30 (m, 1H), 1.33-1.36 (m, 3H); MS (ESI) m/z=284 [M+H]⁺.

I. 7-(4-Aminobutoxy)-3-(aminomethyl)-4-chlorobenzo[c][1,2]oxaborol-1(3H)-ol dihydrochloride tert-Butyl 4-hydroxybutylcarbamate

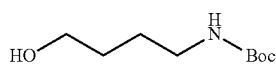 [SMILES: CC(C)(C)OC(=O)NCCCCO]

To a mixture of 4-aminobutan-1-ol (4.0 g, 45 mmol) and TEA (7.5 mL, 54 mmol) in DCM (200 ml) was added (Boc)₂O (10.2 g, 47.2 mmol). The reaction mixture was stirred for 2 h at room temperature and then washed with water (2×150 mL) and the solution of citric acid (100 mL). The organic layer was dried over anhydrous Na₂SO₄ and concentrated to give the product as yellow oil 7.5 g. (yield 88%).

4-(tert-Butoxycarbonyl)butyl methanesulfonate

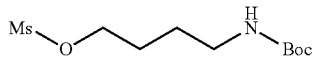

To a mixture of tert-butyl 4-hydroxybutylcarbamate (7.5 g, 40 mmol) and TEA (3.6 mL, 48 mmol) in DCM (100 mL) at 0° C. was dropwise added MsCl (6.6 mL, 48 mmol). The mixture was stirred at room temperature for 1 h and then washed with water (2×100 mL) and the solution of citric acid (100 mL). The organic layer was dried over anhydrous Na₂SO₄ and concentrated to give the product as yellow oil (10.0 g, yield 94%).

tert-Butyl 4-(2-bromo-3-formylphenoxy)butylcarbamate

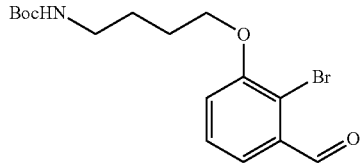 [SMILES: CC(C)(C)OC(=O)NCCCCOc1cccc(C=O)c1Br]

To a mixture of 2-bromo-3-hydroxybenzaldehyde (3.0 g, 15 mmol) and tert-butoxycarbonyl)butyl methanesulfonate (4.8 g, 18 mmol) in DMF (40 mL) was added K₂CO₃ (6.2 g, 45 mmol). The mixture was stirred at 80° C. for 45 min and quenched by addition of aqueous LiCl solution (80 mL). The mixture was extracted with EtOAc (2×80 mL) and the combined organic layers were dried over anhydrous Na₂SO₄ and then concentrated to give the crude product as brown oil (6.0 g).

tert-Butyl 4-(3-formyl-2-(4,4,5,5-tetramethyl-1,3,2-dioxaborolan-2-yl)phenoxy)-butylcarbamate

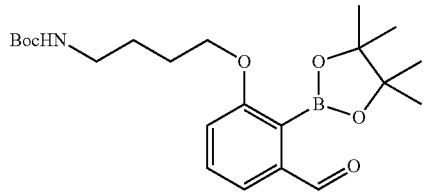 [SMILES: CC(C)(C)OC(=O)NCCCCOc1cccc(C=O)c1B1OC(C)(C)C(C)(C)O1]

A mixture of tert-butyl 4-(2-bromo-3-formylphenoxy)butylcarbamate (6.0 g, 16 mmol), KOAc (5.0 g, 48 mmol), (Pin)₂B₂ (7.7 g, 86 mmol) and Pb(dppf)Cl₂ (1.25 g, 1.6 mmol) in dioxane (100 mL) was degassed fro 15 min with N₂ and refluxed for 2 h under N₂ protection. The mixture was filtered and the filtrate was concentrated in vacuo. The residue was purified by chromatography on silica gel to give the product as yellow oil (3.5 g, yield 55%).

tert-Butyl-4-(1-hydroxy-3-(nitromethyl)-1,3-dihydrobenzo[c][1,2]oxa-borol-7-yloxy)butylcarbamate

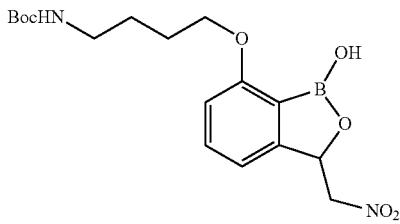 [SMILES: CC(C)(C)OC(=O)NCCCCOc1cccc2c1B(O)OC2C[N+](=O)[O-]]

To a solution of tert-butyl 4-(3-formyl-2-(4,4,5,5-tetramethyl-1,3,2-dioxaborolan-2-yl)-phenoxy)-butylcarbamate (3.5 g, 8.3 mmol) and CTAB (cat.) in THF (50 mL) was added MeNO₂ (2.8 mL, 49 mmol), followed by an aqueous solution of NaOH (0.36 g, 9.1 mmol) in H₂O (5 mL). The mixture was stirred at room temperature for 45 min. The cyclization was afforded by adding 2N HCl solution until pH=2 at 0° C. The reaction mixture was extracted with EtOAc (3×50 mL) and the organic layers were dried over anhydrous Na₂SO₄, and then concentrated in vacuo. The residue was purified by chromatography on silica gel (PE:EtOAc=3:1) to give the product as yellow oil (1.7 g, yield 53.6%). ¹H NMR (400 MHz, DMSO-d₆) δ 9.05 (s, 1H), 7.44-7.47 (t, 1H), 7.06-7.08 (d, 1H), 6.88-6.90 (d, 1H), 9.86 (t, 1H), 5.70-5.72 (m, 1H), 5.29-5.33 (m, 1H), 4.53-4.59 (m, 1H), 4.02-4.06 (t, 2H), 2.95-2.30 (m, 2H), 1.67-1.72 (m, 2H), 1.52-1.57 (m, 2H), 1.38 (s, 9H).

tert-Butyl-4-(4-chloro-1-hydroxy-3-(nitromethyl)-1,3-dihydrobenzo[c][1,2]oxaborol-7-yloxy)butylcarbamate

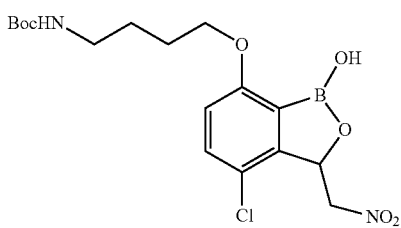

A mixture of tert-butyl 4-(1-hydroxy-3-(nitromethyl)-1,3-dihydrobenzo[c][1,2]oxaborol-7-yloxy)-butylcarbamate (640 mg, 1.7 mmol) in DMF (20 mL) was added NCS (226 mg, 1.7 mmol) in DMF (5 mL). The mixture was heated to 80° C. for 2 h. After the reaction was quenched with an aqueous LiCl solution (100 mL), the resulting mixture was extracted with EtOAc (3×50 mL). The combined organic layers were dried over anhydrous Na$_2$SO$_4$ and concentrated in vacuo. The residue was purified by prep-HPLC to give the product (280 mg, yield 67.5%). $^1$H NMR (400 MHz, DMSO-d$_6$) δ 9.29 (s, 1H), 7.47-7.49 (d, 1H), 6.96-6.98 (d, 1H), 6.80 (s, 1H), 5.74-5.77 (m, 1H), 5.31-5.35 (m, 1H), 4.67-4.72 (m, 1H), 4.02-4.05 (m, 2H), 2.94-2.99 (m, 2H), 1.68-1.72 (m, 2H), 1.50-1.56 (m, 2H), 1.36 (s, 9H).

tert-Butyl 4-(3-(aminomethyl)-4-chloro-1-hydroxy-1,3-dihydro-benzo[c][1,2]oxa-borol-7-yloxy)butyl-carbamate

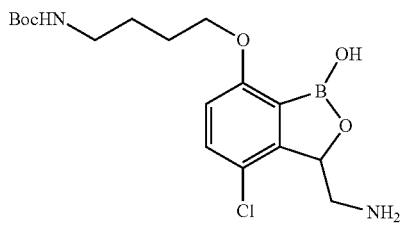 [SMILES: CC(C)(C)OC(=O)NCCCCOc1ccc(Cl)c2c1B(O)OC2C[N+](=O)[O-]]

A mixture of tert-butyl 4-(1-hydroxy-3-(nitromethyl)-1,3-dihydrobenzo[c][1,2]oxaborol-7-yl-oxy)-butylcarbamate (410 mg, 1 mmol), Raney-Ni (100 mg) and 2 N NH$_3$ in EtOH (3 mL) in EtOH (15 mL) was shaken under an atmosphere of H$_2$ for 2 h at room temperature. The mixture was filtered through a bed of Celite and the filtrate was concentrated in vacuo. The resulting solid was used directly for the next step.

7-(4-Aminobutoxy)-3-(aminomethyl)-4-chlorobenzo[c][1,2]oxaborol-1(3H)-ol dihydrochloride

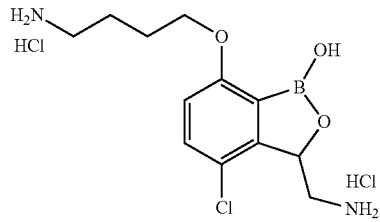 [SMILES: Cl ; NCCCCOc1ccc(Cl)c2c1B(O)OC2CN ; Cl]

To a mixture of the crude tert-butyl-4-(3-(aminomethyl)-4-chloro-1-hydroxy-1,3-dihydrobenzo[c]-[1,2]-oxa-borol-7-yloxy)butylcarbamate in DCM (5 mL) was added CF$_3$COOH (2 mL) at room temperature. The reaction mixture was stirred for 1 h and concentrated in vacuo. The crude amine was dissolved in EtOAc (1 mL) and HCl in Et$_2$O (10 mL) was added immediately. After 1 h, the suspension was filtered and the resulting solid was washed with hexanes to give the target compound as white solid (180 mg, yield: 42%). $^1$H NMR (400 MHz, DMSO-d$_6$) δ 9.16 (s, 1H), 8.28 (s, 3H), 8.03 (d, 3H), 7.49-7.51 (d, 1H), 6.99-7.01 (d, 1H), 5.38-5.40 (m, 1H), 4.05-4.08 (m, 2H), 3.56-3.59 (d, 1H), 2.84-2.91 (m, 3H), 1.71-1.83 (m, 4H); MS (ESI) m/z=285 [M+H]$^+$.

J. 3-(Aminomethyl)-7-(3-aminopropoxy)-4-chlorobenzo[c][1,2]oxaborol-1(3H)-ol tert-Butyl 3-bromopropylcarbamate

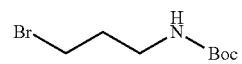

To a mixture of 3-bromopropan-1-amine (10.95 g, 50 mmol) and TEA (15.4 mL, 110 mmol) in DCM (100 ml) at 0° C. was added (Boc)$_2$O (11.4 g, 52.5 mmol). The reaction mixture was stirred at room temperature overnight and then washed with water (3×100 mL) and the solution of citric acid (100 mL). The organic layer was dried over anhydrous Na$_2$SO$_4$ and concentrated to give the product as yellow oil (9.0 g, yield 76%).

tert-Butyl 3-(2-bromo-3-formylphenoxy)propylcarbamate

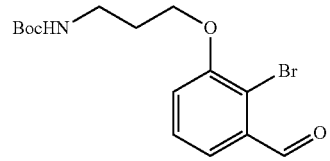 [SMILES: CC(C)(C)OC(=O)NCCCOc1cccc(C=O)c1Br]

A mixture of 2-bromo-3-hydroxybenzaldehyde (5 g, 24.9 mmol), 3-(tert-butoxy carbonylamino)-propyl methanesulfonate (7.55 g, 30 mmol) and Cs$_2$CO$_3$ (24 g, 75 mmol) in DMF (60 mL) was stirred at 50° C. for 3 h and quenched with water (600 mL). The resulting mixture was extracted with EtOAc (3×60 mL) and the combined organic layers were washed with brine (60 mL), dried over anhydrous Na$_2$SO$_4$ and then concentrated in vacuo. The residue was purified by column chromatography on silica gel (PE/EtOAc=10/1) to give the product (7.2 g, yield 81%). $^1$H NMR (400 MHz, CDCl$_3$) δ 10.43 (s, 1H), 7.53 (dd, J=7.8 Hz, 1.6 Hz, 1H), 7.37 (t, J=7.8 Hz, 1H), 7.12 (dd, J=8.2 Hz, 1.6 Hz, 1H), 5.16 (s, 1H), 4.15 (t, J=5.9 Hz, 2H), 3.42 (m, 2H), 2.10 (m, 2H), 1.44 (s, 9H); MS (ESI) m/z=358 [M+H]$^+$.

tert-Butyl 3-(3-formyl-2-(4,4,5,5-tetramethyl-1,3,2-dioxaborolan-2-yl)-phenoxy)propylcarbamate

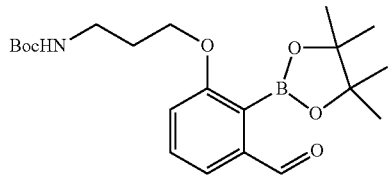 [SMILES: CC(C)(C)OC(=O)NCCCOc1cccc(C=O)c1B1OC(C)(C)C(C)(C)O1]

A solution of tert-butyl 3-(2-bromo-3-formylphenoxy)propylcarbamate (7.1 g, 20 mmol), B$_2$pin$_2$ (10 g, 40 mmol), Pd(dppf)Cl$_2$ (800 mg, 2 mmol) and KOAc (5.9 g, 60 mmol) in 1,4-dioxane (30 mL) was degassed with N$_2$ and stirred at 80° C. for 5 h. The mixture was cooled to room temperature and diluted with EtOAc (100 mL). The organic layer was washed with water (50 mL) and brine (50 mL), dried over anhydrous Na$_2$SO$_4$ and then concentrated. The residue was purified by chromatography on silica gel (PE/EtOAc=5/1) to give the product (3.1 g, yield 38.3%). $^1$H NMR (400 MHz, CDCl$_3$) δ 9.95 (s, 1H), 7.48 (t, J=7.8 Hz, 1H), 7.40 (m, 1H), 7.09 (d, J=8.2 Hz, 1H), 4.76 (s, 1H), 4.05 (t, J=6.3 Hz, 2H), 3.32 (m, 2H), 2.00 (m, 2H), 1.45 (s, 12H), 1.43 (s, 9H); MS (ESI) m/z=406 [M+H]$^+$.

tert-Butyl 3-(1-hydroxy-3-(nitromethyl)-1,3-dihydrobenzo[c][1,2]oxaborol-7-yloxy)-propylcarbamate

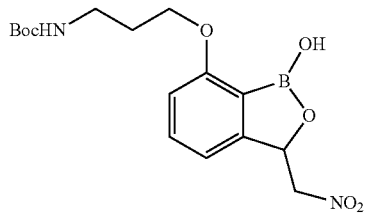 [SMILES: CC(C)(C)OC(=O)NCCCOc1cccc2c1B(O)OC2C[N+](=O)[O-]]

A mixture of tert-butyl 3-(3-formyl-2-(4,4,5,5-tetramethyl-1,3,2-dioxaborolan-2-yl)phenoxy)propylcarbamate (3.1 g, 8.47 mmol), MeNO$_2$ (775 mg, 12.7 mmol), CTAB (310 mg, 0.85 mmol) and NaOH (407 mg, 10 mmol) in THF (35 mL) and H$_2$O (8 mL) was stirred at room temperature for 3 h. The mixture was adjusted to pH 2-3 using 2N HCl and then stirred for 30 min. The mixture was extracted with EtOAc (2×80 mL). The organic layer was washed with water (30 mL) and brine (30 mL), dried over anhydrous Na$_2$SO$_4$ and then concentrated. The residue was purified by column chromatography on silica gel (PE/EtOAc=5/1) to give the product (2 g, yield 64.5%). $^1$H NMR (400 MHz, DMSO-d$_6$) δ 9.05 (s, 1H), 7.47 (t, J=7.8 Hz, 1H), 7.07 (d, J=7.4 Hz, 1H), 6.91 (m, 2H), 5.72 (dd, J=9.0, 2.7 Hz, 1H), 5.31 (dd, J=13.3, 2.7 Hz, 1H), 4.54 (dd, J=13.3, 9.4 Hz, 1H), 4.05 (t, J=6.3 Hz, 2H), 3.09 (m, 2H), 1.83 (m, 2H), 1.37 (s, 9H); MS (ESI) m/z=367 [M+H]$^+$.

tert-Butyl-4-(4-chloro-1-hydroxy-3-(nitromethyl)-1,3-dihydrobenzo[c][1,2]oxaborol-7-yloxy)propylcarbamate

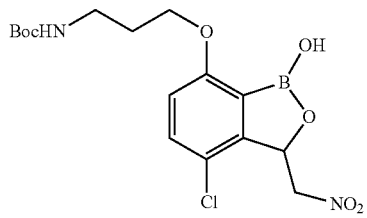 [SMILES: CC(C)(C)OC(=O)NCCCOc1ccc(Cl)c2c1B(O)OC2C[N+](=O)[O-]]

To a mixture of tert-butyl 4-(1-hydroxy-3-(nitromethyl)-1,3-dihydrobenzo[c][1,2]oxaborol-7-yl-oxy)propylcarbamate (2.9 g, 8 mmol) in DMF (35 mL) was added NCS (1.0 g, 8 mmol) in DMF (15 mL). The reaction mixture was heated to 80° C. for 2 h and then quenched with an aqueous LiCl solution (300 mL). The resulting mixture was extracted with EtOAc (3×100 mL). The combined organic layers were dried over anhydrous Na$_2$SO$_4$ and concentrated in vacuo. The residue was purified by prep-HPLC to give the product as white solid (480 mg, yield 15.2%). $^1$H NMR (400 MHz, DMSO-d$_6$) δ 9.28 (s, 1H), 7.49-7.51 (d, 1H), 6.96-6.98 (d, 1H), 6.85 (s, 1H), 5.74-5.77 (m, 1H), 5.31-5.35 (m, 1H), 4.67-4.72 (m, 1H), 4.03-4.06 (m, 2H), 3.07-3.11 (m, 2H), 1.82-1.86 (m, 2H), 1.37 (s, 9H); MS (ESI) m/z=401 [M+H]$^+$.

tert-Butyl 3-(3-(aminomethyl)-4-chloro-1-hydroxy-1,3-dihydro-benzo[c][1,2]oxa-borol-7-yloxy)propyl-carbamate

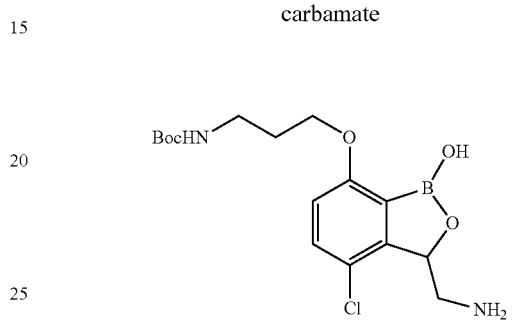

A mixture of tert-butyl 3-(4-chloro-1-hydroxy-3-(nitromethyl)-1,3-dihydrobenzo[c][1,2]oxaborol-7-yloxy)propylcarbamate (480 mg, 1.2 mmol), Raney-Ni (500 mg) and 2 M NH$_3$ in EtOH (3 mL) in EtOH (15 mL) was shaken under an atmosphere of H$_2$ for 2 h at room temperature. The mixture was filtered through a bed of Celite and the filtrate was concentrated in vacuo. The resulting solid was used directly for the next step.

3-(Aminomethyl)-7-(3-aminopropoxy)-4-chlorobenzo[c][1,2]oxaborol-1(3H)-ol

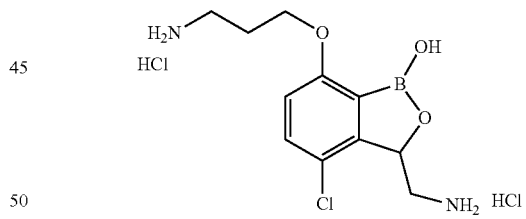

To a mixture of the crude tert-butyl 3-(3-(aminomethyl)-4-chloro-1-hydroxy-1,3-dihydrobenzo[c]-[1,2]oxaborol-7-yloxy)propylcarbamate in DCM (10 mL) was added CF$_3$COOH (2.0 mL) at 0° C. The reaction mixture was stirred for 1 h and concentrated in vacuo. The crude amine was dissolved in EtOH (2 mL) and HCl in Et$_2$O (2 mL) was added immediately. After 1 h, the mixture was concentrated in vacuo. The residue was re-crystallized by EtOH/Et$_2$O to give the target compound (173.4 mg, yield 42%). $^1$H NMR (400 MHz, DMSO-d$_6$) δ 9.28 (s, 1H), 8.36 (s, 3H), 8.17 (s, 3H), 7.50-7.52 (d, 1H), 6.98-7.00 (d, 1H), 5.39-5.42 (m, 1H), 4.13-4.16 (m, 2H), 3.56-3.59 (d, 1H), 2.98-2.99 (m, 2H), 2.87 (s, 1H), 2.04-2.10 (m, 2H); MS (ESI) m/z=271 [M+H]$^+$.

K. (R)-3-(Aminomethyl)-4-chloro-7-ethoxybenzo[c][1,2]oxaborol-1(3H)-ol hydrochloride and L. (S)-3-(Aminomethyl)-4-chloro-7-ethoxybenzo[c][1,2]oxaborol-1(3H)-ol hydrochloride

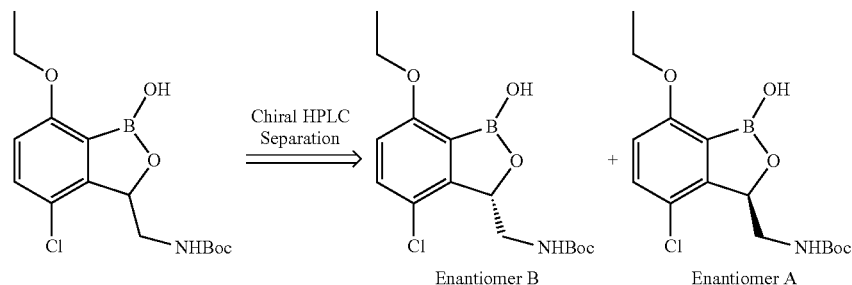

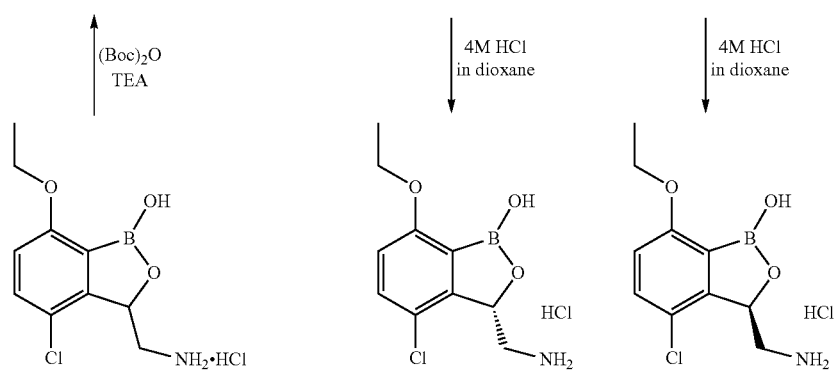

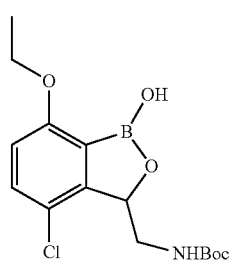 [SMILES: CCOc1ccc(Cl)c2c1B(O)OC2CNC(=O)OC(C)(C)C]

tert-Butyl((4-chloro-7-ethoxy-1-hydroxy-1,3-dihydrobenzo[c][1,2]oxaborol-3-yl)methyl)carbamate A solution of 3-(aminomethyl)-4-chloro-7-ethoxybenzo[c][1,2]oxaborol-1(3H)-ol hydrochloride (38.4 g, 0.16 mol) and Et$_3$N (47.8 g, 0.47 mol) in CH$_2$Cl$_2$ (350 mL) at 0° C. was added di-tert-butyl dicarbonate (172 g, 0.79 mol) and the reaction was stirred for 2 h at room temperature. After the reaction was quenched by addition of sat. NaHCO$_3$ (100 mL) and the resulting mixture was extracted with EtOAc (3×120 mL). The combined organic layers were dried over Na$_2$SO$_4$ and concentrated in vacuo. The residue was purified by column chromatography on silica gel to give the compound as white solid (27 g, yield 50%). $^1$H NMR (400 MHz, DMSO-d$_6$) δ 8.92 (s, 1H), 7.40-7.42 (d, 1H), 6.88-6.90 (d, 1H), 6.77-6.79 (m, 1H), 5.15-5.16 (d, 1H), 4.06-4.13 (m, 2H), 3.75-3.78 (d, 1H), 3.03-3.08 (m, 1H), 1.31-1.34 (m, 12H); MS (ESI) m/z=286 [M+H]$^+$.

(S)-tert-Butyl((4-chloro-7-ethoxy-1-hydroxy-1,3-dihydrobenzo[c][1,2]oxaborol-3-yl)methyl)carbamate and (R)-tert-butyl((4-chloro-7-ethoxy-1-hydroxy-1,3-dihydrobenzo[c][1,2]oxaborol-3-yl)methyl)carbamate

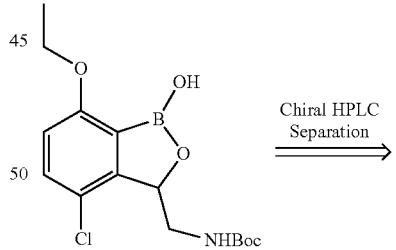

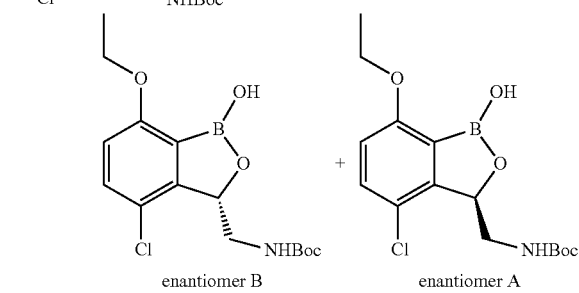

25.7 g of tert-butyl((4-chloro-7-ethoxy-1-hydroxy-1,3-dihydrobenzo[c][1,2]oxaborol-3-yl)methyl)carbamate dissolved in acetonitrile (10 mg/ml) was resolved via chiral HPLC using ChiralPak AD-H (250×30 mm I.D.) and SF $CO_2$/methanol as eluent. Flow rate is 70 mL/min. UV detection was monitored at 220 nm. Two peaks were collected and evaporated to give 10.65 g of enantiomer A (faster eluting isomer) and 10.15 g of enantiomer B (slower eluting isomer). Analysis of the pooled fractions using a ChiralPak AD-3 (150×4.6 mm I.D.) and the same mobile phase showed enantiomer A with a retention time of 3.12 min and 98.7% e.e, and enantiomer B with a retention time of 3.44 min and 98.5% e.e.

(R)-3-(Aminomethyl)-4-chloro-7-ethoxybenzo[c][1,2]oxaborol-1(3H)-ol hydrochloride

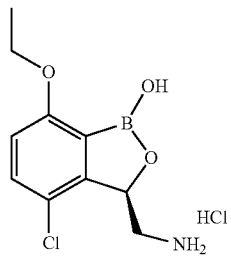

Enantiomer A (7.0 g, 20.5 mmol) was dissolved in 30 mL of dioxane and treated with 4M HCl (26.7 mL, 106.6 mmol) in dioxane. The reaction mixture was stirred at room temperature for overnight until the reaction was completed indicated by LC/MS. After dioxane was removed in vacuo and diethyl ether was added, an off-white solid was collected and dried under high-vacuum. This material was re-dissolved in acetonitrile and water (1:1, v/v) and lyophilized to give 5.17 g of the title compound as an off-white solid. $^1$H NMR (400 MHz, DMSO-$d_6$) δ 9.11 (s, 1H), 8.22 (s, 3H), 7.47 (d, 1H), 6.95 (d, 1H), 5.34-5.37 (m, 1H), 4.06-4.11 (m, 2H), 3.53-3.56 (m, 1H), 2.89 (m, 1H), 1.30-1.34 (m, 3H); MS (ESI) m/z=242.0 [M+H]$^+$.

(S)-3-(Aminomethyl)-4-chloro-7-ethoxybenzo[c][1,2]oxaborol-1(3H)-ol hydrochloride

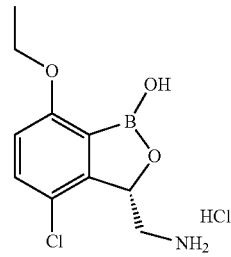 [SMILES: CCOc1ccc(Cl)c2c1B(O)O[C@@H]2CN ; Cl]

Enantiomer B (7.0 g, 20.5 mmol) was dissolved in 30 mL of dioxane and treated with 4M HCl (26.7 mL, 106.6 mmol) in dioxane. The reaction mixture was stirred at room temperature for overnight until the reaction was completed indicated by LC/MS. After dioxane was removed in vacuo and diethyl ether was added, an off-white solid was collected and dried under high-vacuum. This material was re-dissolved in acetonitrile and water (1:1, v/v) and lyophilized to give 5.23 g of the title compound as an off-white solid. $^1$H NMR (400 MHz, DMSO-$d_6$) δ 9.11 (s, 1H), 8.25 (s, 3H), 7.47 (d, 1H), 6.95 (d, 1H), 5.35-5.38 (m, 1H), 4.06-4.11 (m, 2H), 3.53-3.56 (m, 1H), 2.88 (m, 1H), 1.30-1.33 (m, 3H); MS (ESI) m/z=242.0 [M+H]$^+$.

M. (R)-3-(Aminomethyl)-4-fluoro-7-ethoxybenzo[c][1,2]oxaborol-1(3H)-ol hydrochloride and N. (S)-3-(Aminomethyl)-4-fluoro-7-ethoxybenzo[c][1,2]oxaborol-1(3H)-ol hydrochloride

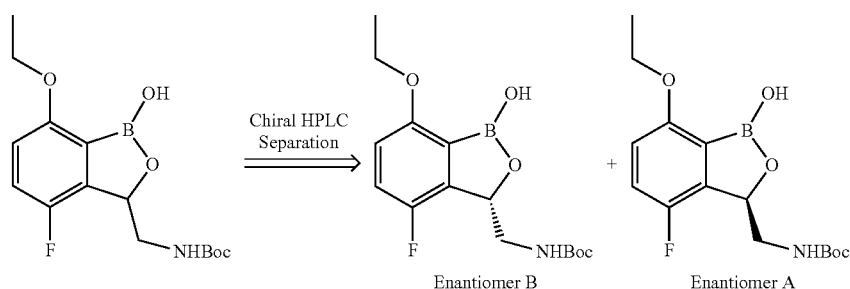

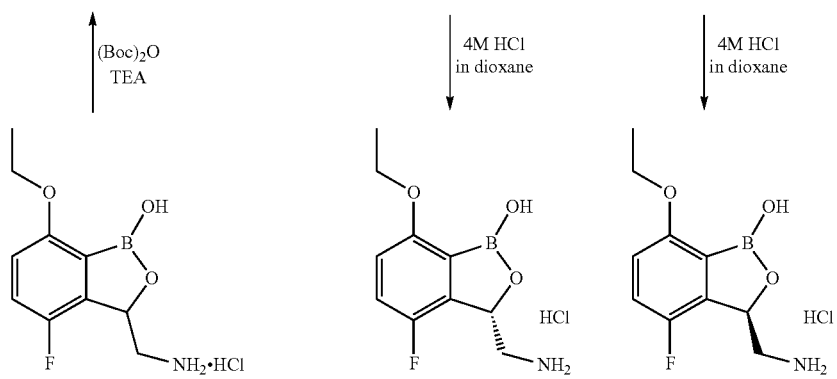

79 tert-Butyl((4-fluoro-7-ethoxy-1-hydroxy-1,3-dihydrobenzo[c][1,2]oxaborol-3-yl)methyl)carbamate

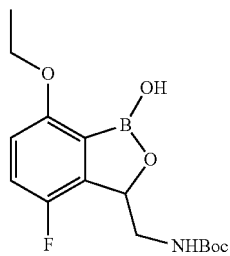 [SMILES: CCOc1ccc(F)c2c1B(O)OC2CNC(=O)OC(C)(C)C]

This compound was prepared from 3-aminomethyl-7-ethoxy-4-fluoro-3H-benzo[c][1,2]-oxaborol-1-ol, hydrochloride, using the similar procedure as described above.

(S)-tert-Butyl((4-fluoro-7-ethoxy-1-hydroxy-1,3-dihydrobenzo[c][1,2]oxaborol-3-yl)methyl)carbamate and (R)-tert-butyl((4-fluoro-7-ethoxy-1-hydroxy-1,3-dihydrobenzo[c][1,2]oxaborol-3-yl)methyl)carbamate

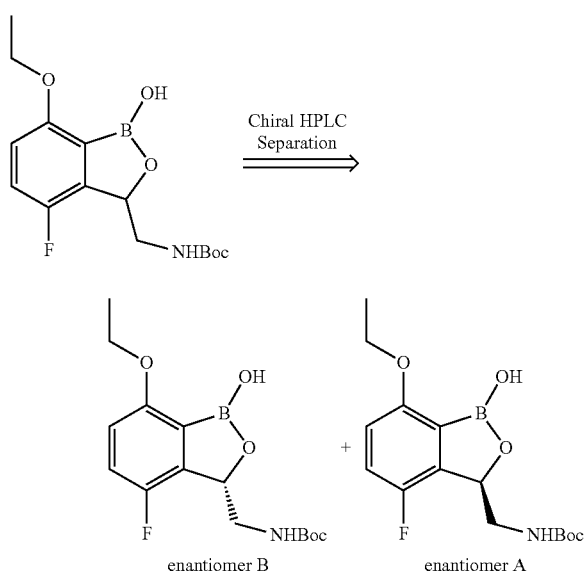

4.5 g of tert-butyl((4-fluoro-7-ethoxy-1-hydroxy-1,3-dihydrobenzo[c][1,2]oxaborol-3-yl)methyl)carbamate dissolved in ethanol (100 mg/ml) was resolved via chiral HPLC using ChiralCel OZ—H column (250×30 mm I.D.) and SF $CO_2$/hexane:ethanol (1:1) as eluent. Flow rate is 70 mL/min. UV detection was monitored at 220 nm. Two peaks were collected and evaporated to give 2.1 g of enantiomer A (faster eluting isomer) and 2.2 g of enantiomer B (slower eluting isomer). Analysis of the pooled fractions using a ChiralCel OZ—H (150×4.6 mm I.D.) and SF $CO_2$/ethanol (0.05% DEA) as mobile phase showed enantiomer A with a retention time of 2.66 min and 99.5% e.e, and enantiomer B with a retention time of 3.31 min and 98.1% e.e.

80

(R)-3-(Aminomethyl)-4-fluoro-7-ethoxybenzo[c][1,2]oxaborol-1(3H)-ol hydrochloride

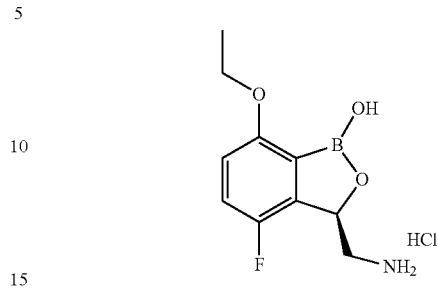

Enantiomer A (2.1 g) was treated with 200 mL of 1.6 N HCl in MeOH and stirred at room temperature for 5 hours until the reaction was completed indicated by LC/MS. After water (100 mL) was added, the residue was lyophilized overnight to give 1.40 g of the title compound as an off-white solid. $^1$H NMR (400 MHz, DMSO-$d_6$) δ ppm 9.16 (br. s., 1H), 8.34 (br. s., 3H), 7.26 (t, 1H), 6.70-6.92 (m, 1H), 5.48 (d, 1H), 4.06 (q, 2H), 3.35 (m, 1H), 2.88 (m, 1H), 1.30 (t, 3H); MS (ESI) m/z=226.1 (M+1, positive).

(S)-3-(Aminomethyl)-4-fluoro-7-ethoxybenzo[c][1,2]oxaborol-1(3H)-ol hydrochloride

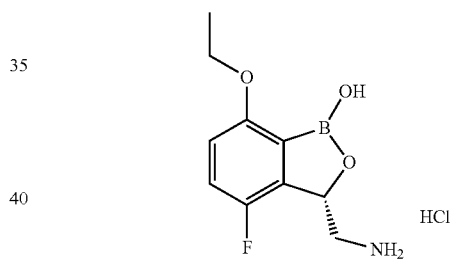

Enantiomer B (2.1 g) was treated with 200 mL of 1.6 N HCl in MeOH and stirred at room temperature for 5 hours until the reaction was completed indicated by LC/MS. After water (100 mL) was added, the residue was lyophilized overnight to give 1.43 g of the title compound as an off-white solid. $^1$H NMR (400 MHz, DMSO-$d_6$) δ ppm 9.16 (br. s., 1H), 8.31 (br. s., 3H), 7.26 (t, 1H), 6.70-6.92 (m, 1H), 5.48 (d, 1H), 4.06 (q, 2H), 3.35 (m, 1H), 2.88 (m, 1H), 1.31 (t, 3H); MS (ESI) m/z=226.1 (M+1, positive).

O. 3-Aminomethyl-5-chloro-7-(3-hydroxypropoxy)-3H-benzo[c][1,2]oxaborol-1-ol hydrochloride

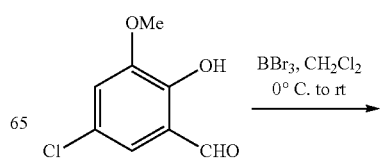

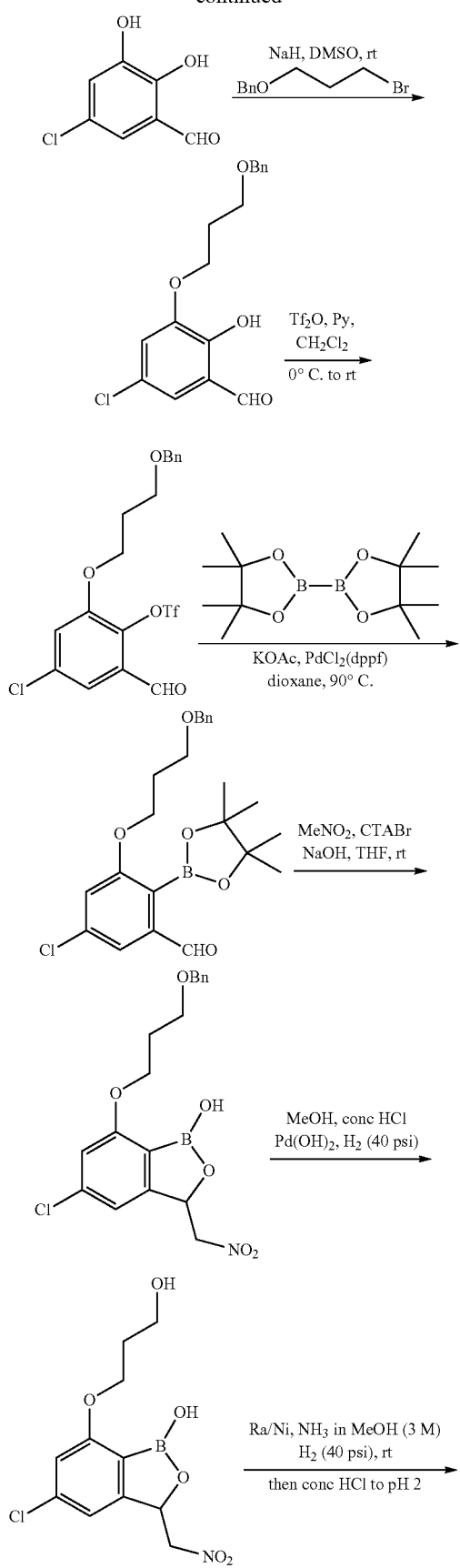

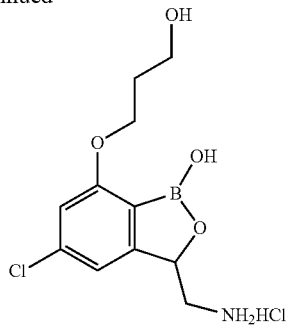

5-Chloro-2,3-dihydroxy-benzaldehyde

To a solution of 5-chloro-2-hydroxy-3-methoxy-benzaldehyde (7 g, 37.5 mmol) in anhydrous $CH_2Cl_2$ (200 mL) at 0° C. was added a solution of $BBr_3$ in $CH_2Cl_2$ (1 M, 93.7 mL, 93.7 mmol) and the reaction mixture was stirred overnight at room temperature. The solution was diluted with $CH_2Cl_2$ (200 mL), washed with water, brine, dried over $Na_2SO_4$, filtered and concentrated under reduced pressure generating the title compound (6.2 g, 36.0 mmol, 96%) as a light yellow solid. $^1H$ NMR (400 MHz, CHLOROFORM-d) δ ppm 11.02 (s, 1H), 9.83 (s, 1H), 7.18 (s, 1H), 7.14 (d, J=2.3 Hz, 1H), 5.71 (s, 1H).

3-(3-Benzyloxy-propoxy)-5-chloro-2-hydroxy-benzaldehyde

To a solution of 5-chloro-2,3-dihydroxy-benzaldehyde (3.1 g, 17.7 mmol) in anhydrous DMSO (20 mL) was added NaH (60% in mineral oil, 1.50 g, 35.4 mmol) portion-wise and the mixture was stirred for 30 minutes. The solution was cooled to 0° C. and a solution of 3-benzyloxy-1-bromopropane (3.1 mL, 17.7 mmol) in DMSO (3 mL) was added dropwise over 10 minutes period. The ice bath was removed. After overnight, the solution was diluted with EtOAc (100 mL), washed with water, brine, dried over $Na_2SO_4$, filtered and concentrated under reduced pressure. The product was purified by silica gel column chromatography (2:1 hexanes-EtOAc mobile phase) generating the title compound (5.3 g, 16.6 mmol, 94%) as a light yellow oil. $^1H$ NMR (400 MHz, CHLOROFORM-d) δ ppm 10.81 (s, 1H), 9.87 (s, 1H), 7.42-7.28 (m, 5H), 7.17 (s, 1H), 7.08 (s, 1H), 4.53 (s, 2H), 4.17 (t, J=6.2 Hz, 2H), 3.69 (t, J=5.8 Hz, 2H), 2.15 (t, J=6.2 Hz, 2H).

Trifluoro-methanesulfonic acid 2-(3-benzyloxy-propoxy)-4-chloro-6-formyl-phenyl ester To a solution of 3-(3-benzyloxy-propoxy)-5-chloro-2-hydroxy-benzaldehyde (5.3 g, 16.6 mmol) and pyridine (3.4 mL, 41.5 mmol) in $CH_2Cl_2$ (70 mL) at 0° C. was added $Tf_2O$ (3.1 mL, 18.3 mmol) drop-wise over 5 minutes period and the reaction mixture was stirred for 3 h at room temperature. The solution was diluted with $CH_2Cl_2$ (100 mL), washed with water, brine, dried over $Na_2SO_4$, then concentrated under reduced pressure. The product was purified by silica gel column chromatography (2:1 hexanes-EtOAc mobile phase) generating the title compound (3.8 g, 8.5 mmol, 51%) as a light yellow oil. $^1H$ NMR (400 MHz, CHLOROFORM-d) δ ppm 10.18 (s, 1H), 7.48 (d, J=2.3 Hz, 1H), 7.37-7.29 (m, 6H), 4.52 (s, 2H), 4.23 (t, J=6.2 Hz, 2H), 3.69 (t, J=5.8 Hz, 2H), 2.16 (t, J=6.0 Hz, 2H); $^{19}F$ NMR (376 MHz, CHLOROFORM-d) δ ppm −73.23 (s).

3-(3-Benzyloxy-propoxy)-5-chloro-2-(4,4,5,5-tetramethyl-[, 3,2]dioxaborolan-2-yl)-benzaldehyde To a solution of trifluoro-methanesulfonic acid 2-(3-benzyloxy-propoxy)-4-chloro-6-formyl-phenyl ester (3.8 g, 8.4 mmol) in anhydrous 1,4-dioxane (50 mL) was added bis(pinacolato)diborane (4.3 g, 16.9 mmol) and KOAc (2.5 g, 25.4 mmol) successively and the resulting solution was degassed with $N_2$ for 20 minutes. $PdCl_2(dppf)$ (0.5 g, 0.67 mmol) was added and the resulting mixture was stirred overnight at 90° C. The solution was diluted with EtOAc (100 mL), washed with water, brine, dried over $Na_2SO_4$, filtered and concentrated under reduced pressure. The product was purified by silica gel column chromatography (4:1 hexanes-EtOAc mobile phase) generating the title compound (3.4 g, 7.8 mmol, 92%) as a colorless oil. $^1$H NMR (400 MHz, CHLOROFORM-d) δ ppm 9.87 (s, 1H), 7.40-7.28 (m, 6H), 7.03 (br s, 1H), 4.50 (s, 2H), 4.09 (t, J=6.4 Hz, 2H), 3.70-3.60 (m, 2H), 2.10 (t, J=6.2 Hz, 2H), 1.42 (s, 12H).

7-(3-Benzyloxy-propoxy)-5-chloro-3-nitromethyl-3H-benzo[c][1,2]oxaborol-1-ol To a solution of 3-(3-benzyloxy-propoxy)-5-chloro-2-(4,4,5-trimethyl-[1,3,2]dioxaborolan-2-yl)-benzaldehyde (3.4 g, 7.8 mmol) and nitromethane (1.7 mL, 31.3 mmol) in THF (20 mL) was added a solution of NaOH (0.025 M, 40 mL). After 12 h, 2 N HCl was added until pH was 1. The solution was diluted with EtOAc (150 mL), washed with water, dried over $Na_2SO_4$, filtered and concentrated under reduced pressure. The product was purified by silica gel column chromatography (4:1 hexanes-EtOAc mobile phase) to give the title compound product (1.7 g, 56%) as a colorless gel. $^1$H NMR (400 MHz, CHLOROFORM-d) δ ppm 7.39-7.28 (m, 5H), 6.92 (s, 1H), 6.83 (s, 1H), 5.85 (br s, 1H), 5.81 (dd, J=8.5, 3.9 Hz, 1H), 4.70 (dd, J=13.2, 3.9 Hz, 1H), 4.59 (s, 2H), 4.47 (dd, J=13.0, 8.7 Hz, 1H), 4.21-4.07 (m, 2H), 3.71-3.60 (m, 2H), 2.10 (quin, J=5.7 Hz, 2H).

5-Chloro-7-(3-hydroxy-propoxy)-3-nitromethyl-3H-benzo[c][1,2]oxaborol-1-ol

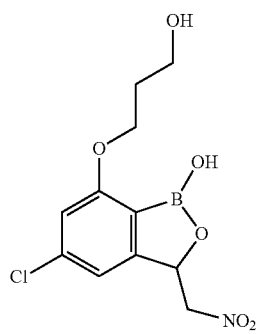 [SMILES: O=[N+]([O-])CC1OB(O)c2c(OCCCO)cc(Cl)cc21]

7-(3-Benzyloxy-propoxy)-5-chloro-3-nitromethyl-3H-benzo[c][1,2]oxaborol-1-ol (0.3 g, 0.91 mmol) in MeOH (30 mL) was added conc HCl (1 mL) and $Pd(OH)_2$ (10% w/w on carbon, 0.2 g) and the reaction vessel was pressurized to 40 psi with hydrogen for 30 minutes at room temperature. The mixture was filtered through a pad of Celite® and washed with EtOAc. The filtrate was concentrated in vacuo and the product was purified by prep. HPLC (C18 column, using acetonitrile and 0.1% AcOH/water solution gradient) provided the title compound (80 mg, 33%). $^1$H NMR (400 MHz, DMSO-$d_6$) δ ppm 9.19 (s, 1H), 7.22 (s, 1H), 6.97 (s, 1H), 5.71 (dd, J=8.9, 2.3 Hz, 1H), 5.32 (dd, J=13.2, 2.7 Hz, 1H), 4.64 (dd, J=13.6, 8.9 Hz, 1H), 4.53 (t, J=4.8 Hz, 1H), 4.12 (t, J=6.0 Hz, 2H), 3.57 (q, J=5.5 Hz, 2H), 1.86 (t, J=6.2 Hz, 2H).

3-Aminomethyl-5-chloro-7-(3-hydroxy-propoxy)-3H-benzo[c][1,2]oxaborol-1-ol hydrochloride

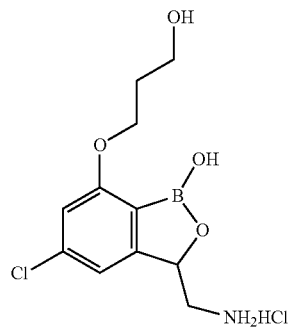

To a 5-chloro-7-(3-hydroxy-propoxy)-3-nitromethyl-3H-benzo[c][1,2]oxaborol-1-ol 7 (80 mg, 0.27 mmol) in methanolic ammonia solution (2 M, 20 mL) was added Ra/Ni (~0.1 g, 2800 Nickel slurry in water) and the reaction vessel was pressurized to 40 psi with hydrogen overnight at room temperature. The mixture was filtered through a pad of Celite® and washed with EtOAc. The filtrate was concentrated in vacuo and to the resulting residue was added water (1 mL), followed by conc HCl to pH 1. The heterogeneous mixture was lyophilized providing the title compound as a hygroscopic ivory solid (79 mg, quantitative). $^1$H NMR (400 MHz, DMSO-$d_6$) δ ppm 7.20 (s, 1H), 6.99 (s, 1H), 5.28 (dd, J=8.0, 2.5 Hz, 1H), 4.13 (t, J=6.0 Hz, 2H), 3.59 (t, J=6.0 Hz, 2H), 3.47 (dd, J=13.0, 2.5 Hz, 1H), 2.89 (dd, J=13.2, 8.6 Hz, 1H), 1.89 (t, J=6.0 Hz, 2H); MS (ESI) m/z=272 (M+1, positive); HPLC purity: 96.83% (MaxPlot 200-400 nm), 95.40% (220 nm).

P. 3-Aminomethyl-7-(3-hydroxy-propoxy)-6-methoxy-3H-benzo[c][1,2]oxaborol-1-ol hydrochloride

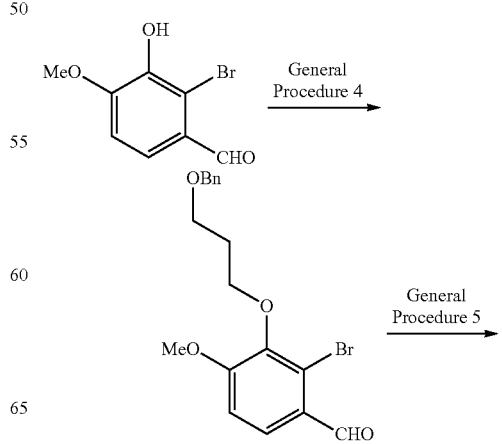

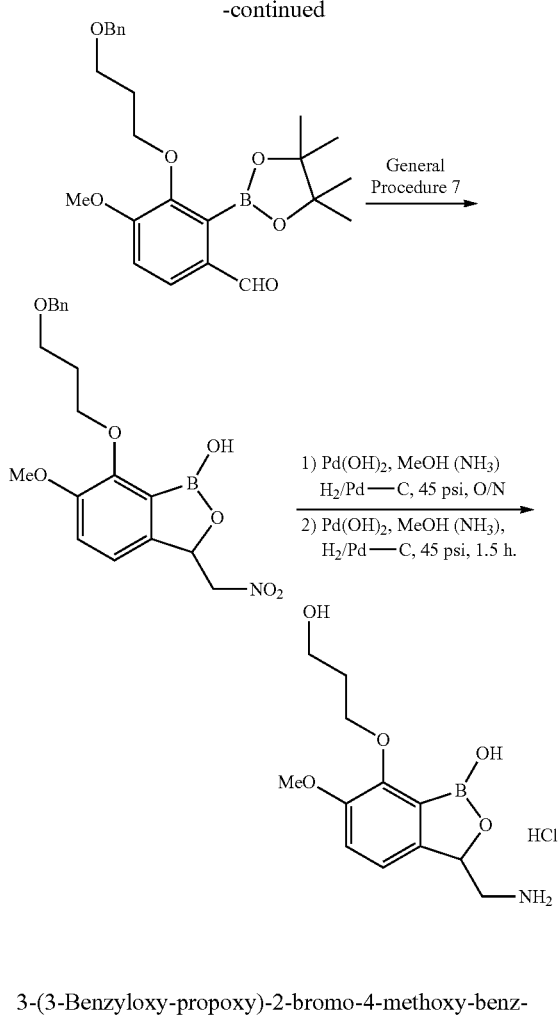

5H), 6.98 (d, J=8.2 Hz, 1H), 4.53 (s, 2H), 4.12 (t, J=6.4 Hz, 2H), 3.88 (s, 3H), 3.69 (t, J=6.4 Hz, 2H), 2.10 (quin, J=6.5 Hz, 2H), 1.44 (s, 12H).

7-(3-Benzyloxy-propoxy)-6-methoxy-3-nitromethyl-3H-benzo[c][1,2]oxaborol-1-ol

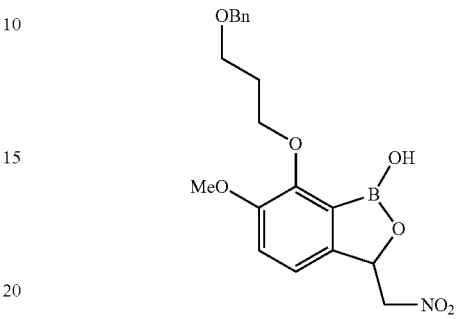

Synthesized according to the methods of general procedure 8 in U.S. Pat. Pub. No. 20090227541 (U.S. patent application Ser. No. 12/142,692) using the following reactants and amounts: 3-(3-benzyloxy-propoxy)-4-methoxy-2-(4,4,5,5-tetramethyl-[1,3,2]dioxaborolan-2-yl)-benzaldehyde (3.36 g, 7.88 mmol), nitromethane (1.28 mL, 23.66 mmol), NaOH (0.22 g, 5.52 mmol), THF (6 mL), water (18 mL). Purification: flash column chromatography (30% EtOAc/hexanes): yield 1.2 g (41%). $^1$H NMR (400 MHz, DMSO-$d_6$) δ (ppm): 9.36 (s, 1H), 7.40-7.22 (m, 5H), 7.22-7.04 (m, 2H), 5.68 (dd, J=9.4, 2.7 Hz, 1H), 5.29 (dd, J=13.4, 2.5 Hz, 1H), 4.52 (dd, J=13.3, 9.4 Hz, 1H), 4.45 (s, 2H), 4.25 (t, J=6.2 Hz, 2H), 3.75 (s, 3H), 3.61 (t, J=6.2 Hz, 2H), 1.92 (quin, J=6.5 Hz, 2H).

3-Aminomethyl-7-(3-hydroxy-propoxy)-6-methoxy-3H-benzo[c][1,2]oxaborol-1-ol; hydrochloride

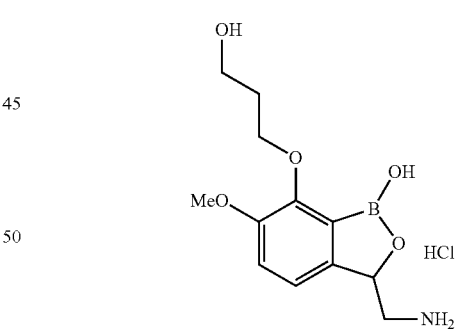

3-(3-Benzyloxy-propoxy)-2-bromo-4-methoxy-benzaldehyde

Synthesized according to the methods of general procedure 4 in U.S. Pat. Pub. No. 20090227541 (U.S. patent application Ser. No. 12/142,692) using the following reactants and amounts: 2-bromo-3-hydroxy-4-methoxy-benzaldehyde (1.0 g, 4.32 mmol), (3-bromo-propoxymethyl)-benzene (0.76 mL, 4.32 mmol), cesium carbonate (2.11 g, 6.5 mmol), DMF (30 mL). Purification: flash chromatography (10% EtOAc/hexanes): yield 1.54 g (95%). $^1$H NMR (400 MHz, CDCl$_3$) δ (ppm): 10.26 (s, 1H), 7.73 (d, J=8.6 Hz, 1H), 7.46-7.18 (m, 5H), 6.95 (d, J=8.6 Hz, 1H), 4.56 (s, 2H), 4.14 (t, J=6.1 Hz, 2H), 3.92 (s, 3H), 3.77 (t, J=6.2 Hz, 2H), 2.15 (quin, J=6.5 Hz, 2H); MS (ESI): m/z=381 (M+1, positive).

3-(3-Benzyloxy-propoxy)-4-methoxy-2-(4,4,5,5-tetramethyl-[1,3,2]dioxaborolan-2-yl)-benzaldehyde Synthesized according to the methods of general procedure 5 in U.S. Pat. Pub. No. 20090227541 (U.S. patent application Ser. No. 12/142,692) using the following reactants and amounts: 3-(3-benzyloxy-propoxy)-2-bromo-4-methoxy-benzaldehyde (14.82 g, 39 mmol), bis(pinacolato)diboran (14.86 g, 58.5 mmol), KOAc (11.46 g, 117 mmol), PdCl$_2$(dppf) (8.5 g, 11.7 mmol), dioxane (200 mL). Purification: flash column chromatography (15% EtOAc/hexanes): yield 3.42 g (22%). $^1$H NMR (400 MHz, CDCl$_3$) δ (ppm): 9.79 (s, 1H), 7.53 (d, J=8.2 Hz, 1H), 7.40-7.24 (m, To a solution of 7-(3-benzyloxy-propoxy)-6-methoxy-3-nitromethyl-3H-benzo[c][1,2]oxaborol-1-ol (0.5 g, 1.29 mmol) in methanolic ammonia (10 mL) was added palladium hydroxide (0.25 g, 45 wt %) in a hydrogenation bottle and the flask was charged with hydrogen at 45 psi for 18 h. The catalyst was filtered off and the solvent was evaporated under reduced pressure. In order to assure all the ammonia has been stripped off, the compound was subjected to the high vacuum for 1 h. The crude (0.4 g) obtained was further dissolved in methanol (15 mL) and transferred to a hydrogenation bottle and concentrated HCl (5-6 drops) was added to make it to pH 2. To this solution palladium hydroxide (0.11 g, 25 wt %) was added and the flask was charged with hydrogen to 45 psi for 1.5 h. The catalyst was filtered off through a pad of Celite and the solvent evaporated. Purification was accomplished by preparative HPLC generating 0.16 g (41%) of the title compound as a white solid. $^1$H NMR (400 MHz, DMSO-d$_6$) δ (ppm): 8.06 (br. s, 1H), 7.17 (d, J=8.2 Hz, 1H), 7.12-7.02 (m, 1H), 5.32 (dd, J=7.8, 2.3 Hz, 1H), 4.46-4.27 (m, 2H), 4.14 (t, J=4.5 Hz, 2H), 3.78 (s, 3H), 3.44 (dd, J=13.3, 2.7 Hz, 1H), 2.88 (dd, J=13.3, 8.2 Hz, 1H), 2.08-1.94 (m, 2H); MS (ESI): m/z=268 (M+1, positive); HPLC purity: 95.35% (MaxPlot 200-400 nm), 97.48% (220 nm).

Q. 3-Aminomethyl-7-(3-hydroxy-propoxy)-6-methyl-3H-benzo[c][1,2]oxaborol-1-ol; hydrochloride

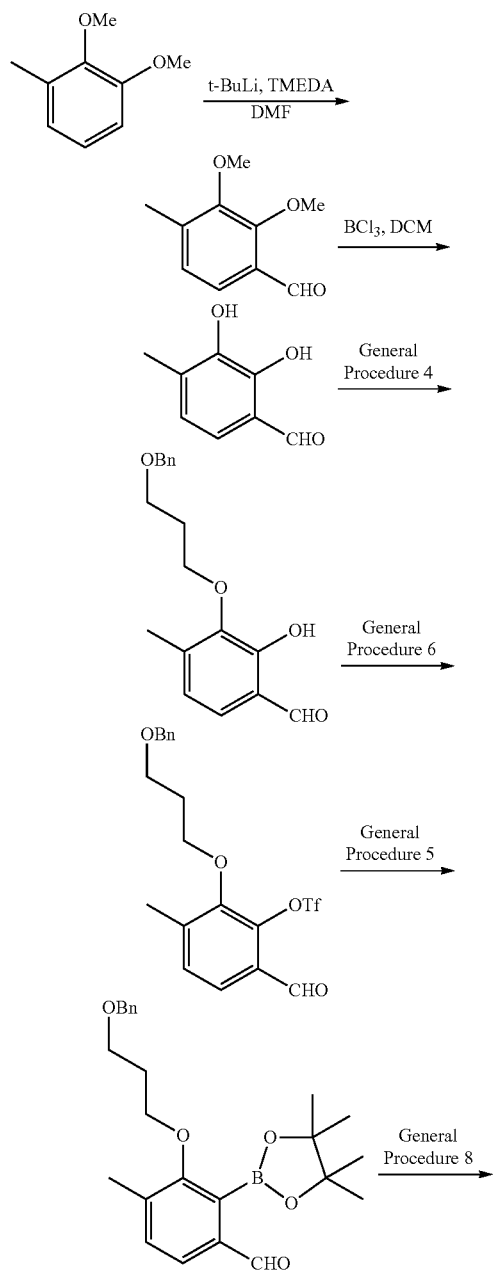

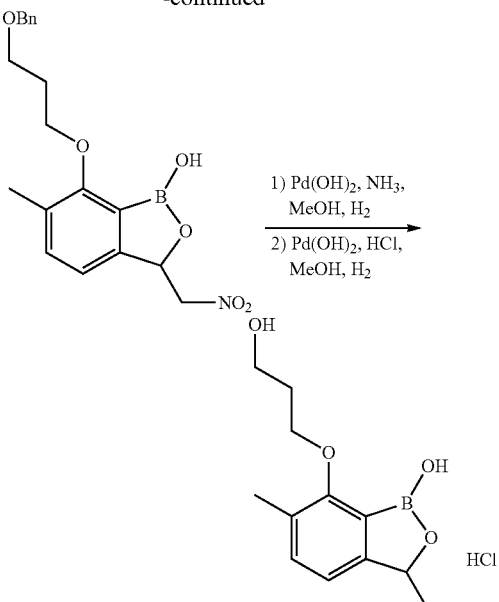

1,2-Dimethoxy-3-methyl-benzene

To a cooled (0° C.) solution of 1,2-dimethoxy-3-methyl-benzene (2.05 g, 13.45 mmol) and TMEDA (2.8 mL, 18.83 mmol) in diethyl ether (100 mL) was added t-butyllithium (1.7 M in pentane, 9.5 mL, 16.14 mmol). The color of the solution changed to light yellow and after a few minutes a white precipitate was observed. The suspension was stirred at room temperature for 18 h, cooled to 0° C. and dimethylformamide (2.08 mL, 26.90 mmol) was added dropwise. The precipitate disappeared and the color of the solution changed to light pink. After stirring for 0.5 h, ice was added followed by 1N HCl (30 mL), the compound was extracted into ethyl acetate, dried (Na$_2$SO$_4$) and the solvent was evaporated to obtain light brown oil. Purification by flash column chromatography (5% EtOAc/hexane) generated the title compound: yield 1.4 g (58%). $^1$H NMR (400 MHz, CDCl$_3$) δ (ppm): 10.34 (s, 1H), 7.49 (d, J=8.2 Hz, 1H), 7.01 (d, J=7.8 Hz, 1H), 4.00 (s, 3H), 3.86 (s, 3H), 2.33 (s, 3H). MS (ESI): m/z=181 (M+1, positive).

2,3-Dihydroxy-4-methyl-benzaldehyde

To a solution of 1,2-dimethoxy-3-methyl-benzene (13.8 g, 76.66 mmol) cooled to −30° C. (dry ice/acetone) in dichloromethane (200 mL) was added boron trichloride (230 mL, 230 mmol) dropwise and the mixture was left to stir overnight at room temperature. The solution was cooled to 0° C. and ice/water was added carefully, and then extracted with excess of dichloromethane. The organic layer was washed with water, dried (Na$_2$SO$_4$) and the solvent was evaporated. Purification by silica gel column chromatography (10-20% EtOAc/hexane) gave the title compound as a crystalline solid: yield 9.2 g (80%). $^1$H NMR (400 MHz, CDCl$_3$) δ (ppm): 11.11 (s, 1H), 9.82 (s, 1H), 7.05 (d, J=8.2 Hz, 1H), 6.81 (d, J=8.6 Hz, 1H), 5.67 (s, 1H), 2.33 (s, 3H).

3-(3-Benzyloxy-propoxy)-2-hydroxy-4-methyl-benzaldehyde

Synthesized according to the methods of general procedure 4 in U.S. Pat. Pub. No. 20090227541 (U.S. patent application Ser. No. 12/142,692) using the following reactants and amounts: 2,3-dihydroxy-4-methyl-benzaldehyde (9 g, 59.21 mmol), (3-bromo-propoxymethyl)-benzene (11.5 mL, 65.13 mmol), sodium tert-butoxide (12.52 g, 130.26 mmol) and DMSO (100 mL). Purification: flash column chromatography (5-10% EtOAc/hexane): yield 15.1 g (85%). $^1$H NMR (400 MHz, CDCl$_3$) δ (ppm): 11.05 (s, 1H), 9.84 (s, 1H), 7.38-7.26 (m, 5H), 7.20 (d, J=7.8 Hz, 1H), 6.80 (d, J=8.2 Hz, 1H), 4.55 (s, 2H), 4.15 (t, J=6.2 Hz, 2H), 3.73 (t, J=6.2 Hz, 2H), 2.31 (s, 3H), 2.19-2.00 (m, 2H).

Trifluoro-methanesulfonic acid 2-(3-benzyloxy-propoxy)-6-formyl-3-methyl-phenyl ester Synthesized according to the methods of general procedure 6 in U.S. Pat. Pub. No. 20090227541 (U.S. patent application Ser. No. 12/142,692) using the following reactants and amounts: 3-(3-Benzyloxy-propoxy)-2-hydroxy-4-methyl-benzaldehyde (0.3 g, 1.0 mmol), trifluoromethanesulfonic acid (0.34 mL, 2.0 mmol), pyridine (0.25 mL, 3.1 mmol), dichloromethane (15 mL). Purification: flash column chromatography (10-15% EtOAc/hexane): yield 0.25 g (59%). $^1$H NMR (400 MHz, CDCl$_3$) δ (ppm): 10.14 (s, 1H), 7.61 (d, J=7.8 Hz, 1H), 7.42-7.29 (m, 6H), 4.53 (s, 2H), 4.07 (t, J=6.4 Hz, 2H), 3.71 (t, J=6.1 Hz, 2H), 2.40 (s, 3H), 2.07-2.22 (m, 2H). $^{19}$F NMR (400 MHz, CDCl$_3$) δ (ppm): −73.63 (s).

3-(3-Benzyloxy-propoxy)-4-methyl-2-(4,4,5,5-tetramethyl-[1,3,2]dioxaborolan-2-yl)-benzaldehyde Synthesized according to the methods of general procedure 5 in U.S. Pat. Pub. No. 20090227541 (U.S. patent application Ser. No. 12/142,692) using the following reactants and amounts: trifluoro-methanesulfonic acid 2-(3-benzyloxy-propoxy)-6-formyl-3-methyl-phenyl ester (0.26 g, 0.6 mmol), bis(pinacolato)diboran (0.31 g, 1.2 mmol), KOAc (0.18 g, 1.8 mmol), PdCl$_2$(dppf) (0.13 g, 0.18 mmol), THF (10 mL). Purification: flash column chromatography (15% EtOAc/hexane): yield 0.091 g (36%). $^1$H NMR (400 MHz, CDCl$_3$) δ (ppm): 9.89 (s, 1H), 7.47 (d, J=7.4 Hz, 1H), 7.40-7.25 (m, 6H), 4.52 (s, 2H), 4.02 (t, J=6.4 Hz, 2H), 3.70 (t, J=6.2 Hz, 2H), 2.32 (s, 3H), 2.20-2.08 (m, 2H), 1.45 (s, 12H).

7-(3-Benzyloxy-propoxy)-6-methyl-3-nitromethyl-3H-benzo[c][1,2]oxaborol-1-ol

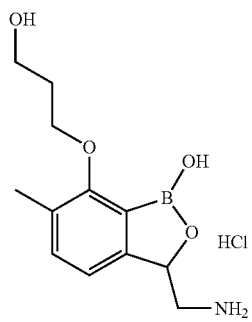

Synthesized according to the methods of general procedure 8 in U.S. Pat. Pub. No. 20090227541 (U.S. patent application Ser. No. 12/142,692) using the following reactants and amounts: 3-(3-benzyloxy-propoxy)-4-methyl-2-(4, 4,5,5-tetramethyl-[1,3,2]dioxaborolan-2-yl)-benzaldehyde (1.14 g, 2.78 mmol), nitromethane (0.45 mL, 8.34 mmol), NaOH (0.78 g, 1.95 mmol), THF (3 mL) and water (9 mL). Purification: flash column chromatography (25% EtOAc/hexanes): yield 0.42 g (41%). $^1$H NMR (400 MHz, DMSO-d$_6$) δ (ppm): 9.41 (s, 1H), 7.37-7.18 (m, 6H), 7.03 (d, J=7.8 Hz, 1H), 5.69 (dd, J=9.2, 2.5 Hz, 1H), 5.28 (dd, J=13.7, 2.7 Hz, 1H), 4.52 (dd, J=13.3, 9.4 Hz, 1H), 4.46 (s, 2H), 4.33 (t, J=6.1 Hz, 2H), 3.58 (t, J=6.1 Hz, 2H), 2.12 (s, 3H), 2.01-1.87 (m, 2H). MS (ESI): m/z=370 (M−1, negative).

3-Aminomethyl-7-(3-hydroxy-propoxy)-6-methyl-3H benzo[c][1,2]oxaborol-1-ol hydrochloride

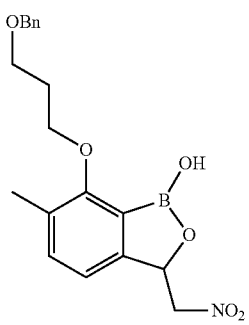 [SMILES: Cc1ccc2c(c1OCCCOCc1ccccc1)B(O)OC2C[N+](=O)[O-]]

To a solution of 7-(3-benzyloxy-propoxy)-6-methyl-3-nitromethyl-3H-benzo[c][1,2]oxaborol-1-ol (0.42 g, 1.13 mmol) in methanolic ammonia (15 mL) was added palladium hydroxide (0.2 g, 45 wt %) in a hydrogenation bottle and the flask was charged with hydrogen at 45 psi for 18 h. The catalyst was filtered off and the solvent was evaporated under reduced pressure. In order to assure all the ammonia has been stripped off, the compound was subjected to the high vacuum for 1 h. The crude (0.38 g) obtained was further dissolved in methanol (15 mL) and transferred to a hydrogenation bottle and concentrated HCl (5-6 drops) was added to make it to pH 2. To this solution palladium hydroxide (0.1 g, 25 wt %) was added and the flask was charged with hydrogen at 45 psi for 1.5 h. The catalyst was filtered off through a pad of Celite and the solvent evaporated. Purification by preparative HPLC provided 0.12 g (39%) of the title compound as a white solid. $^1$H NMR (400 MHz, DMSO-d$_6$) δ (ppm): 8.40 (s, 1H), 7.12 (d, J=7.4 Hz, 1H), 6.80 (d, J=7.4 Hz, 1H), 5.08-4.91 (m, 1H), 4.49-4.21 (m, 2H), 3.64 (t, J=5.7 Hz, 2H), 3.17 (dd, J=12.9, 3.1 Hz, 1H), 2.66 (dd, J=12.7, 8.0 Hz, 1H), 2.14 (s, 3H), 1.81 (quin, J=5.7 Hz, 2H). MS (ESI): m/z=252 (M+1, positive); HPLC purity: 98.25% (MaxPlot 200-400 nm), 98.39% (220 nm).

R. 3-Aminomethyl-6-fluoro-7-(3-hydroxy-propoxy)-3H-benzo[c][1,2]oxaborol-1-ol; hydrochloride salt

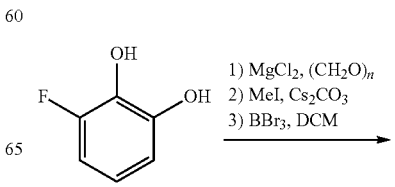

91
-continued

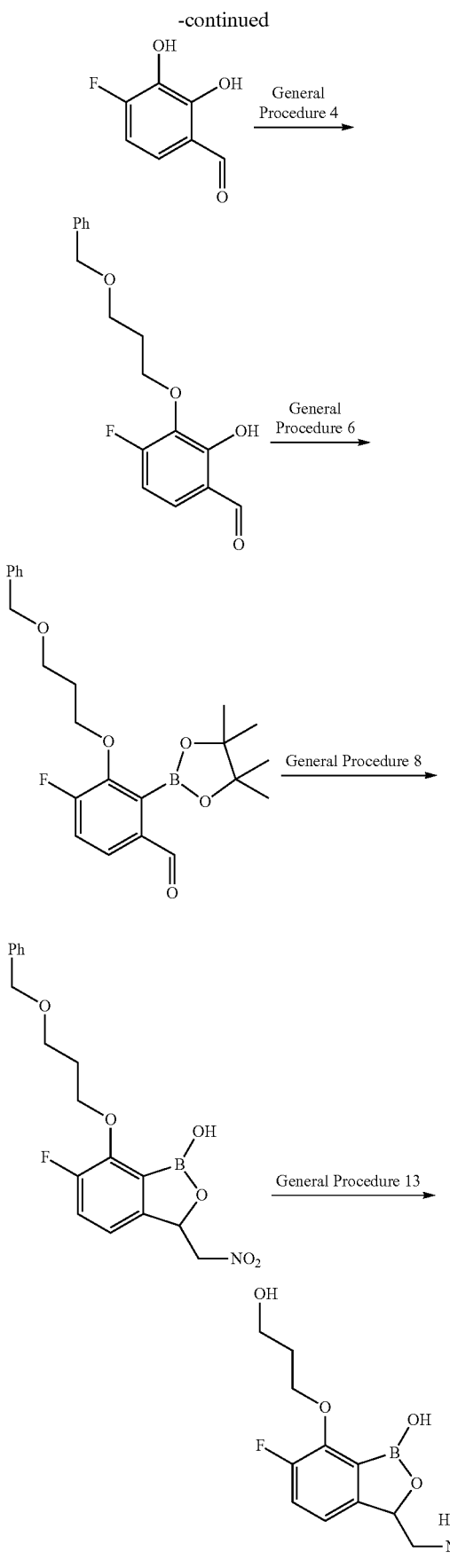

92

4-Fluoro-2,3-dihydroxy-benzaldehyde

To a solution of 3-fluoro-benzene-1,2-diol (20 g, 156 mmol) in anhydrous acetonitrile (400 mL) was added magnesium chloride (37.1 g, 312 mmol), paraformaldehyde (31.6 g) and triethylamine (134 mL, 975 mmol). The reaction mixture was heated at 80° C. for 8 h. The reaction mixture was cooled to room temperature and the solid was collected by filtration. The solid was treated with cold 2 N HCl and the aqueous layer was extracted with EtOAc. The organic layer was concentrated in vacuo yielding 20.4 g of crude. After a second run 40.8 g of crude was dissolved in DMF (1 L), cooled to 0° C., added to $Cs_2CO_3$ (340 g, 1.04 mol) portion-wise. Then methyl iodide (330 mL, 5.28 mol) was added. After warming to room temperature and stirring overnight the solution was filtered, ethyl acetate was added and the organic layer was washed with water (3×). After concentration in vacuo the product was purified by Biotage silica gel chromatography (2% to 3% to 10% to 20% EtOAc/hexanes) resulting in 14.8 g of dimethoxy compound. This material was dissolved in DCM and cooled to −30° C. and $BCl_3$ (1 M in DCM, 134 mL, 0.1343 mol) was added to the solution at −30° C. After overnight at room temperature, the solution was cooled to −70° C. and $BBr_3$ (1 M in DCM, 67.25 mL, 0.067 mol) was added. After overnight warming to room temperature, the solution was cooled in an ice bath and slowly ice water was added. The DCM layer was separated and the aqueous layer was extracted with DCM (2×). The combined organic layer was extracted with brine (2×), dried over $Na_2SO_4$, filtered and concentrated in vacuo. After triturating the residue obtained with hexanes/DCM (6:4) the 5.60 g (11% yield) of the title compound obtained was a brownish pink solid. This material was used in the next step without further purification. $^1$H NMR (400 MHz, DMSO-$d_6$) δ (ppm): 11.36 (s, 1H), 9.83 (s, 1H), 7.16-7.13 (m, 1H), 6.82-6.78 (m, 1H), 5.48 (brs, 1H). $^{19}$F NMR (376 MHz, DMSO-$d_6$ with $D_2O$) δ (ppm): −119.03−−119.08 (m, 1F).

3-(3-Benzyloxy-propoxy)-4-fluoro-2-hydroxy-benzaldehyde

Synthesized according to the methods of general procedure 4 in U.S. Pat. Pub. No. 20090227541 (U.S. patent application Ser. No. 12/142,692) using the following reactants and amounts: 4-fluoro-2,3-dihydroxy-benzaldehyde (5.15 g, 32.9 mmol), NaOtBu (6.95 g, 72.3 mmol), DMSO (200 mL), (3-bromo-propoxymethyl)-benzene (8.31 g, 36.3 mmol). Purification: Biotage silica gel chromatography (hexanes/ethyl acetate gradient) generated 4.00 g of a mixture of the title compound and the dialkylated product. This material was used in the next step without further purification. $^1$H NMR (400 MHz, DMSO-$d_6$) δ (ppm): 10.13 (s, 1H), 7.66-7.54 (m, 5H), 7.53-7.33 (m, 1H), 6.92-6.90 (m, 1H), 4.53 (s, 2H), 4.52-4.44 (m, 2H), 3.71-3.62 (m, 2H), 2.18-2.13 (m, 2H). $^{19}$F NMR (376 MHz, DMSO-d$_6$ with D$_2$O) δ (ppm): −121.03−−121.08 (m, 1F).

3-(3-Benzyloxy-propoxy)-4-fluoro-2-(4,4,5,5-tetramethyl-[1,3,2]dioxaborolan-2-yl)-benzaldehyde Synthesized according to the methods of general procedure 6 in U.S. Pat. Pub. No. 20090227541 (U.S. patent application Ser. No. 12/142,692) using the following reactants and amounts: 3-(3-benzyloxy-propoxy)-4-fluoro-2-hydroxy-benzaldehyde (4.00 g, 13.1 mmol), pyridine (2.34 mL, 28.9 mmol), DCM (100 mL), triflate anhydride (2.21 mL, 13.5 mmol). Purification: Biotage silica gel chromatography (hexanes/ethyl acetate gradient) generated 2.00 g of triflate that was used immediately according to general procedure 5 in U.S. Pat. Pub. No. 20090227541 (U.S. patent application Ser. No. 12/142,692).

Synthesized according to the methods of general procedure 5 in U.S. Pat. Pub. No. 20090227541 (U.S. patent application Ser. No. 12/142,692) using the following reactants and amounts: trifluoro-methanesulfonic acid 2-(3-benzyloxy-propoxy)-3-fluoro-6-formyl-phenyl ester (2.0 g, 4.57 mmol), THF (15 mL), B$_2$pin$_2$ (2.20 g, 8.66 mmol), KOAc (1.60 g, 16.3 mmol), PdCl$_2$(dppf) DCM (0.40 g, 0.55 mmol). Purification: Biotage silica gel chromatography (hexanes/ethyl acetate gradient) generated 0.50 g (26% yield) of the title compound. $^1$H NMR (400 MHz, DMSO-d$_6$) δ (ppm): 9.86 (s, 1H), 7.51 (dd, J=8.2, 4.0 Hz, 1H), 7.34-7.31 (m, 5H), 7.21 (dd, J=11.0, 8.2 Hz, 1H), 4.51 (s, 2H), 4.24 (td, J=6.5, 2.0 Hz, 2H), 3.67 (t, J=6.2 Hz, 2H), 2.11-2.07 (m, 2H); 1.33 (s, 12H); $^{19}$F NMR (376 MHz, DMSO-d$_6$ with D$_2$O) δ (ppm): −120.3−−121.1 (m, 1F).

7-(3-Benzyloxy-propoxy)-6-fluoro-3-nitromethyl-3H-benzo[c][1,2]oxaborol-1-ol

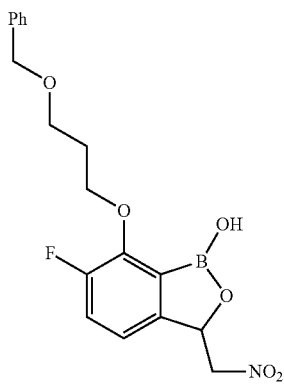 [SMILES: O=[N+]([O-])CC1OB(O)c2c1ccc(F)c2OCCCOCc1ccccc1]

Synthesized according to the methods of general procedure 8 in U.S. Pat. Pub. No. 20090227541 (U.S. patent application Ser. No. 12/142,692) using the following reactants and amounts: 3-(3-benzyloxy-propoxy)-4-fluoro-2-(4,4,5,5-tetramethyl-[1,3,2]dioxaborolan-2-yl)-benzaldehyde (0.40 g, 0.966 mmol), nitromethane (0.15 mL, 2.89 mmol), NaOH (0.038 g, 0.96 mmol), THF (10 mL), water (10 mL). This generated 0.34 g (94% yield) of the title compound. $^1$H NMR (400 MHz, DMSO-d$_6$) δ (ppm): 9.83 (s, 1H), 7.32-7.02 (m, 7H), 5.78-5.75 (m, 1H), 5.28-5.23 (m, 1H), 4.60-4.56 (m, 1H), 4.42 (s, 2H), 4.37 (brs, 2H), 3.57 (brs, 2H), 1.92 (brs, 2H). $^{19}$F NMR (376 MHz, DMSO-d$_6$ with D$_2$O) δ (ppm): −132.3 (1F).

3-Aminomethyl-6-fluoro-7-(3-hydroxy-propoxy)-3H-benzo[c][1,2]oxaborol-1-ol, hydrochloride salt

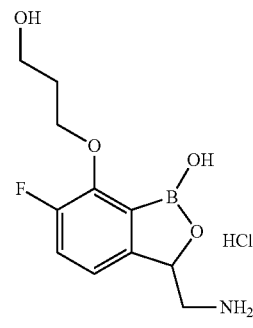 [SMILES: NCC1OB(O)c2c1ccc(F)c2OCCCO ; Cl]

To a mixture of 7-(3-benzyloxy-propoxy)-6-fluoro-3-nitromethyl-3H-benzo[c][1,2]oxaborol-1-ol (0.34 g, 0.906 mmol) and methanolic ammonia (2M, 20 mL) in a Parr apparatus was added Pd(OH)$_2$ on carbon (0.30 g). The apparatus was charged with hydrogen (~40 psi) and was shaken overnight at rt. The suspension was filtered through Celite® with methanol washing and was concentrated in vacuo. The 310 mg of cream colored solid was dissolved in methanol (20 mL), transferred to Parr apparatus and the pH was adjusted to ~3 with a few drops of concentrated HCl. Then Pd(OH)$_2$ on carbon (0.20 g) was added and the apparatus was charged with hydrogen (~40 psi). After 35 minutes, the suspension was filtered through Celite® with methanol washing and was concentrated in vacuo. Purification was accomplished by reverse phase preparative HPLC (acetonitrile/water (0.1% AcOH) gradient) generating 100 mg (43% yield) of the title compound as a white solid. mp 265-267° C.; $^1$H NMR (400 MHz, DMSO-d$_6$ with D$_2$O) δ (ppm): 7.41 (dd, J=11.1, 8.2 Hz, 1H), 7.07 (dd, J=7.9, 2.8 Hz, 1H), 5.29 (d, J=7.0 Hz, 1H), 4.36 (t, J=6.0 Hz, 2H), 3.62 (br.s, 2H), 3.45 (d, J=12.9 Hz, 1H), 2.92-2.86 (m, 1H), 1.93-1.83 (m, 2H); $^{19}$F NMR (376 MHz, DMSO-d$_6$ with D$_2$O) δ (ppm): −135.0 (1F); MS (ESI) m/z=256 (M+1, positive); HPLC purity: 98.57% (MaxPlot 200-400 nm), 97.28% (220 nm).

S. 3-Aminomethyl-7-ethoxy-6-methoxy-3H-benzo[c][1,2]oxaborol-1-ol; hydrochloric acid salt

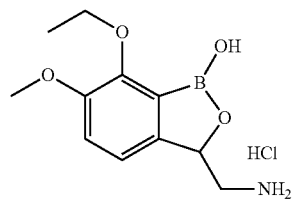

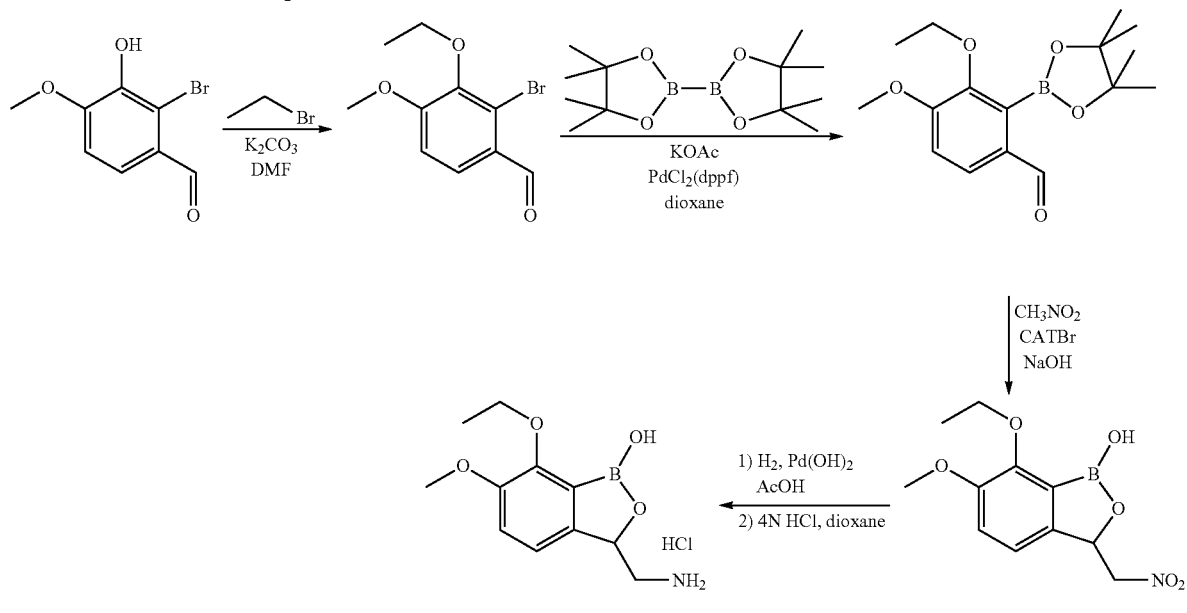

2-Bromo-3-ethoxy-4-methoxy-benzaldehyde

Ethyl bromide (2.88 g, 26.4 mmol) was added to a mixture of 2-bromo-3-hydroxy-4-methoxybenzaldehyde (5.08 g, 22 mmol) and potassium carbonate (4.56 g, 33 mmol) in anhydrous DMF (50 mL) at room temperature under nitrogen. The reaction mixture was stirred at 35° C. for 18 h, diluted with EtOAc (150 mL), washed with water (2×50 mL), brine, dried over $Na_2SO_4$ and concentrated to give crude product as a white solid. Purification by silica column chromatography (eluant: 30% EtOAc in Hexanes) to generate 5.65 g (99% yield) of the title compound as a white solid. $^1$H NMR (400 MHz, $CDCl_3$) δ (ppm) 10.26 (s, 1H), 7.73 (d, J=8.4 Hz, 1H), 6.95 (d, J=8.8 Hz, 1H), 4.08 (q, J=7.1 Hz, 2H), 3.95 (s, 3H), 1.46 (t, J=7.0 Hz, 3H); MS (ESI) m/z=261 (M+1, positive).

[3-Ethoxy-4-methoxy-2-(4,4,5,5-tetramethyl-[1,3,2]dioxaborolan-2-yl)-benzaldehyde Synthesized according to the methods of general procedure 5 in U.S. Pat. Pub. No. 20090227541 (U.S. patent application Ser. No. 12/142,692) using the following reactants and amounts: 2-bromo-3-ethoxy-4-methoxy-benzaldehyde (4 g, 15.43 mmol), KOAc (4.55 g, 46.29 mmol), bis(pinacolato)diboron (7.84 g, 30.86 mmol). $PdCl_2$(dppf) (0.91 g, 1.24 mmol) in dry dioxane (90 mL). The crude product was purified by silica gel column chromatography (eluant:EtOAc/hexanes 1:9 then 1:3) to afford the title compound as a white solid (1.50 g, 32% yield). $^1$H NMR (400 MHz, $CDCl_3$) δ (ppm) 9.71 (s, 1H), 7.44 (d, J=8.4 Hz, 1H), 6.89 (d, J=8.4 Hz, 1H), 4.01 (q, J=7.1 Hz, 2H), 3.82 (s, 3H), 1.38 (s, 12H), 1.35 (t, J=7.0 Hz, 3H).

7-Ethoxy-6-methoxy-3-nitromethyl-3H-benzo[c][1,2]oxaborol-1-ol

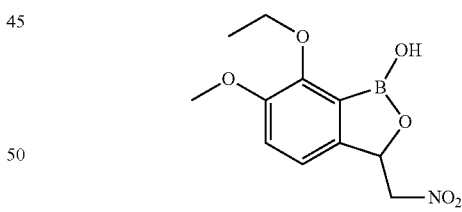

Synthesized according to the methods of general procedure 9 in U.S. Pat. Pub. No. 20090227541 (U.S. patent application Ser. No. 12/142,692) using the following reactants and amounts: [3-ethoxy-4-methoxy-2-(4,4,5,5-tetramethyl-[1,3,2]dioxaborolan-2-yl)-benzaldehyde (1.47 g, 4.80 mmol), nitromethane (0.92 g, 14.4 mmol), CATBr (88 mg, 0.24 mmol) in dry THF (20 mL) and NaOH (0.025 M aqueous solution). Purification by silica gel column chromatography (eluant: 10% EtOAc/hexane to 30% EtOAc/hexane) to obtain the title compound as a yellow solid (0.75 g, 59%). $^1$H NMR {400 MHz, DMSO-$d_6$+$D_2O$ (0.01 ml)} δ (ppm) 9.34 (s, 1H), 7.18 (d, J=8.1 Hz, 1H), 7.11 (d, J=8.0 Hz, 1H), 5.68 (dd, J=9.2, 2.0 Hz, 1H), 5.29 (dd, J=13.2, 2.8

Hz, 1H), 4.55-4.50 (m, 1H), 4.20 (q, J=7.0 Hz, 2H), 3.77 (s, 3H), 1.27 (t, J=7.0 Hz, 3H); MS (ESI) m/z=261 (M−1, negative).

3-Aminomethyl-7-ethoxy-6-methoxy-3H-benzo[c][1,2]oxaborol-1-ol; hydrochloride salt

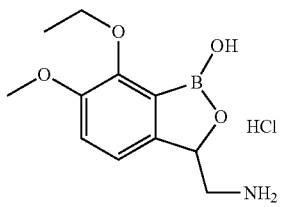 [SMILES: CCOc1c(OC)ccc2c1B(O)OC2CN ; Cl]

Synthesized according to the methods of general procedure 13 in U.S. Pat. Pub. No. 20090227541 (U.S. patent application Ser. No. 12/142,692) using the following reactants and amounts: 7-Ethoxy-6-methoxy-3-nitromethyl-3H-benzo[c][1,2]oxaborol-1-ol (0.97 g, 3.63 mmol), glacial acetic acid (20 mL), Pd(OH)$_2$ on carbon (20% metal content, 50% weight-wet) (300 mg). Purification: preparative HPLC (C18 column, using acetonitrile and 0.1% AcOH/water solution) provided the title compound (0.28 g; 28% yield). m.p. 202-204° C. $^1$H NMR {400 MHz, CD$_3$OD} δ (ppm) 7.20 (d, J=8.0 Hz, 1H), 7.08 (d, J=8.1 Hz, 1H), 5.40 (dd, J=8.4, 2.8 Hz, 1H), 4.23 (q, J=7.1 Hz, 2H), 3.31 (s, 3H), 3.56 (dd, J=13.6, 7.2 Hz, 1H), 2.92 (dd, J=13.2, 7.2 Hz 1H), 1.33 (t, J=7 Hz, 3H); MS (ESI) m/z=238 (M+1, positive); HPLC purity: 98.79% (MaxPlot 200-400 nm) and 99.13% (220 nm).

T. 3-Aminomethyl-7-ethoxy-6-fluoro-3H-benzo[c][1,2]oxaborol-1-ol; hydrochloride salt

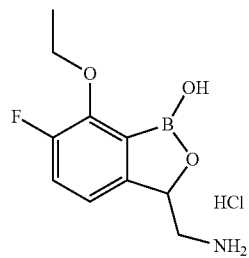

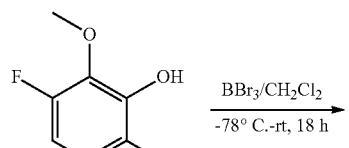

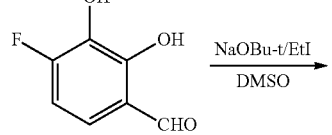

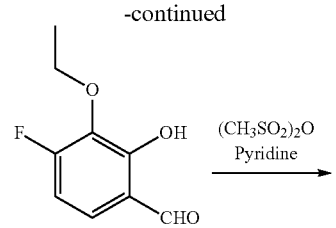

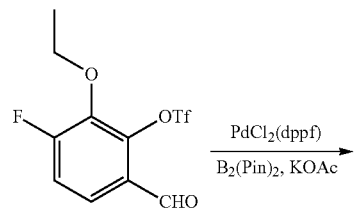

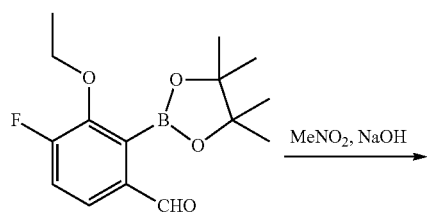

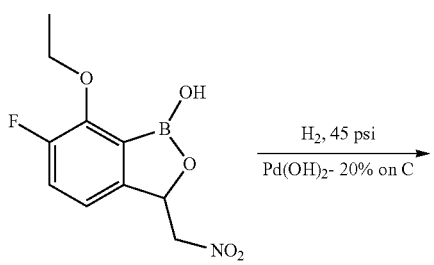

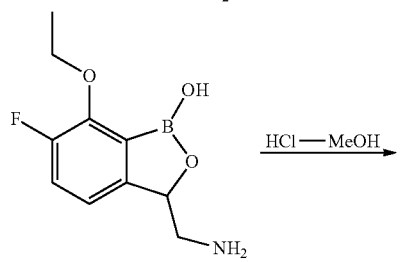

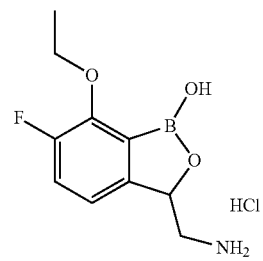

4-Fluoro-2,3-dihydroxybenzaldehyde

To a solution at −78° C. of 2,3-dimethoxy-4-fluorobenzaldehyde (7.0 g, 38.0 mmol) in dry dichloromethane (150 mL) was added dropwise BBr$_3$ (23.8 g, 95.0 mmol) in dichloromethane (30 mL). Reaction mixture was allowed to attain room temperature and stirred for 18 h. Then reaction mixture was cooled to −78° C., and quenched with a mixture of methanol (10 mL) and water (50 mL) and stirred at room temperature for 30 min. Precipitated solid was separated by filtration and washed with cold dichloromethane. Dichloromethane layer was concentrated to yield the title compound as a solid (5.2 g, 88%). $^1$H NMR (400 MHz, CHLOROFORM-d) δ ppm: 11.38 (s, 1H), 9.84 (s, 1H), 7.15 (dd, J=8.6, 5.5 Hz, 1H), 6.81 (t, J=9.4 Hz, 1H), 5.47 (s, 1H); MS (ESI) m/z=155 (M−1, negative).

3-Ethoxy-4-fluoro-2-hydroxybezaldehyde

To a solution of 2,3-dihydroxy-4-fluorobenzaldehyde (3.0 g, 19.23 mmol) in DMSO (100 mL), NaOBu-t (3.692 g, 38.46 mmol) was added in portions at room temperature and stirred for 15 min. Then iodoethane was added dropwise at room temperature and stirred for 18 h. The reaction mixture was poured onto crushed ice (200 mL) and acidified with 2.5 M HCl to pH 3.0. The product was extracted with ethyl acetate (2×100 mL), concentrated and the product was chromatographed on a column of silica gel (Hex:EtOAc=95:5) to give the title compound as a crystalline solid (2.3 g, 65%). $^1$H NMR (400 MHz, CHLOROFORM-d) δ ppm: 11.36 (s, 1H), 9.83 (s, 1H), 7.39-7.19 (m, 1H), 6.77 (t, J=9.2 Hz, 1H), 4.22 (q, J=7.0 Hz, 2H), 1.40 (t, J=7.0 Hz, 3H); MS (ESI) m/z=183 (M+1, positive).

Trifluoromethanesulfonic acid 2-ethoxy-3-fluoro-6-formyl-phenyl ester

To a mixture of 3-ethoxy-4-fluoro-2-hydroxybezaldehyde (2.208 g, 12.0 mmol) and pyridine (1.986 g, 24.0 mmol) in dichloromethane (30.0 mL) at 0° C. was added dropwise trifluoromethanesulfonic anhydride (4.060, 14.4 mmol) in dichloromehane (5.0 mL). The reaction mixture was stirred at 0° C. for 2 h and room temperature for 3 h. Then diluted with dichloromethane (40 mL), washed with 2M HCl, brine and dried over anhydrous sodium sulfate. The solvent was removed under reduced pressure to give the title compound as a light yellow liquid (3.3 g, 87%). $^1$H NMR (400 MHz, CHLOROFORM-d) δ ppm: 10.15 (s, 1H), 7.66 (dd, J=8.6, 5.5 Hz, 1H), 7.28-7.22 (m, 1H), 4.36 (q, J=6.9 Hz, 2H), 1.47 (t, J=7.0 Hz, 3H).

3-Ethoxy-4-fluoro-2-(4,4,5,5-tetramethyl-[1,3,2]dioxaborolan-2-yl)-benzaldehyde

To a solution of trifluoromethanesulfonic acid 2-ethoxy-3-fluoro-6-formyl-phenyl ester (2.2 g, 6.96 mmol) in dry THF (35.0 mL) bis(pinacolato)diboron (2.134 g, 8.4 mmol), PdCl$_2$(dppf) (367 mg, 0.5 mmol) and potassium acetate (1.372 g, 14.0 mmol) were added and purged with nitrogen for 15 min. The reaction mixture was heated under reflux for 24 h. Cooled to room temperature and diluted with ethyl acetate (40 mL) and filtered through Celite. The solvent was removed under reduced pressure and the residue was chromatographed on a column of silica gel (Hex:EtOAc=9:1) to give the title compound as an off-white solid (850.0 mg, 42%). $^1$H NMR (400 MHz, CHLOROFORM-d) δ ppm: 9.87 (s, 1H), 7.51 (dd, J=8.2, 4.3 Hz, 1H), 7.22 (dd, J=10.9, 8.6 Hz, 1H), 4.20 (q, J=7.0 Hz, 2H), 1.46 (s, 12H), 1.40 (t, J=7.0 Hz, 3H); MS (ESI) m/z=295 (M+1, positive).

7-Ethoxy-6-fluoro-3-nitromethyl-3H-benzo[c][1,2]oxaborol-1-ol

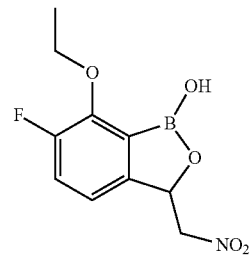 [SMILES: CCOc1c(F)ccc2c1B(O)OC2C[N+](=O)[O-]]

To a cooled solution of sodium hydroxide (80 mg, 2.0 mmol) in water (3.0 mL), nitromethane (244.0 mg, 4.0 mmol) was added at 0° C. and stirred for 10 min. Then 3-ethoxy-4-fluoro-2-(4,4,5,5-tetramethyl-[1,3,2]dioxaborolan-2-yl)-benzaldehyde (588.0 mg, 2.0 mmol) in THF (5.0 mL) was added. The reaction mixture was stirred at for 1 h at 0° C. and for 2 h at room temperature. The reaction mixture was acidified with 2.5 M HCl (1.0 mL) and the product was extracted with ethyl acetate (2×20 mL). The organic extracts were combined and washed with brine and dried over anhydrous sodium sulfate. The solvent was removed under reduced pressure and product was chromatographed on a column of silica gel (CH$_2$Cl$_2$:MeOH=95:5) to give the title compound as a solid (350 mg, 69%). $^1$H NMR (400 MHz, DMSO-d$_6$) δ ppm: 7.40 (dd, J=11.3, 8.2 Hz, 1H), 7.16 (dd, J=8.0, 3.3 Hz, 1H), 5.74 (d, J=9.0 Hz, 1H), 5.30 (dd, J=13.5, 2.2 Hz, 1H), 4.62 (dd, J=13.5, 9.2 Hz, 1H), 4.35 (q, J=6.8 Hz, 2H), 1.28 (t, J=6.8 Hz, 3H); MS (ESI) m/z=254 (M−1, negative).

3-Aminomethyl-7-ethoxy-6-fluoro-3H-benzo[c][1,2]oxaborol-1-ol; hydrochloride salt

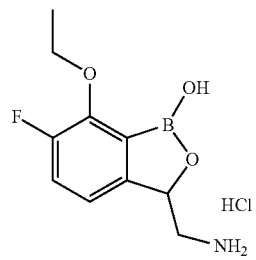 [SMILES: CCOc1c(F)ccc2c1B(O)OC2CN ; Cl]

To a solution of 7-ethoxy-6-fluoro-3-nitromethyl-3H-benzo[c][1,2]oxaborol-1-ol (320.0 mg, 1.25 mmol) in methanol (5.0 mL), 5.0 mL of 2M ammonia in methanol and 160 mg of Pd(OH)$_2$ on C were added and hydrogenated at 45 PSI for 18 h. Catalyst was removed by filtration and the filtrate was concentrated to generating an off-white solid (250 mg). This solid was dissolved in methanol (3 mL) and 3.0 mL of 1.2 M HCl in methanol was added and stirred at room temperature for 3 h. Excess HCl and solvent were removed under reduced pressure and the product was triturated with ether to give the title compound as an off-white solid (140 mg, 43%). $^1$H NMR (400 MHz, DMSO-d$_6$) δ ppm: 9.43 (s, 1H), 8.13 (br. s., 3H), 7.40 (dd, J=11.5, 8.0 Hz, 1H), 7.16 (dd, J=7.8, 3.1 Hz, 1H), 5.32 (d, J=6.3 Hz, 1H), 4.35 (q, J=7.0 Hz, 2H), 3.43 (br. s., 1H), 2.92 (br. s., 1H), 1.29 (t, J=7.0 Hz, 3H); ¹⁹F NMR (376 MHz, DMSO-d₆) δ ppm −135 (s, 1F); MS (ESI) m/z=226 (M+1, positive); HPLC purity: 95.81% (MaxPlot 200-400 nm), 94.73% (220 nm).

U. 3-(Aminomethyl)-5-chloro-7-ethoxybenzo[c][1,2]oxaborol-1(3H)-ol

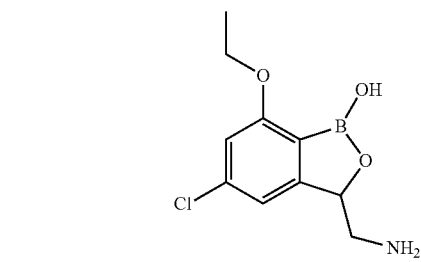

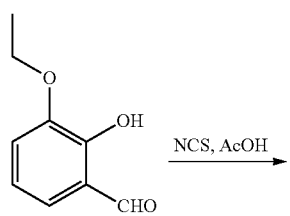

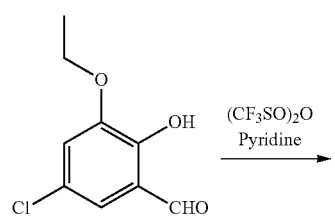

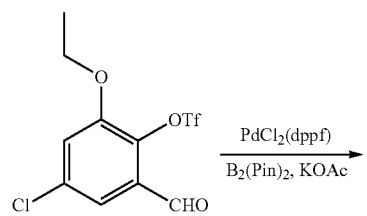

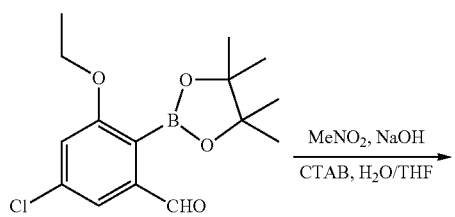

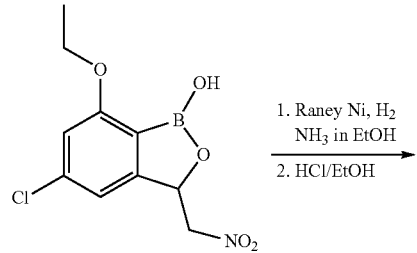

-continued

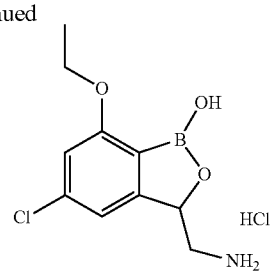

4-Chloro-2-ethoxy-6-formylphenyl trifluoromethanesulfonate

To a solution of 3-ethoxy-2-hydroxybenzaldehyde (20 g, 120.4 mmol) in AcOH (200 mL) was added N-chlorosuccinimide (16.1 g, 120.4 mmol). The reaction mixture was heated up to 105° C. for 30 min. After cooled down to room temperature, the mixture was stirred for additional 2.5 h. Subsequently, 200 mL of water was added slowly over 10 min. The mixture was filtered and dried to give a yellow solid, which was recrystallized in ethanol to give 4 g of the target compound (4 g, 17% yield).

4-Chloro-2-ethoxy-6-formylphenyl trifluoromethanesulfonate

To a solution of 5-chloro-3-ethoxy-2-hydroxybenzaldehyde (2.0 g, 10.0 mmol) in pyridine (2 mL) and DCM (20 mL) at 0° C. was dropwise added trifluoromethanesulfonic anhydride (1 mL). The reaction was stirred for 1 h at 0° C. before quenched with ice-water. The organic layer was washed with sat. aqueous NaHCO₃ (20 mL) and brine (20 mL), dried over anhydrous Na₂SO₄ and then concentrated in vacuo. The residue was purified by column chromatography on silica gel to give target compound (2.0 g, yield: 60%).

5-Chloro-3-ethoxy-2-(4,4,5,5-tetramethyl-1,3,2-dioxaborolan-2-yl)benzaldehyde A mixture of 4-chloro-2-ethoxy-6-formylphenyl trifluoromethanesulfonate (330 mg, 1 mmol), KOAc (350 mg, 2.0 mmol), bis(pinacolato)diborane (600 mg, 2.0 mmol) and PdCl₂(dppf)CH₂Cl₂ (65 mg, 0.08 mmol, 8 mol %) in dioxane (30 mL) was degassed for 15 min with N₂ and stirred at 100° C. for 3 h. After quenched with ice-water, the reaction mixture was extracted with EtOAc (3×30 mL). The combined organic layers were washed with sat. aqueous NaHCO₃ (20 mL) and brine (20 mL), dried over anhydrous Na₂SO₄ and then concentrated. The residue was purified by column chromatography on silica gel to give the compound (150 mg, yield: 43%).

5-Chloro-7-ethoxy-3-(nitromethyl)benzo[c][1,2]oxaborol-1(3H)-ol

The mixture of 5-chloro-3-ethoxy-2-(4,4,5,5-tetramethyl-1,3,2-dioxaborolan-2-yl)benzaldehyde (310 mg, 1 mmol), NaOH (40 mg, 1 mmol) and CTAB (5 mg, 0.05 mmol) in H₂O (2 mL) and THF (10 mL) was stirred for 0.5 h at room temperature. After dropwise addition of nitromethane (0.2 mL, 2 mmol), the reaction mixture was stirred at room temperature for 3 h. Then the cyclization was afforded by adding the diluted aqueous HCl solution (2 N) to pH=2 and then extracted with EtOAc (3×30 mL). The combined organic layers were washed with brine (25 mL), dried over anhydrous Na$_2$SO$_4$ and concentrated to dryness. The residue was purified by prep-HPLC to give the compound (100 mg, yield: 56%). $^1$H NMR (400 MHz, DMSO-d$_6$) δ 9.20 (s, 1H), 7.22 (s, 1H), 6.96 (s, 1H), 5.69-5.72 (m, 1H), 5.30-5.34 (m, 1H), 4.61-4.67 (m, 1H), 4.10-4.15 (m, 2H), 1.31-1.34 (m, 3H);

3-(Aminomethyl)-5-chloro-7-ethoxybenzo[c][1,2]oxaborol-1(3H)-ol

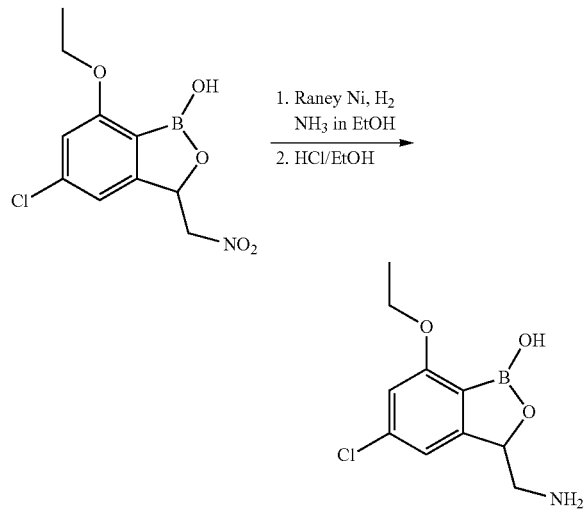

A mixture of 5-chloro-7-ethoxy-3-(nitromethyl)benzo[c][1,2]oxaborol-1(3H)-ol (270 mg, 1.0 mmol), Raney-Ni (~125 mg) and 2 M NH$_3$ in EtOH (2 mL) in EtOH (10 mL) was shaken under an atmosphere of H$_2$ for 2 h at room temperature. The mixture was filtered through a bed of Celite and the filtrate was concentrated in vacuo. The crude amine was dissolved in EtOAc (2 mL) and HCl solution in Et$_2$O (20 mL) was added immediately. After 1 h, the suspension was filtered and the resulting solid was washed with hexanes to give compound the target compound (100 mg, yield: 43%). $^1$HNMR (400 MHz, DMSO-d$_6$) δ 9.06 (s, 1H), 8.18 (s, 3H), 7.22 (s, 1H), 6.96 (s, 1H), 5.27-5.29 (m, 1H), 4.10-4.13 (m, 2H), 3.40-3.47 (m, 1H), 2.87-2.92 (m, 1H), 1.30-1.36 (m, 3H); MS (ESI) m/z=242 [M+H]$^+$.

V. (S)-3-(aminomethyl)-4-bromo-7-ethoxybenzo[c][1,2]oxaborol-1(3H)-ol hydrochloride Step 1: tert-butyl (7-ethoxy-1-hydroxy-1,3-dihydrobenzo[c][1,2]oxaborol-3-yl)methyl-carbamate

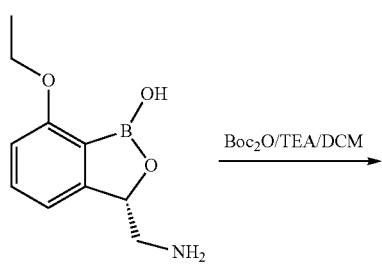

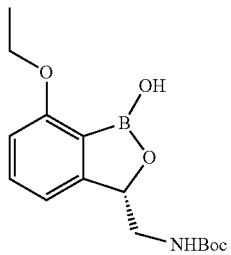

To the mixture of 3-(aminomethyl)-7-ethoxybenzo[c][1,2]oxaborol-1 (3H)-ol hydrochloride salt (5.0 g, 20.5 mmol) and triethylamine (10.4 g, 103.0 mmol) in dichloromethane (250 mL) at 0° C. was added di-tert-butyl dicarbonate (6.7 g, 30.8 mmol). The mixture was stirred for 4 h at room temperature. After the reaction was quenched with sat. NaHCO$_3$ (500 mL), the resulting mixture was extracted with EtOAc (3×300 mL), and the combined organic layers were dried over anhydrous Na$_2$SO$_4$ and concentrated in vacum. The residue was purified by flash-column chromatography (2.5% to 5.0% MeOH in DCM) to give the product (5.51 g, yield 87%).

Step 2: tert-butyl (4-bromo-7-ethoxy-1-hydroxy-1,3-dihydrobenzo[c][1,2]oxaborol-3-yl)-methylcarbamate

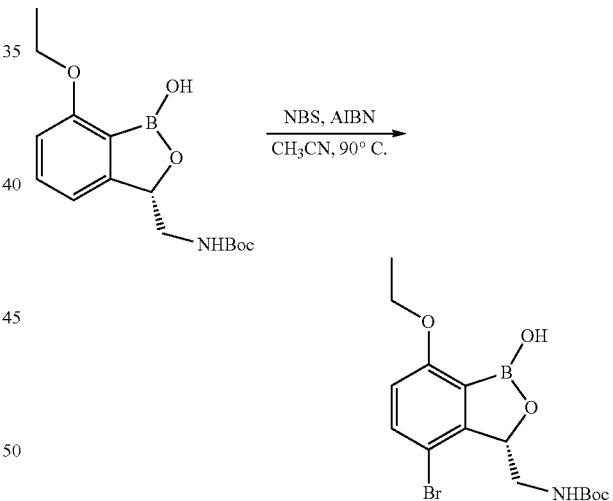

To the solution of tert-butyl (7-ethoxy-1-hydroxy-1,3-dihydrobenzo[c][1,2]oxaborol-3-yl)methyl-carbamate (5.5 g, 17.9 mmol) and 1-bromopyrrolidine-2,5-dione (3.8 g, 21.5 mmol) in CH$_3$CN (1100 mL) was added 2,2'-Azobis(2-methylpropionitrile (220 mg). The mixture was stirred for 1 h at 90° C. The reaction mixture was then concentrated in high vacum and the residue was purified by column chromatography (2.5% to 5.0% MeOH in DCM) to give the product (3.7 g, yield 54%). $^1$H NMR (300 MHz, DMSO-d$_6$) 8.90 (s, 1H), 7.55-7.53 (d, 1H), 6.85-6.82 (d, 1H), 5.08-5.07 (d, 1H), 4.11-4.07 (m, 2H), 3.82-3.79 (bd, 1H), 3.06-3.03 (m, 1H), 1.39 (s, 9H), 1.30 (t, 3H); MS (ESI) m/z=387 [M+H]$^+$.

105

Step 3: (S)-3-(aminomethyl)-4-bromo-7-ethoxy-benzo[c][1,2]oxaborol-1(3H)-ol hydrochloride

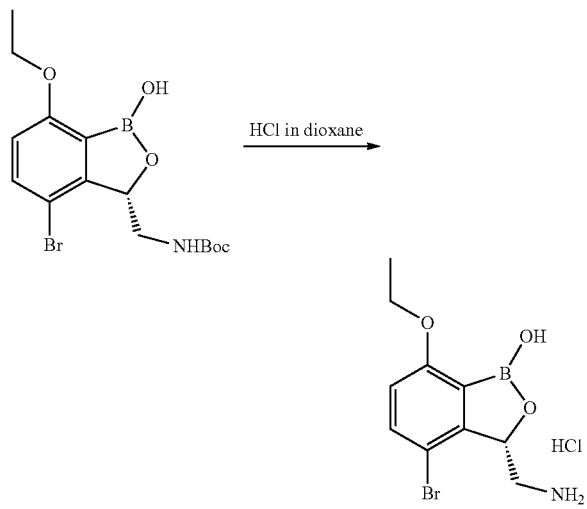

The mixture of tert-butyl (4-bromo-7-ethoxy-1-hydroxy-1,3-dihydrobenzo[c][1,2]oxaborol-3-yl)-methylcarbamate (3.7 g, 9.6 mmol) in 4N HCl in dioxane (12 ml, 48.0 mmol) was stirred at room temperature for 2 h and then concentrated to dryness (water bath <30° C.). The residue was triturated with DCM/ether (1/10, 2×10 mL) and the white solid was dried in high vacuum to give the product (2.96 g, yield: 92%). $^1$H NMR (300 MHz, DMSO-$d_6$) 9.11 (s, 1H), 8.1 (bs, 3H), 7.63-7.60 (d, 1H), 6.92-6.89 (d, 1H), 5.27-5.24 (m, 1H), 4.12-4.05 (m, 2H), 3.62-3.57 (m, 1H), 2.99-2.92 (m, 1H), 1.34-1.30 (t, 3H); MS (ESI) m/z=287 [M+H]$^+$.

Example 2

LeuRS IC$_{50}$ Testing

Experiments were performed in 96-well microtiter plates, using 80 µL reaction mixtures containing 50 mM HEPES-KOH (pH 8.0), 30 mM MgCl$_2$ and 30 mM KCl, 13 µM [$^{14}$C]leucine (306 mCi/mmol, Perkin-Elmer), 15 uM total E. coli tRNA (Roche, Switzerland), 0.02% (w/v) BSA, 1 mM DTT, 0.2 pM LeuRS and 4 mM ATP at 30° C. Reactions were started by the addition of 4 mM ATP. After 7 minutes, reactions were quenched and tRNA was precipitated by the addition of 50 µL of 10% (w/v) TCA and transferred to 96-well nitrocellulose membrane filter plates (Millipore Multiscreen HTS, MSHAN4B50). Each well was then washed three times with 100 µL of 5% TCA. Filter plates were then dried under a heat lamp and the precipitated [$^{14}$C]leucine tRNA$^{Leu}$ was quantified by liquid scintillation counting using a Wallac MicroBeta Trilux model 1450 liquid scintillation counter (PerkinElmer, Waltham Mass.).

To determine the inhibitor concentration which reduces enzyme activity by 50% (IC$_{50}$), increasing concentrations of inhibitor were incubated with LeuRS enzyme, tRNA and leucine for 20 minutes. Reactions were initiated by the addition of 4 mM ATP and stopped after 7 minutes then precipitated and counted to quantify radioactivity.

Biochemical testing results for exemplary compounds of the invention are provided in FIG. 1.

106

Example 3

Antibacterial MIC Testing

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria That Grow Aerobically; Approved Standard—Seventh Edition) (M07-A7) and anaerobic bacteria (Methods for Antimicrobial Susceptibility Testing of Anaerobic Bacteria; Approved Standard—Seventh Edition) (M11-A7).

Antibacterial MIC testing results for exemplary compounds of the invention are provided in FIG. 1.

Example 4

Microplate Alamar Blue Assay (MABA)

The microplate alamar blue assay (MABA) was essentially performed as described by Collins, L., et al., Antimicrob Agents Chemother 41: 1004-1009 (1997). For example, black, clear-bottomed 96-well microplates (black view plates; Packard Instrument Company, Meriden, Conn.) with the outer perimeter wells filled with sterile water to prevent dehydration in experimental wells. Initial drug dilutions were prepared in dimethyl sulfoxide and subsequent two fold dilutions were performed in 0.1 ml of 7H9GC (no Tween 80) in the microplates. Frozen inocula were initially diluted 1:20 in BACTEC 12B medium followed by a 1:50 dilution in 7H9GC. Addition of 100 µL to wells resulted in final bacterial titers of between 2.0×10$^5$ and 5×10$^4$ CFU/mL for H37Rv and H37Ra, respectively. Wells containing drug only were used to detect autofluorescence of compounds plus additional control wells consisted of bacteria only (B) and medium only (M). Plates were incubated at 37° C. Starting at day 4 of incubation, 20 µL of 10× alamar Blue solution (Alamar Biosciences/Accumed, Westlake, Ohio) and 12.5 µL of 20% Tween 80 were added to one B well and one M well, and plates were reincubated at 37° C. Wells were observed at 12 and 24 h for a color change from blue to pink and for a reading of greater than or equal to 50,000 fluorescence units (FU). Fluorescence was measured in a Cytofluor II microplate fluorometer (PerSeptive Biosystems, Framingham, Mass.) in bottom-reading mode with excitation at 530 nm and emission at 590 nm. If the B wells became pink by 24 h, reagent was added to the entire plate. If the well remained blue or 50,000 FU was measured, additional M and B wells were tested daily until a color change occurred, at which time reagents were added to all remaining wells. Plates were then incubated at 37° C., and results were recorded at 24 h post-reagent addition. Visual MICs were defined as the lowest concentration of drug that prevented a color change. For fluorometric MICs, a background subtraction was performed on all wells with a mean of triplicate M wells. Percent inhibition was defined as 1−(test well FU/mean FU of triplicate B wells)×100. The lowest drug concentration effecting an inhibition of 90% was considered the MIC.

Biochemical testing results for exemplary compounds of the invention are provided in FIG. 1.

Example 5

Low Oxygen Recovery Assay (LORA)

The low-oxygen recovery assay (LORA) was essentially performed as described by Cho et al. Antimicrob Agents

*Chemother* 51: 1380-1385 (2007). A recombinant *M. tuberculosis* $H_{37}R_v$ bearing luxAB on a plasmid, pFCA-luxAB, was used in all the LORA experiments. Frozen aliquots from a low oxygen adapted culture were thawed, diluted in Middlebrook 7H12 broth (Middlebrook 7H9 broth containing 1 mg/mL Casitone, 5.6 g/mL palmitic acid, 5 mg/mL bovine serum albumin, and 4 g/ml filter-sterilized catalase), and sonicated for 15 s. The cultures were diluted to obtain an $A_{570}$ of 0.03 to 0.05 and 3,000 to 7,000 RLUs per 100 μL. This corresponds to $5 \times 10^5$ to $2 \times 10^6$ CFU/mL. Twofold serial dilutions were prepared in a volume 100 μL in black 96-well microtiter plates, and 100 μL of the cell suspension was added. For LORA, the microplate cultures were placed under anaerobic conditions (oxygen concentration, less than 0.16%) by using an Anoxomat model WS-8080 (MART Microbiology) and three cycles of evacuation and filling with a mixture of 10% $H_2$, 5% $CO_2$, and 85% $N_2$. An anaerobic indicator strip was placed inside the chamber to visually confirm the removal of oxygen. The plates were incubated at 37° C. for 10 days and then transferred to an ambient gaseous condition (5% $CO_2$-enriched air) incubator for a 28-h "recovery." On day 11 (after the 28-h aerobic recovery), 100 μL culture was transferred to white 96-well microtiter plates for determination of luminescence. A 10% solution of n-decanal aldehyde (Sigma) in ethanol was freshly diluted 10-fold in PBS, and 100 μl was added to each well with an autoinjector. Luminescence was measured in a Victor2 multilabel reader (Perkin-Elmer Life Sciences) by using a reading time of 1 s. The MIC was defined as the lowest drug concentration effecting growth inhibition of 90% relative to the growth for the drug-free controls.

Biochemical testing results for exemplary compounds of the invention are provided in FIG. 1.

Example 6

*Tuberculosis* In Vivo Efficacy Experiments

The TB in vivo efficacy experiments were essentially performed as described in Lenaerts et al. *Antimicrob Agents Chemother* 47: 783-785 (2003) with a few modifications. A highly susceptible gamma interferon specific pathogen-free C57BL/6-Ifngtmlts (GKO) mice (Jackson Laboratories, Bar Harbor, Me.) were exposed to a low-dose aerosol infection with *M. tuberculosis* strain Erdman in a Glas-Col inhalation exposure system as previously described in Kelly et al. *Antimicrob Agents Chemother* 40: 2809-2812 (1996). Every treatment group consisted of five mice for every following time point. Treatment was started 10 days after infection. One control group of infected mice was sacrificed at the start of treatment. A second group of infected but untreated mice was sacrificed after the cessation of treatment at 24 days. C and L were formulated in saline and E was formulated in 50% water/35% PEG400/5% PG, while rifampicin was formulated in 20% cyclodextrin. All compounds were administered by oral gavage. Rifampicin was dosed at 10 mg/kg QD PO. C was dosed at 100 mg/kg BID PO. E was dosed at 100 mg/kg BID PO. L was dosed at 100 mg/kg QD PO. After completion of therapy, the mice were sacrificed by carbon dioxide inhalation. Lungs were aseptically removed and disrupted in a tissue homogenizer. The number of viable organisms was determined by serial dilution of the homogenates on nutrient Middlebrook 7H11 agar plates (GIBCO BRL, Gaithersburg, Md.). The plates were incubated at 37° C. in ambient air for 4 weeks prior to the counting of viable *M. tuberculosis* colonies (CFU).

On day 3, the control group had a mean log 10 CFU/lung of 2.83 (0.40). On day 10, the control group had a log 10 CFU/lung of 4.81 (0.08). On day 24, the control group had a log 10 CFU/lung of 8.96 (0.14). On day 24, the group treated with rifampicin had a log 10 CFU/lung of 6.16 (0.10). On day 24, the group treated with C had a log 10 CFU/lung of 5.06 (0.26). On day 24, the group treated with E had a log 10 CFU/lung of 2.73 (0.05). On day 24, the group treated with L had a log 10 CFU/lung of 3.08 (0.06).

Example 7

*Tuberculosis* In Vivo Efficacy Experiments

The TB in vivo efficacy experiments were essentially performed as described in Lenaerts et al. *Antimicrob Agents Chemother* 47: 783-785 (2003) with a few modifications. A highly susceptible gamma interferon specific pathogen-free C57BL/6-Ifngtmlts (GKO) mice (Jackson Laboratories, Bar Harbor, Me.) were exposed to a low-dose aerosol infection with *M. tuberculosis* strain Erdman in a Glas-Col inhalation exposure system as previously described in Kelly et al. *Antimicrob Agents Chemother* 40: 2809-2812 (1996). Every treatment group consisted of five mice for every following time point. Treatment was started 13 days after infection. One control group of infected mice was sacrificed at the start of treatment. A second group of infected but untreated mice was sacrificed after the cessation of treatment at 22 days. N was formulated in saline and E was formulated in 50% water/35% PEG400/5% PG, while Isoniazid (INH) was formulated in distilled water. All compounds were administered by oral gavage. INH was dosed at 25 mg/kg QD PO. E was dosed at 100 mg/kg QD PO. N was dosed at 100 mg/kg BID PO. After completion of therapy, the mice were sacrificed by carbon dioxide inhalation. Spleens and lungs were aseptically removed and disrupted in a tissue homogenizer. The number of viable organisms was determined by serial dilution of the homogenates on nutrient Middlebrook 7H11 agar plates (GIBCO BRL, Gaithersburg, Md.). The plates were incubated at 37° C. in ambient air for 4 weeks prior to the counting of viable *M. tuberculosis* colonies (CFU).

On day 13, the control group had a mean log 10 CFU of 7.02 (0.08) for lungs and mean log 10 CFU for spleens of 3.99 (0.21). On day 22, the control group had a log 10 CFU for lungs of 7.82 (0.11) and spleens of 6.69 (0.08). On day 22, the group treated with INH had a log 10 CFU for lungs of 5.29 (0.13) and for spleens of 4.27 (0.25). On day 22, the group treated with E had a log 10 CFU for lungs of 5.27 (0.12) and for spleens of 4.27 (0.25). On day 22, the group treated with N had a log 10 CFU for lungs of 5.51 (0.09) and spleens of 2.42 (0.48).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure which is:

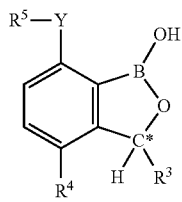

wherein R³ is CH₂NH₂;
R⁴ is bromine;
Y is O; and
R⁵ is methyl;
C* is a carbon atom stereocenter which has a configuration which is (S) or a salt, hydrate or solvate thereof.

2. A composition comprising:
a) a first stereoisomer of the compound of claim 1;
b) at least one additional stereoisomer of the first stereoisomer;

wherein the first stereoisomer is present in an enantiomeric excess of at least 80% relative to said at least one additional stereoisomer.

3. A combination comprising the compound of claim 1, or a pharmaceutically acceptable salt thereof, together with at least one other therapeutically active agent.

4. A pharmaceutical formulation comprising:
a) the compound of claim 1, or a pharmaceutically acceptable salt thereof; and
b) a pharmaceutically acceptable excipient.

5. A method of inhibiting LeuRS, comprising: contacting the LeuRS with the compound of claim 1, thereby inhibiting the LeuRS.

6. A method of killing and/or preventing the growth of *Mycobacterium tuberculosis* comprising: contacting the *Mycobacterium tuberculosis* with an effective amount of the compound of claim 1, thereby killing and/or preventing the growth of the *Mycobacterium tuberculosis*.

7. A method of treating and *tuberculosis* in an animal, comprising: administering to the animal a therapeutically effective amount of the compound of claim 1, or a pharmaceutically-acceptable salt thereof, thereby treating and/or preventing the *tuberculosis*.

8. The method of claim 7, wherein the animal is a human.

* * * * *